US008301393B2

(12) United States Patent
Palsson et al.

(10) Patent No.: US 8,301,393 B2
(45) Date of Patent: Oct. 30, 2012

(54) METHODS AND SYSTEMS FOR GENOME-SCALE KINETIC MODELING

(75) Inventors: Bernhard O. Palsson, La Jolla, CA (US); Neema Jamshidi, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 78 days.

(21) Appl. No.: 12/918,317

(22) PCT Filed: Feb. 19, 2009

(86) PCT No.: PCT/US2009/034587
§ 371 (c)(1),
(2), (4) Date: Aug. 18, 2010

(87) PCT Pub. No.: WO2009/105591
PCT Pub. Date: Aug. 27, 2009

(65) Prior Publication Data
US 2011/0010150 A1    Jan. 13, 2011

Related U.S. Application Data

(60) Provisional application No. 61/029,891, filed on Feb. 19, 2008.

(51) Int. Cl.
*G06F 19/00*    (2011.01)
(52) U.S. Cl. .......................................... 702/19
(58) Field of Classification Search .................. None
See application file for complete search history.

(56) References Cited

U.S. PATENT DOCUMENTS

| 5,556,762 | A | 9/1996 | Pinilla et al. | |
|---|---|---|---|---|
| 7,751,981 | B2 * | 7/2010 | Famili et al. | 702/19 |
| 2002/0012939 | A1 * | 1/2002 | Palsson | 435/6 |
| 2003/0233218 | A1 | 12/2003 | Schilling | |
| 2004/0029149 | A1 | 2/2004 | Palsson et al. | |
| 2005/0273305 | A1 * | 12/2005 | Thalhammer-Reyero | 703/11 |
| 2007/0174030 | A1 | 7/2007 | Yun et al. | |

FOREIGN PATENT DOCUMENTS

WO    WO 92/09300 A1    6/1992

OTHER PUBLICATIONS

Mo et al. (Molecular Biosystems (2007) vol. 3, pp. 598-603).*
Kauffman et al. (Biophysical Journal (2002) vol. 83, August; pp. 646-662).*
Duarte et al. (PNAS (2007) Feb. 6; vol. 104; pp. 1777-1782).*
Covert et al. (Nature (2004) vol. 429; pp. 92-96).*
Jamshidi and Palsson (PLoS Computational Biology (2008) vol. 4; pp. 1-10).*
Jamshidi et al. (Molecular Systems Biology 4 (2008) vol. 171, pp. 1-10).*
Price et al. (Current Opinion in Biotechnology (2007) vol. 18; pp. 365-370).*
Reed et al. (Journal of Bacteriology (2003) vol. 185, pp. 2692-2699).*
Written Opinion of the International Searching Authority and International Search Report for International Application No. PCT/US2009/034587 dated Sep. 30, 2009 by Korean Intellectual Property Office.
Atkinson, D.E. (1968). The energy charge of the adenylate pool as a regulatory parameter. Interaction with feedback modifiers. *Biochemistry*, 7(11):4030-4034.
Barabasi, et al. (2004). Network biology: understanding the cell's functional organization. *Nature Reviews Genetics*, 5:101-113.
Breitling, et al. (2008). New surveyor tools for charting microbial metabolic maps. *Nature Reviews Microbiology*, 6(2):156-161.
Decamp, et al. (1996). In Cleland and Craik (Eds.), *Protein Engineering Principles and Practice* (pp. 467-506). New York: Wiley-Liss.
Dooley et al. (1994). An all D-amino acid opioid peptide with central analgesic activity from a combinatorial library. *Science*, 266(5193):2019-2022.
Goodacre, et al. (2004). Metabolomics by numbers: Acquiring and understanding global metabolite data. *Trends Biotechnol*, 22(5):245-252.
Heinrich, R. (1985). Mathematical models of metabolic systems: general principles and control of glycolysis and membrane transport in erythrocytes. *Biomed Biochim Acta*, 44:913-927.
Heinrich, R., Rapoport, S.M. and Rapoport, T.A. (1977). Metabolic regulation and mathematical models. *Prog Biophys Mol Biol*, 32(1):1-82.
Heinrich, R. and S. Schuster. (1996). *The Regulation of Cellular Systems*. New York: Chapman & Hall, table of contents.
Heinrich, et al. (1982). Dynamics of non-linear biochemical systems and the evolutionary significance of time hierarchy. *Biosystems*, 15(4:):301-316.
Hollywood, et al. (2006). Metabolomics: Current technologies and future trends. *Proteomics*, 6(17):4716-4723.
Houghten, et al. (1991). Generation and use of synthetic peptide combinatorial libraries for basic research and drug discovery. *Nature*, 354:84-86.
Ibarra, et al. (2002). *Escherichia coli* K-12 undergoes adaptive evolution to achieve in silico predicted optimal growth. *Nature*, 420:186-189.
Ishii, et al. (2008). Comparison of metabolite production capability indices generated by network analysis methods. *Biosystems*, 91(1):166-170.
Jamshidi, et al. (2002). In silico model-driven assessment of the effects of single nucleotide polymorphisms (SNPs) on human red blood cell metabolism. *Genome Research*, 12:1687-1692.
Jamshidi, et al. (2006). Systems biology of SNPs. *Molecular Systems Biology*, 2:38, 4 pages.
Jamshidi, et al. (2007). Investigating the metabolic capabilities of *Mycobacterium tuberculosis* H37Rv using the in silico strain iNJ661 and proposing alternative drug targets. *BMC Systems Biology*, 1:26, 20 pages.
Joshi, et al. (1989). Metabolic dynamics in the human red cell. Part I-A comprehensive kinetic model. *Journal of Theoretical Biology*, 141(4):515-528.

(Continued)

*Primary Examiner* — Lori A Clow
(74) *Attorney, Agent, or Firm* — Knobbe, Martens, Olson & Bear LLP

(57) ABSTRACT

Embodiments of the present invention generally relate to the construction, analysis, and characterization of dynamical states of biological networks at the cellular level. Methods are provided for analyzing the dynamical states by constructing matrices using high-throughput data types, such as fluxomic, metabolomic, and proteomic data. Some embodiments relate to an individual, while others relate to a plurality of individuals.

51 Claims, 27 Drawing Sheets

OTHER PUBLICATIONS

Kummel, et al. (2006). Putative regulatory sites unraveled by network-embedded thermodynamic analysis of metabolome data. *Molecular Systems Biology*, 2:2006.0034.

Mayr, E. (1961). Cause and effect in biology. *Science*, 134L:1501-1506.

Oh, et al. (2007). Genome-scale reconstruction of metabolic network in *Bacillus subtilis* based on high-throughput phenotyping and gene essentiality data. *Journal of Biological Chemistry*, 282(39):28791-28799.

Pal, et al. (2006). Chance and necessity in the evolution of minimal metabolic networks. *Nature*, 440(7084):667-670.

Palsson, B. Ø. (2000). The challenges of in silico biology. *Nature Biotechnology*, 18:1147-1150.

Palsson, B. Ø. (2006). *Systems Biology: Properties of Reconstructed Networks*. Cambridge University Press, table of contents.

Palsson, et al. (1987). Reducing complexity in metabolic networks: making metabolic meshes manageable. *Fed Proc*, 46(8):2485-2489.

Papin, et al. (2004). Hierarchical thinking in network biology: The unbiased modularization of biochemical networks. *Trends in Biochemical Sciences*, 29(12):641-647.

Pharkya, et al. (2004). OptStrain: A computational framework for redesign of microbial production systems. *Genome Research*, 14:2367-2376.

Price, et al. (2004). Genome-scale models of microbial cells: Evaluating the consequences of constraints. *Nature Reviews Microbiology*, 2(11):886-897.

Ray, E. T. (2001). *Learning XML*. Sebastopol, CA: O'Reilly Media, Inc., table of contents.

Reed, et al. (2006). Towards multidimensional genome annotation. *Nature Reviews Genetics*, 7(2):130-141.

Remington, J. P. (1990). *Remington's Pharmaceuticals Sciences*, 18th Ed., E. W. Martin, et al. (Eds.), Easton, PA: Mack Printing Company, table of contents.

Resendis-Antonio, et al. (2007). Metabolic reconstruction and modeling of nitrogen fixation in *Rhizobium etli*. *PLoS Computational Biology*, 3(10):1887-1895.

Sauer, U. (2006). Metabolic networks in motion: 13C-based flux analysis. *Molecular Systems Biology*, 2:62.

Schilling et al. (2000). Assessment of the metabolic capabilities of *Haemophilus influenzae Rd* through a genome-scale pathway analysis. *J. Theor. Biol.*, 203:249-283.

Schilling et al. (2000). Theory for the Systemic Definition of Metabolic Pathways and their use in Interpreting Metabolic Function from a Pathway-Oriented Perspective. *J. Theor. Biol.*, 229-248.

Slonim, D. K. (2002). From patterns to pathways: Gene expression data analysis comes of age. *Nat Genet*, 32 Suppl, 502-508.

Strogatz, S. H. (1994). *Nonlinear Dynamics and Chaos: With Applications to Physics, Biology, Chemistry, and Engineering*. Cambridge: Perseus, table of contents.

Teusink, et al. (2000). Can yeast glycolysis be understood in terms of in vitro kinetics of the constituent enzymes? Testing biochemistry. *Eur J Biochem*, 267:5313-5329.

Wang, et al. (1988). Parental formulations of proteins and pepties; stability and stabilizers. *Journals of Parental Sciences and Technology*, Technical Report No. 10, Supp. 42:2S.

Albe, et al. 1990. Cellular concentrations of enzymes and their substrates. *J. Theor. Biol.*, 143:163-195.

Alberty, R. A. 2003. Thermodynamics of biochemical reactions. Wiley-Interscience, Hoboken, N.J. Table of contents and Preface.

Bennett, et al. 2008. Absolute quantitation of intracellular metabolite concentrations by an isotope ratio-based approach. *Nature Protocols*, 3(8):1299-1311.

Brauer, et al. 2006. Conservation of the metabolomic response to starvation across two divergent microbes. *Proc. Natl. Acad. Sci. USA*, 103(51):19302-19307.

Bruggeman, et al. 2006. Time-dependent hierarchical regulation analysis: Deciphering cellular adaptation. *IEE Proc.-Systems Biology*, 153(5):318-322.

Claus, et al. 2008. Systemic multicompartmental effects of the gut microbiome on mouse metabolic phenotypes. *Molecular Systems Biology*, 4:219.

Famili, et al. 2005. κ-Cone analysis: Determining all candidate values for kinetic parameters on a network scale. *Biophysical Journal*, 88:1616-1625.

Feist, et al. 2007. A genome-scale metabolic reconstruction for *Escherichia coli* K-12 MG1655 that accounts for 1260 ORFs and thermodynamic information. *Molecular Systems Biology*, 3:121.

Feist, et al. 2009. Reconstruction of biochemical networks in microorganisms. *Nature Reviews Microbiology*, 7:129-143.

Fong, et al. 2004. Metabolic gene-deletion strains of *Escherichia coli* evolve to computationally predicted growth phenotypes. *Nat Genet*, 36(10):1056-1058.

Grimbs, et al. 2007. The stability and robustness of metabolic states: Identifying stabilizing sites in metabolic networks. *Molecular Systems Biology*, 3:146.

Harrison, et al. 2007. Plasticity of genetic interactions in metabolic networks of yeast. *Proc. Natl. Acad. Sci. USA*, 104(7):2307-2312.

Hawkins, et al. 1987. Adenosine kinase from human erythrocytes: Kinetic studies and characterization of adenosine binding sites. *Biochemistry*, 26:1982-1987.

Heinrich, et al. 1991. Mathematical analysis of enzymic reaction systems using optimization principles. *Eur. J. Biochem.*, 201:1-21.

Henry, et al. 2006. Genome-scale thermodynamic analysis of *Escherichia coli* metabolism. *Biophysical Journal*, 90:1453-1461.

Henry, et al. 2007. Thermodynamics-based metabolic flux analysis. *Biophysical Journal*, 92:1792-1805.

Ishii, et al. 2007. Multiple high-throughput analyses monitor the response of *E. coli* to perturbations. *Science*, 316:593-597.

Jamshidi, et al. 2001. Dynamic simulation of the human red blood cell metabolic network. *Bioinformatics*, 17(3):286-287.

Jamshidi, et al. 2006. Systems biology of the human red blood cell. *Blood Cells, Molecules & Diseases*, 36:239-247.

Jamshidi, et al. 2008. Formulating genome-scale kinetic models in the post-genome era. *Molecular Systems Biology*, 4:171.

Jamshidi, et al. 2008. Top-down analysis of temporal hierarchy in biochemical reaction networks. *PLoS Computational Biology*, 4(9):eI000177.

Jankowski, et al. 2008. Group contribution method for thermodynamic analysis of complex metabolic networks. *Biophysical Journal*, 95:1487-1499.

Joshi, et al. 1990. Metabolic dynamics in the human red cell. Part III-Metabolic reaction rates. *J. Theor. Biol.*, 142:41-68.

Joshi, et al. 1990. Metabolic dynamics in the human red cell. Part IV-Data prediction and some model computations. *J. Theor. Biol.*, 142:69-85.

Kauffman, et al. 2002. Description and analysis of metabolic connectivity and dynamics in the human red blood cell. *Biophysical Journal*, 83:646-662.

Mahadevan, et al. 2003. The effects of alternate optimal solutions in constraint-based genome-scale metabolic models. *Metabolic Engineering*, 5:264-276.

Maurya, et al. 2007. A kinetic model for calcium dynamics in RAW 264.7 cells: I. Mechanisms, parameters, and subpopulational variability. *Biophysical Journal*, 93:709-728.

Mavrovouniotis, M. L. 1991. Estimation of standard Gibbs energy changes of biotransformations. *The Journal of Biological Chemistry*, 266(22):14440-14445.

Mulquiney, et al. 1999. Model of 2,3-bisphosphoglycerate metabolism in the human erythrocyte based on detailed enzyme kinetic equations: in vivo kinetic characterization of 2,3-bisphosphoglycerate synthase/phosphatase using $^{13}C$ and $^{31}P$ NMR. *Biochem J.*, 342:567-580.

Mulquiney, et al. 1999. Model of 2,3-bisphosphoglycerate metabolism in the human erythrocyte based on detailed enzyme kinetic equations: Equations and parameter refinement. *Biochem J.*, 342:581-596.

Reich, J. G. and E. E. Sel'kov. 1981. Energy Metabolism of the Cell: A Theoretical Treatise. New York: Academic Press. Table of contents.

Saucerman, et al. 2003. Modeling β-adrenergic control of cardiac myocyte contractility in silico. *The Journal of Biological Chemistry*, 278(48):47997-48003.

Scriver, C. R., A. L. Beaudet, W. S. Sly, and D. Valle. 2000. The Metabolic and Molecular Bases of Inherited Disease, 8th Ed. New York: McGraw-Hill.

Segel, I. H. 1975. Enzyme Kinetics: Behavior and Analysis of Rapid Equilibrium and Steady-State Enzyme Systems. New York: John Wiley & Sons. Table of contents.

Smallbone, et al. 2007. Something from nothing—bridging the gap between constraint-based and kinetic modelling. *The FEBS Journal*, 274:5576-5585.

Smith, et al. 2005. METLIN: A metabolite mass spectral database. *Ther Drug Monit*, 27(6):747-751.

Steuer, et al. 2006. Structural kinetic modeling of metabolic networks. *Proc. Natl. Acad. Sci. USA*, 103(32):11868-11873.

Tran, et al. 2008. Ensemble modeling of metabolic networks. *Biophysical Journal*, 95:5606-5617.

Wishart, et al. 2007. HMDB: The Human Metabolome Database. *Nucleic Acids Research*, 35:D521-D526.

* cited by examiner

THE PROPERTIES OF THE DYNAMIC MASS BALANCE EQUATIONS

A: THE FUNDAMENTAL DATA MATRICES $$2A \underset{k_1^-}{\overset{k_1^+}{\rightleftharpoons}} B \qquad K_{eq1} = \frac{k_1^+}{k_1^-}$$

$$B + X \underset{k_2^-}{\overset{k_2^+}{\rightleftharpoons}} C + Y \qquad K_{eq2} = \frac{k_2^+}{k_2^-}$$

$$v_1 = k_1^+ A^2 - k_1^- B$$
$$v_2 = k_2^+ B X - k_2^- C Y$$

$$S = \begin{pmatrix} -2 & 0 \\ 1 & -1 \\ 0 & 1 \\ 0 & -1 \\ 0 & 1 \end{pmatrix} \begin{matrix} A \\ B \\ C \\ X \\ Y \end{matrix} \qquad G = \begin{pmatrix} 2Ak_1^+ & -k_1^- & 0 & 0 & 0 \\ 0 & Xk_2^+ & -Yk_2^- & Bk_2^+ & -Ck_2^- \end{pmatrix} \begin{matrix} g_1 \\ g_2 \end{matrix}$$

B: THE PROPERTIES OF J = S·G

1: DECOMPOSITION

$$J = S \cdot G = \underbrace{S}_{\text{chemistry}} \cdot \underbrace{\kappa}_{\text{kinetics}} \cdot \underbrace{\Gamma}_{\text{thermodynamics}}$$

$$J = \begin{pmatrix} -2 & 0 \\ 1 & -1 \\ 0 & 1 \\ 0 & -1 \\ 0 & 1 \end{pmatrix} \begin{pmatrix} k_1^- & 0 \\ 0 & k_2^- \end{pmatrix} \begin{pmatrix} 2A & -1/K_{eq_1} & 0 & 0 & 0 \\ 0 & X & -Y/K_{eq_2} & B & -C/K_{eq_2} \end{pmatrix}$$

2: STRUCTURAL SIMILARITY

$$S \sim -G^T$$

$$\begin{pmatrix} - & 0 \\ + & - \\ 0 & + \\ 0 & - \\ 0 & + \end{pmatrix} \qquad \begin{pmatrix} - & 0 \\ + & - \\ 0 & + \\ 0 & - \\ 0 & + \end{pmatrix}$$

$$\text{sign}(S) \qquad \qquad -\text{sign}(G^T)$$

3: DUALITY

$$x' = x - x_{ref}$$
$$v' = G \cdot x'$$

$$\begin{array}{ccc} J_x = S \cdot G & & J_v = G \cdot S \\ \downarrow & & \downarrow \\ dx'/dt = J_x \cdot x' & \xrightarrow{G} & dv'/dt = J_v \cdot v' \end{array}$$

4: TIME SCALE HIERARCHY

$$k_1^+ \sim k_1^- \gg k_2^+ \sim k_2^-$$

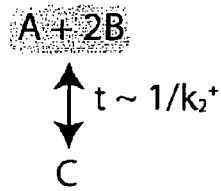

THE DYNAMIC PROPERTIES OF GLYCOLYSIS: FUNDAMENTAL PROPERTIES 3 & 4

3: DUALITY

THE JACOBIAN IN TERMS OF METABOLITES: $J|_x$ → G → THE JACOBIAN IN TERMS OF FLUXES: $J|_v$

4: TIME SCALE HIERARCHY — FROM $J|_x$ → S → FROM $J|_v$

| Figure 13-1 | Figure 13-2 | Figure 13-3 |

Figure 13

| LEX | HXEX | ADEEX | ADOEX | INOEX |
|---|---|---|---|---|
| 0.00E+00 | 0 | 0 | 0 | 0 |
| 0.00E+00 | 0.00E+00 | 0.00E+00 | 0 | 0 |
| 0 | 0.00E+00 | 0.00E+00 | 0 | 0 |
| 0 | 0 | 0 | 0 | 0 |
| 0 | 0 | 0 | 0 | 0 |
| 0 | 0 | 0 | 0.00E+00 | 0 |
| 0 | 0.00E+00 | 0 | 0.00E+00 | 0.00E+00 |
| 0 | 0.00E+00 | 0 | 0 | 0.00E+00 |
| 0 | 0.00E+00 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 1 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 1 | 0 | 0 | 0 |
| 0 | 0 | 0 | 0 | 0 |
| 0 | 0 | 1 | 0 | 0 |
| 0 | 0 | 0 | 1 | 0 |
| 0 | 0 | 0 | 0 | 1 |
| 0 | 0 | 0 | 0 | 0 |
| 0 | 0 | 0 | 0 | 0 |
| 0 | 0 | 0 | 0 | 0 |

Figure 13-3

| | GLC | G6P | F6P | FDP | DHAP | GAP | DPG13 | DPG23 | PG3 | PG2 | PEP | NAD | PYR | LAC | NADH |
|---|---|---|---|---|---|---|---|---|---|---|---|---|---|---|---|
| HK | 0.224 | -3.93E-05 | 0 | 0 | 0 | 0 | 0 | 0 | 0 | 0 | 0 | 0 | 0 | 0 | 0 |
| PGI | 0 | 1150.882 | -2676.471 | 0 | 0 | 0 | 0 | 0 | 0 | 0 | 0 | 0 | 0 | 0 | 0 |
| PFK | 0 | 0 | 69.16662 | -0.012127 | 0 | 0 | 0 | 0 | 0 | 0 | 0 | 0 | 0 | 0 | 0 |
| ALD | 0 | 0 | 0 | 145.7475 | -0.00791 | -0.165278 | 0 | 0 | 0 | 0 | 0 | 0 | 0 | 0 | 0 |
| TPI | 0 | 0 | 0 | 0 | 7.925773 | -0.452901 | 0 | 0 | 0 | 0 | 0 | 0 | 0 | 0 | 0 |
| GAPDH | 0 | 0 | 0 | 0 | 0 | 9986.091 | -161488.4 | 0 | 0 | 0 | 0 | 1145.649 | 0 | 0 | -2111.016 |
| PGK | 0 | 0 | 0 | 0 | 0 | 0 | 7037.227 | 0 | -22.29903 | 0 | 0 | 0 | 0 | 0 | 0 |
| DPGM | 0 | 0 | 0 | 0 | 0 | 0 | 1612.903 | -0.032258 | 0 | 0 | 0 | 0 | 0 | 0 | 0 |
| DPGase | 0 | 0 | 0 | 0 | 0 | 0 | 0 | 0.111112 | -0.000133 | 0 | 0 | 0 | 0 | 0 | 0 |
| PGM | 0 | 0 | 0 | 0 | 0 | 0 | 0 | 0 | 53.82792 | -7.915871 | 0 | 0 | 0 | 0 | 0 |
| EN | 0 | 0 | 0 | 0 | 0 | 0 | 0 | 0 | 0 | 582.2253 | -343.5129 | 0 | 0 | 0 | 0 |
| PK | 0 | 0 | 0 | 0 | 0 | 0 | 0 | 0 | 0 | 0 | 139.5725 | 0 | -0.79608 | 0 | 0 |
| LDH | 0 | 0 | 0 | 0 | 0 | 0 | 0 | 0 | 0 | 0 | 0 | -2.574486 | 31.97125 | -0.136684 | 80.45268 |
| AMPase | 0 | 0 | 0 | 0 | 0 | 0 | 0 | 0 | 0 | 0 | 0 | 0 | 0 | 0 | 0 |
| ADA | 0 | 0 | 0 | 0 | 0 | 0 | 0 | 0 | 0 | 0 | 0 | 0 | 0 | 0 | 0 |
| AK | 0 | 0 | 0 | 0 | 0 | 0 | 0 | 0 | 0 | 0 | 0 | 0 | 0 | 0 | 0 |
| ADK | 0 | 0 | 0 | 0 | 0 | 0 | 0 | 0 | 0 | 0 | 0 | 0 | 0 | 0 | 0 |
| AMPDA | 0 | 0 | 0 | 0 | 0 | 0 | 0 | 0 | 0 | 0 | 0 | 0 | 0 | 0 | 0 |
| ATPase | 0 | 0 | 0 | 0 | 0 | 0 | 0 | 0 | 0 | 0 | 0 | 0 | 0 | 0 | 0 |
| ADPRT | 0 | 0 | 0 | 0 | 0 | 0 | 0 | 0 | 0 | 0 | 0 | 0 | 0 | 0 | 0 |
| G6PDH | 0 | 5.611546 | 0 | 0 | 0 | 0 | 0 | 0 | 0 | 0 | 0 | 0 | 0 | 0 | 0 |
| PGLase | 0 | 0 | 0 | 0 | 0 | 0 | 0 | 0 | 0 | 0 | 0 | 0 | 0 | 0 | 0 |
| GL6PDH | 0 | 0 | 0 | 0 | 0 | 0 | 0 | 0 | 0 | 0 | 0 | 0 | 0 | 0 | 0 |
| GSSGR | 0 | 0 | 0 | 0 | 0 | 0 | 0 | 0 | 0 | 0 | 0 | 0 | 0 | 0 | 0 |
| GSHR | 0 | 0 | 0 | 0 | 0 | 0 | 0 | 0 | 0 | 0 | 0 | 0 | 0 | 0 | 0 |
| RU5PI | 0 | 0 | 0 | 0 | 0 | 0 | 0 | 0 | 0 | 0 | 0 | 0 | 0 | 0 | 0 |
| XU5PE | 0 | 0 | 0 | 0 | 0 | 0 | 0 | 0 | 0 | 0 | 0 | 0 | 0 | 0 | 0 |
| TKI | 0 | 0 | -0.98934 | 0 | 0 | -38.81581 | 0 | 0 | 0 | 0 | 0 | 0 | 0 | 0 | 0 |
| TKII | 0 | 0 | -5.697178 | 0 | 0 | -2.362603 | 0 | 0 | 0 | 0 | 0 | 0 | 0 | 0 | 0 |
| TALD | 0 | 0 | 0 | 0 | 0 | 28.27488 | 0 | 0 | 0 | 0 | 0 | 0 | 0 | 0 | 0 |
| IMPase | 0 | 0 | 0 | 0 | 0 | 0 | 0 | 0 | 0 | 0 | 0 | 0 | 0 | 0 | 0 |
| PNPase | 0 | 0 | 0 | 0 | 0 | 0 | 0 | 0 | 0 | 0 | 0 | 0 | 0 | 0 | 0 |
| PRM | 0 | 0 | 0 | 0 | 0 | 0 | 0 | 0 | 0 | 0 | 0 | 0 | 0 | 0 | 0 |
| PRPPSYN | 0 | 0 | 0 | 0 | 0 | 0 | 0 | 0 | 0 | 0 | 0 | 0 | 0 | 0 | 0 |
| HGPRT | 0 | 0 | 0 | 0 | 0 | 0 | 0 | 0 | 0 | 0 | 0 | 0 | 0 | 0 | 0 |
| GLCEX | -0.224 | 0 | 0 | 0 | 0 | 0 | 0 | 0 | 0 | 0 | 0 | 0 | 0 | 0 | 0 |
| PEX | 0 | 0 | 0 | 0 | 0 | 0 | 0 | 0 | 0 | 0 | 0 | 0 | 4.622869 | 0 | 0 |
| LEX | 0 | 0 | 0 | 0 | 0 | 0 | 0 | 0 | 0 | 0 | 0 | 0 | 0 | 4.622869 | 0 |
| HXEX | 0 | 0 | 0 | 0 | 0 | 0 | 0 | 0 | 0 | 0 | 0 | 0 | 0 | 0 | 0 |
| ADEEX | 0 | 0 | 0 | 0 | 0 | 0 | 0 | 0 | 0 | 0 | 0 | 0 | 0 | 0 | 0 |
| ADOEX | 0 | 0 | 0 | 0 | 0 | 0 | 0 | 0 | 0 | 0 | 0 | 0 | 0 | 0 | 0 |
| INOEX | 0 | 0 | 0 | 0 | 0 | 0 | 0 | 0 | 0 | 0 | 0 | 0 | 0 | 0 | 0 |

|  | IMP | INO | HX | R1P | ADE |
|---|---|---|---|---|---|
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | -745.0297 | 0 | 0 | 0 |
|  | 0 | 0 | 0 | 0 | 0 |
|  | -61.74073 | 0 | 0 | 0 | 0 |
|  | 0 | 0 | 0 | 0 | 0 |
|  | 0 | 0 | 0 | 0 | 0 |
|  | 0 | 0 | 0 | 0 | 0 |
|  | 0 | 0 | 0 | 0 | 17.40564 |
|  | 0 | 0 | 0 | 0 | 0 |
|  | 0.066611 | -7.99E-05 | -1115.041 | -37.16802 | 0 |
|  | 0 | 2453.089 | 0 | 3.776761 | 0 |
|  | 0 | 0 | 72.51606 | 0 | 0 |
|  | 0 | 0 | 0 | 0 | 0 |
|  | -2.088463 | 0 | 52.65838 | 0 | 0 |
|  | 0 | 0 | 0 | 0 | 0 |
|  | 0 | 0 | 0 | 0 | 52.7777 |
|  | 0 | 3.859797 | 0 | 0 | 0 |

Figure 14-3

| Figure 14-1 | Figure 14-2 | Figure 14-3 |
|---|---|---|

Figure 14

METHODS AND SYSTEMS FOR GENOME-SCALE KINETIC MODELING

RELATED APPLICATIONS

This application is the U.S. National Phase under 35 U.S.C. §371 of International Application No. PCT/US2009/034587 filed Feb. 19, 2009 under the Patent Cooperation Treaty (PCT), designating the United States, and published in English as WO2009/105591 on Aug. 27, 2009, which claims the benefit of U.S. Provisional Patent Application Ser. No. 61/029,891 filed Feb. 19, 2008, the disclosures of which are hereby incorporated herein by reference in their entireties.

STATEMENT OF GOVERNMENT SUPPORT

This invention was made with government support under grant number BNGBP47 awarded by NIH. The government has certain rights in the invention.

BACKGROUND OF THE INVENTION

1. Field of the Invention

Embodiments of the present invention generally relate to the construction, analysis, and characterization of dynamical states of biological networks at the cellular level. Methods are provided for analyzing the dynamical states by constructing matrices using high-throughput data types, such as fluxomic, metabolomic, and proteomic data. Some embodiments relate to an individual, while others relate to a plurality of individuals.

2. Description of the Related Art

There have been significant advances in the development of statistical analysis of genome-scale networks (Slonim, 2002), that have been propelled by the availability of genome-scale high-throughput datasets and the successes of constraint-based modeling approaches (Kummel et al., 2006; Palsson, 2006; Pharkya et al., 2004; Price et al., 2004; Reed et al., 2006). The foundation of such genome-scale analysis is built upon the descriptions of the biochemical transformations in a network in a self-consistent and chemically accurate matrix format. Much progress has been made with the genome-scale network reconstruction process, and a growing number of genome-scale metabolic reconstructions are now available (Feist et al., 2007; Jamshidi and Palsson, 2007; Oh et al., 2007; Reed et al., 2006; Resendis-Antonio et al., 2007).

Reconstructions of genome-scale biochemical reaction networks (Reed et al., 2006) have been analyzed by topological (Barabasi and Oltvai, 2004) and constraints-based (Price et al., 2004) methods, but dynamic models, at this scale, have been unachievable to date. It turns out that the matrix representation of the biochemical transformations in a network are not only a requisite for dynamic models but also a major determinant in their properties, and thus, it is important to have well curated reconstructions available. The growing availability of metabolomic and fluxomic data sets (Breitling et al., 2007; Goodacre et al., 2004; Hollywood et al., 2006; Sauer, 2006) and methods to estimate the thermodynamic properties (Henry et al., 2007; Henry et al., 2006; Mavrovouniotis, 1991) of biochemical reactions has opened up the possibility to formulate large-scale kinetic models.

The growing amount of disparate data sets (including proteomic, fluxomic, and metabolomic) has produced the unmet need to integrate and analyze this data in a functional context that is tailored to specific individuals. The availability of annotated genomes enabled the reconstruction of genome-scale networks, and now the availability of high-throughput metabolomic and fluxomic data along with thermodynamic information opens the possibility to build genome-scale kinetic models. This invention describes a framework for building and analyzing such models, thus satisfying those needs.

SUMMARY OF THE INVENTION

The structure of the workflow that leads to large-scale dynamic models is described in this invention along with the description of the framework which enables the integration of data to construct genome-scale kinetic models.

A description of the types of data matrices which are needed to construct large-scale kinetic models of biological processes is provided.

A description of the way to construct the data matrices needed for the formulation of kinetic models is provided. A description of important properties of these data matrices which enable approximations of the values in the data matrices when partial or incomplete data is available is also provided.

A method for the analysis of kinetic models and for providing a method for interpreting and predicting physiological and pathophysiological states of biological reaction networks is provided.

A method is provided for developing data-driven dynamic models of biological networks, the method comprising providing a data structure relating a plurality of biological network reactants to a plurality of biological network reactions, wherein each of the biological network reactions comprises one or more biological network reactants identified as a substrate of the reaction, one or more biological network reactants identified as a product of the biological network reaction and a stoichiometric coefficient relating the substrate and the product; providing a constraint set for a plurality of biological network reactions; providing a constraint set for the plurality of concentrations associated with the plurality of biological network reactions; providing a constraint set for a plurality of kinetic constants associated with the plurality of biological network reactions; providing a constraint set for a plurality of equilibrium constants associated with the plurality of biological network reactions; integrating the sets of constraints, thereby forming the stoichiometric, gradient, and Jacobian matrices; providing an objective function; and predicting a physiological function related to a biological network by determining at least one flux distribution that minimizes or maximizes the objective function when the constraint set is applied to the data structure.

A method is provided wherein the constraints for the plurality of reactions, the constraints for the plurality of concentrations, the constraints for the plurality of kinetic constants, and the constraints for the plurality of equilibrium constants are uniquely defined.

A method is provided wherein providing a constraint set for a plurality of concentrations comprises measuring metabolite levels at steady state.

A method is provided, wherein providing a constraint set for a plurality of kinetic constants comprises solving a steady state mass conservation relationship comprising a stoichiometric matrix and flux vector.

A method is provided further comprising defining a unique set of matrices using the objective function, wherein the constraints within at least one of the sets selected from the reactions constraint set, the concentration constraint set, the kinetic constant constraint set, and the equilibrium constraint set are not unique across the set.

A method is provided further comprising defining a unique set of gradient and Jacobian matrices using order of magnitude approximations, wherein the constraints within at least one of the sets selected from the reactions constraint set, the concentration constraint set, the kinetic constant constraint set, and the equilibrium constraint set are not unique across the set.

A method is provided further comprising determining a set of gradient and Jacobian matrices corresponding to the plurality of constraint conditions, wherein the constraints within at least one of the sets selected from the reactions constraint set, the concentration constraint set, the kinetic constant constraint set, and the equilibrium constraint set are not unique across the set.

A method is provided wherein constraints within at least one of the concentration constraint set and the kinetic constant constraint set are not unique across the set and are estimated by order of magnitude approximations.

A method is provided wherein the stoichiometric, gradient, and Jacobian matrices refer to a biological network process.

A method is provided wherein the biological network process comprises at least one of metabolism, signal transduction or signaling, transcription, and translation.

A method is provided wherein the sets of constraints correspond to an individual.

A method is provided wherein the sets of constraints correspond to a group or plurality of individuals.

A method is provided wherein the model is used to determine the effects of changes from aerobic to anaerobic conditions.

A method is provided wherein the biological network reactions are obtained from a metabolic reaction database that includes the substrates, products, and stoichiometry of a plurality of biological reactions.

A method is provided for the analysis of disease states due to genetic and or environmental influences, the method comprising providing a data structure relating a plurality of reactants to a plurality of reactions, wherein each of the reactions comprises one or more reactants identified as a substrate of the reaction, one or more reactants identified as a product of the reaction and a stoichiometric coefficient relating the substrate and the product; providing a constraint set for the plurality of reactions; providing a constraint set for a plurality of concentrations associated with the plurality of reactions; providing a constraint set for a plurality of kinetic constants associated with the plurality of reactions; providing a constraint set for a plurality of equilibrium constants associated with the plurality of reactions; integrating the sets of constraints, thereby forming the stoichiometric, gradient, and Jacobian matrices; providing an objective function; modifying at least one of the reaction constraint set, the concentration constraint set, the constraint set for a plurality of kinetic constants and the set for a plurality of equilibrium constants based at least partly on altered environmental conditions; and predicting a physiological function related to the disease state by determining at least one flux distribution that minimizes or maximizes the objective function when at least one constraint set is applied to the data structure.

A method is provided wherein the model is used to determine the dynamics and consequences of genetic defects selected from the group consisting of deficiencies in metabolic enzymes and metabolic transporters.

A method is provided wherein the genetic defects comprise the functioning of a compound selected from the group consisting of phosphofructokinase, phosphoglycerate kinase, phosphoglycerate mutase, lactate dehydrogenase adenosine deaminase, ABC transporters, the SLC class of transporters, and the cytochrome P450 class of enzymes.

A method is provided wherein providing a constraint set for a plurality of concentrations comprises measuring metabolite levels at steady state.

A method is provided wherein providing a constraint set for a plurality of kinetic constants comprises solving a steady state mass conservation relationship comprising a stoichiometric matrix and flux vector.

A method is provided wherein the modified sets of constraints correspond to an individual.

A method is provided wherein the modified sets of constraints correspond to a group or plurality of individuals.

A method is provided wherein a therapeutic regime is applied to regulate a physiological function based on at least one of the modified sets based at least partly on genetic variations.

A method is provided wherein a therapeutic regime is applied to regulate a physiological function based on at least one of the modified sets based at least partly on altered environmental conditions.

A method is provided for the analysis of therapies for drug treatments, the method comprising providing a data structure relating a plurality of reactants to a plurality of reactions, wherein each of the reactions comprises one or more reactants identified as a substrate of the reaction, one or more reactants identified as a product of the reaction and a stoichiometric coefficient relating the substrate and the product; providing a constraint set for the plurality of reactions; providing a constraint set for a plurality of concentrations associated with the plurality of reactions; providing a constraint set for a plurality of kinetic constants associated with the plurality of reactions; providing a constraint set for a plurality of equilibrium constants associated with the plurality of reactions; integrating the sets of constraints, thereby forming the stoichiometric, gradient, and Jacobian matrices; providing an objective function; providing a experimental constraint set for the plurality of reactions, concentrations, or kinetic constants for an altered set of constraints due to the treatment with a drug or chemical agent; and predicting a physiological function related to a drug treatment by determining at least one flux distribution that minimizes or maximizes the objective function when a constraint set is applied to the data structure.

A method is provided wherein a set of fluxes and concentrations are measured in an individual before and after giving a dose of a therapeutic agent to the individual and constructing kinetic network models according to the measured data specific to the individual.

A method is provided wherein providing a constraint set for a plurality of concentrations comprises measuring metabolite levels at steady state.

A method is provided wherein providing a constraint set for a plurality of kinetic constants comprises solving a steady state mass conservation relationship comprising a stoichiometric matrix and flux vector.

A method is provided wherein a physiological function related to a drug treatment is instead predicted by determining at least one concentration that maximizes or minimizes the objective function when the experimental constraint set is applied to the data structure.

A method is provided wherein a drug or chemical agent is applied to regulate a physiological function based on the at least one experimental constraint set for an altered state of constraints due to the treatment with a drug or chemical agent.

A method is provided wherein a drug or chemical agent is applied to regulate a physiological function based on the at least one experimental constraint set which maximizes or minimizes the objective function when the experimental constraint set is applied to the data structure.

A method is provided wherein the sets of constraints correspond to an individual.

A method is provided wherein the sets of constraints correspond to a group or plurality of individuals.

A method is provided for accounting for small metabolite regulation, the method comprising: providing a data structure relating a plurality of reactants to a plurality of reactions, wherein each of the reactions comprises one or more reactants identified as a substrate of the reaction, one or more reactants identified as a product of the reaction and a stoichiometric coefficient relating the substrate and the product, in which the reactions may reflect regulatory processes; providing a constraint set for the plurality of reactions; providing a constraint set for a plurality of concentrations associated with the plurality of reactions; providing a constraint set for a plurality of kinetic constants associated with the plurality of reactions; providing a constraint set for a plurality of equilibrium constants associated with the plurality of reactions; integrating the sets of constraints, thereby forming the stoichiometric, gradient, and Jacobian matrices; providing an objective function; and predicting a physiological function related to the small metabolite regulation by determining at least one flux distribution that minimizes or maximizes the objective function when the constraint set is applied to the data structure.

A method is provided wherein providing a constraint set for a plurality of concentrations comprises measuring metabolite levels at steady state.

A method is provided wherein a physiological function related to the small metabolite regulation is instead predicted by determining at least one concentration that minimizes or maximizes the objective function when the constraint set is applied to the data structure.

A method is provided wherein reactants and products include proteins that interact with a plurality of other components.

A method is provided wherein reactants or products activate a particular enzyme or plurality of enzymes.

A method is provided wherein reactants or products inhibit a particular enzyme or plurality of enzymes.

A method is provided for determining one or more parameters to characterize different functional states, the method comprising: analyzing a network function; determining time scales of interest; and identifying parameters that describe the network function.

A method is provided wherein the parameters comprise at least one of a reaction, a concentration and a rate constant.

A method is provided further comprising characterizing the dynamic behavior of the network using the time scale determination; and identifying reactions or concentrations that determine the network function.

A computer readable medium is provided, the medium containing software that, when executed, causes the computer to perform the acts of: providing a data structure relating a plurality of reactants to a plurality of reactions, wherein each of the reactions comprises one or more reactants identified as a substrate of the reaction, one or more reactants identified as a product of the reaction and a stoichiometric coefficient relating the substrate and the product; providing a constraint set for the plurality of reactions; providing a constraint set for a plurality of concentrations associated with the plurality of reactions; providing a constraint set for a plurality of kinetic constants associated with the plurality of reactions; providing a constraint set for a plurality of equilibrium constants associated with the plurality of reactions; integrating the sets of constraints, thereby forming the stoichiometric, gradient, and Jacobian matrices; providing an objective function; and predicting a physiological function by determining at least one flux distribution that minimizes or maximizes the objective function when the constraint set is applied to the data structure.

A computer implemented system is provided comprising: a computing environment; a storage in data communication with the computing environment and configured to store data structure relating a plurality of reactants to a plurality of reactions; and a software program operating on the computing environment and configured to: provide the data structure relating the plurality of reactants to the plurality of reactions, wherein each of the reactions comprises one or more reactants identified as a substrate of the reaction, one or more reactants identified as a product of the reaction and a stoichiometric coefficient relating the substrate and the product; provide a constraint set for the plurality of reactions; provide a constraint set for a plurality of concentrations associated with the plurality of reactions; provide a constraint set for a plurality of kinetic constants associated with the plurality of reactions; provide a constraint set for a plurality of equilibrium constants associated with the plurality of reactions; integrate the sets of constraints, thereby forming the stoichiometric, gradient, and Jacobian matrices; provide an objective function; and predict a physiological function by determining at least one flux distribution that minimizes or maximizes the objective function when the constraint set is applied to the data structure.

A system is provided comprising means for providing a data structure relating a plurality of reactants to a plurality of reactions, wherein each of the reactions comprises one or more reactants identified as a substrate of the reaction, one or more reactants identified as a product of the reaction and a stoichiometric coefficient relating the substrate and the product; means for providing a constraint set for the plurality of reactions; means for providing a constraint set for a plurality of concentrations associated with the plurality of reactions; means for providing a constraint set for a plurality of kinetic constants associated with the plurality of reactions; means for providing a constraint set for a plurality of equilibrium constants associated with the plurality of reactions; means for integrating the sets of constraints, thereby forming the stoichiometric, gradient, and Jacobian matrices; means for providing an objective function; and means for predicting a physiological function by determining at least one flux distribution that minimizes or maximizes the objective function when the constraint set is applied to the data structure.

BRIEF DESCRIPTION OF THE DRAWINGS

FIG. 3B explicitly illustrates the principle of duality and time scale decomposition via the resulting data matrices. The Jacobian duals are shown; they are related by the gradient matrix. Hierarchical analysis can be carried out of the network in terms of metabolites or fluxes. The resultant modal matrices can be related to one another via the stoichiometric matrix.

FIG. 4 shows the hierarchical reduction of glycolysis.

FIG. 14 is a table of the gradient matrix G for the mass action study of the red blood cell, which for ease of viewing is represented in FIGS. 14-1, 14-2, 14-3.

DETAILED DESCRIPTION OF THE PREFERRED EMBODIMENT

Figure 2:
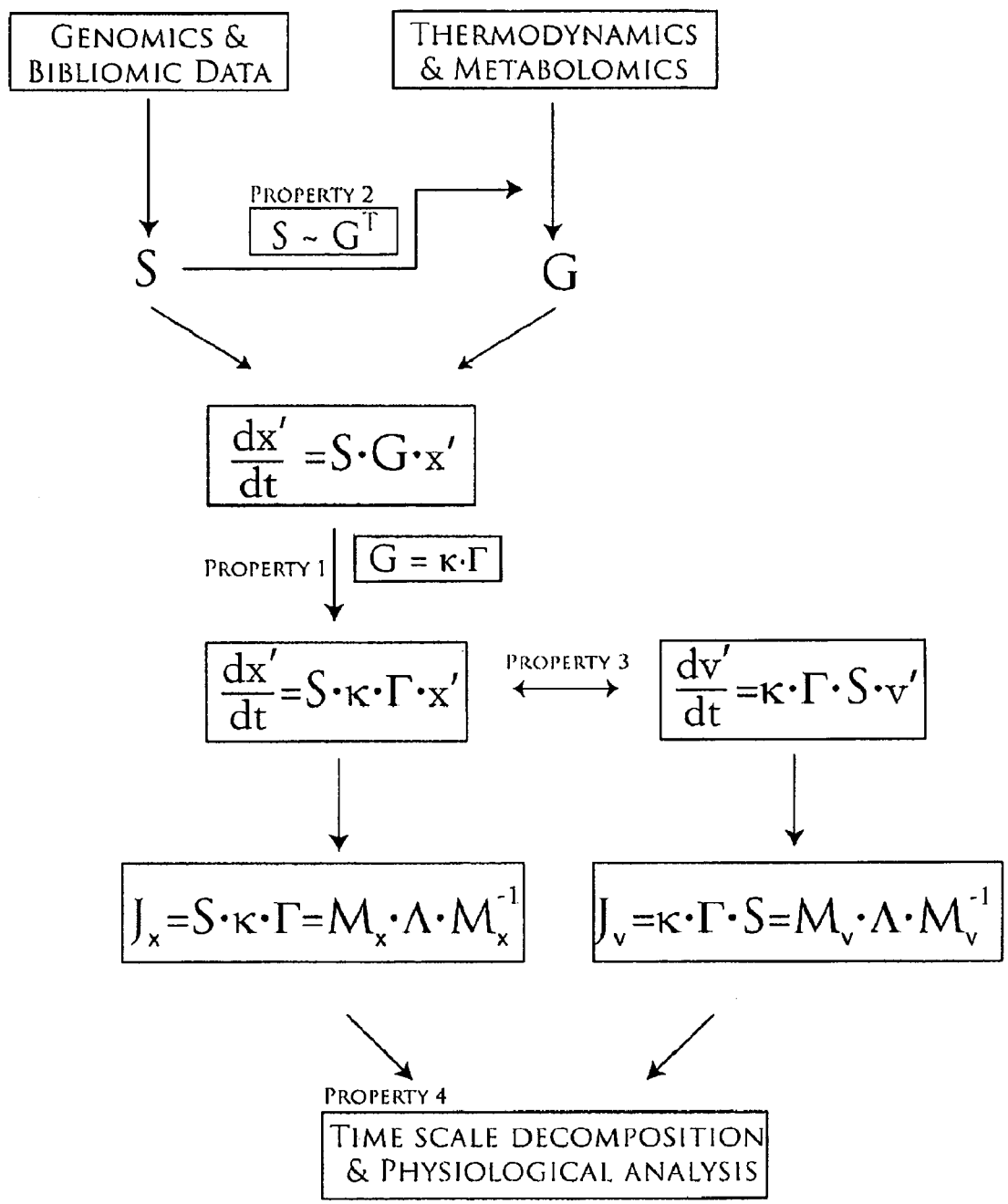
FIG. 2 is a graphical diagram illustrating a workflow for constructing approximations to genome-scale kinetic networks and how the four properties discussed in this manuscript and highlighted in FIG. 1 enable such reconstructions.

Methods for constructing and analyzing dynamic in silico models of biological networks are provided herein. A dynamic model can be used to simulate different aspects of cellular behavior of human cells under different environmental and genetic conditions, thereby providing valuable information for a range of industrial and research applications. Models and methods disclosed herein can also be extended to simulate the activity of multiple interacting cells, including organs, physiological systems, and whole body metabolism. Developing kinetic models of biological networks can be used to inform and guide the research process, potentially leading to the identification of new enzymes, medicines or metabolites of commercial importance.

As used herein, the term "concentration" refers to a numerical value with physical units of mass*volume$^{-1}$, such as molar and millimolar. Such quantities include but are not limited to molecules in a biochemical network, such as glucose, pyruvate, lactate, enzymes that carry out biochemical transformations or transport reactions such as hexokinase, adenosine deaminase, and sodium-potassium ATPase pump, or the number of cells in a volume of tissue.

As used herein, the term "initial conditions" refers to the set of initial variable values that need to be specified for carrying out dynamic simulations in a system of dynamic differential equations.

As used herein, the term "dynamic mass balance" refers to a linear first order differential equation with respect to time which accounts for the summed reactions producing or consuming each component in a specified biological network.

As used herein the term "flux" or "reaction flux" refers to a single flux in a flux distribution. Individual fluxes can be represented as the difference between a forward and reverse flux, with units mass, or number of moles, or number of molecules per unit volume per unit time.

As used herein, the term "flux distribution" refers to a directional, quantitative list of values corresponding to the set of reactions in a network, representing the mass flow per unit time for each reaction in the network being analyzed.

As used herein, the term "concentration distribution" refers to a non-negative, quantitative list of values corresponding to the set of concentrations of variables, including but not limited to metabolites and enzymes, in a network, representing the mass, or number of moles, or number of molecules per unit volume for each variable.

As used herein, the term "biological network" refers to assembled reactions reflecting biological processes. Examples of biological networks include but are not limited to metabolic networks, signaling networks, and regulatory networks.

As used herein, the term "stoichiometric matrix" or "S" refers to a matrix with the stoichiometric coefficients for reactions represented by the columns and the substrates and products in the rows. The stoichiometric matrix may be written for any biological network. Examples include but are not limited to metabolic networks and signaling networks.

As used herein, the term "gradient matrix" or "G" refers to a matrix whose row entries are the first order partial derivatives of reaction fluxes with respect to the metabolites (see equation 2). The gradient matrix is specific for a particular biological network. The number of rows in the gradient matrix is equal to the number of reactions in the network. The number of columns in the gradient matrix is equal to the number of metabolites or compounds in the network.

As used herein, the term "Jacobian", "Jacobi matrix", "Jacobian matrix", "J", or "$J_x$" refers to a matrix of the first order partial derivatives of the linearized dynamic mass balances, in which the variables are the metabolites or compounds. The Jacobian matrix is derived when a system of differential equations is linearized around a reference state such that only the first order terms remain. The Jacobian is a square matrix and has the same number of rows and columns as there are metabolites or compounds in the network. "J" can be written as the matrix product of S and G (see equations 1 and 3).

As used herein, the term "flux Jacobian" or "$J_v$" refers to a matrix of the first order partial derivatives of the linearized dynamic mass balances, in which the variables are the fluxes. The flux Jacobian is a square matrix and has the same number of rows and columns as there are reactions or fluxes in the network. The flux Jacobian can be written as the matrix product of G and S (see equation 5).

As used herein, the term "kappa", "kappa matrix", or $\kappa$ refers to a diagonal matrix composed of kinetic constants. This matrix can be calculated in a variety of ways. For example the rows of G can be scaled or normalized. The factorization may be carried out but not limited to the following manner, by factoring out the 1-norm, 2-norm, or sum of the rate constants with non-zero entries in the row.

As used herein, the term "gamma", "gamma matrix", or $\Gamma$ refers to resulting matrix after $\kappa$ has been factored out of G.

As used herein, the term "transpose", transpose of a matrix, or refers to a standard mathematical operation in which the elements of a matrix are reflected about the diagonal entries of the matrix, such that following the transformation the entries in the rows of the matrix now appear in the columns of the matrix and the entries in the columns of the matrix appear in the rows of the matrix.

As used herein, the term "time constant" refers to a numerical value with physical units of time, such as days, hours, minutes, and microseconds. Examples of time constants include but are not limited to the negative reciprocal of eigenvalues or the reciprocal entries of the kappa matrix, which may correspond to a particular reaction or set of reactions.

As used herein, the term "kinetic constant" or reaction rate constant refers to a time constant characteristic of a particular reaction or set of reactions. The physical units are [concentration]$^{-n+1}$*time$^{-1}$, where n is the kinetic order of the corresponding reaction. For example, a zero order, first order, and second order kinetic constant has units [concentration]*time$^{-1}$, time$^{-1}$, and concentration$^{-1}$*time$^{-1}$ respectively.

As used herein, the term "steady state" refers to any of a number of conditions for which the flux distribution and concentration distribution do not change over time. Equilibrium is a special case which also satisfies the steady state. In general, unless otherwise specified, references to the steady state imply a non-equilibrium steady state.

As used herein, the term "concentration deviation variable", "deviation variable", or x' is vector equal to the concentration variable vector minus a reference state. This reference state may be one of any number of concentration distributions including but not limited to steady state concentrations.

As used herein, the term "time scale decomposition" refers to the established practice of characterizing network dynamics by decomposing the Jacobian matrix into its constituent eigenvectors and eigenvalues, from which dynamically independent modes and time constants can be derived.

As used herein, the term "modal matrix" or "modes" refers to the inverse of the eigenvector matrix of J.

The reconstruction of a genome-scale reaction network requires the identification of all its chemical components and the chemical transformations that they participate in. This process primarily relies on annotated genomes and detailed bibliomic assessment. See Reed et al., 2006, which is hereby incorporated by reference in its entirety. The result of this process is the stoichiometric matrix, S, that is used in the dynamic mass balances $$dx/dt = S \cdot v(x) \, x = x_0 \text{ at time } t=0 \quad (1)$$

that are the basis of all kinetic models. Here d(•)/dt denotes the time derivative, x is the vector of the concentrations of the compounds in the network and v(x) is the vector of the reaction rates. All biochemical transformations are fundamentally uni- or bi-molecular. Such reactions can be represented by mass action kinetics, or generalizations thereof. See Segel, 1975, which is hereby incorporated by reference in its entirety. The net reaction rate for every elementary reaction in a network can be represented by the difference between a forward and reverse flux (e.g. see FIG. 1). This commonly used formulation is based on several well-known assumptions, such as constant temperature, volume, and homogeneity of the medium. If S, v(x) and the initial conditions ($x_0$) are known, then these ordinary differential equations can be numerically solved for a set of conditions of interest.

Figures 1, 13:
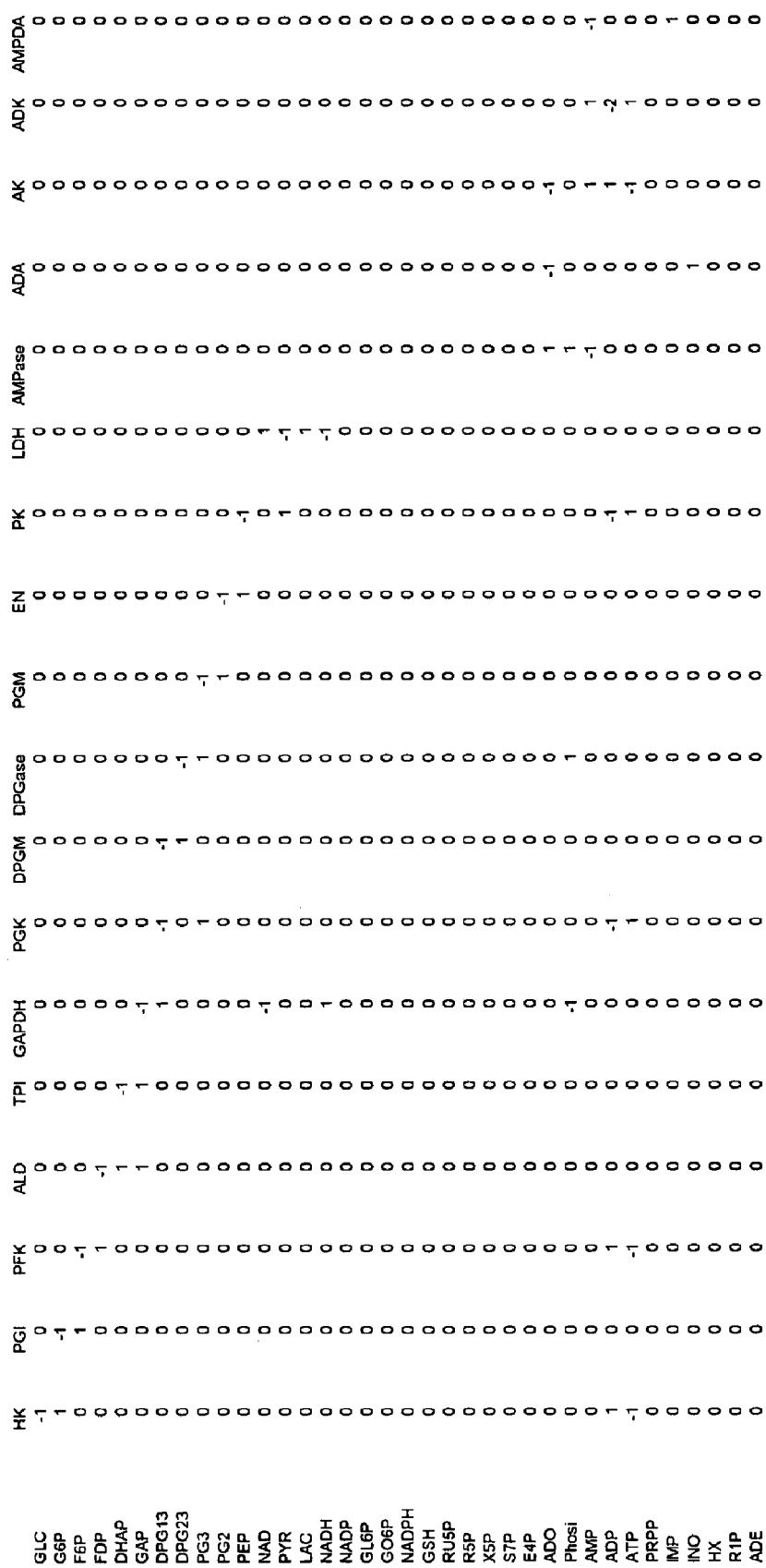
FIG. 1 is a graphical diagram showing relationships between the fundamental data matrices describing dynamic states of biological networks: the stoichiometric matrix S and the gradient matrix G.
FIG. 13 is a table of the stoichiometric matrix S for the mass action study of the red blood cell, which for ease of viewing is represented in FIGS. 13-1, 13-2, 13-3.
Figures 2, 13:
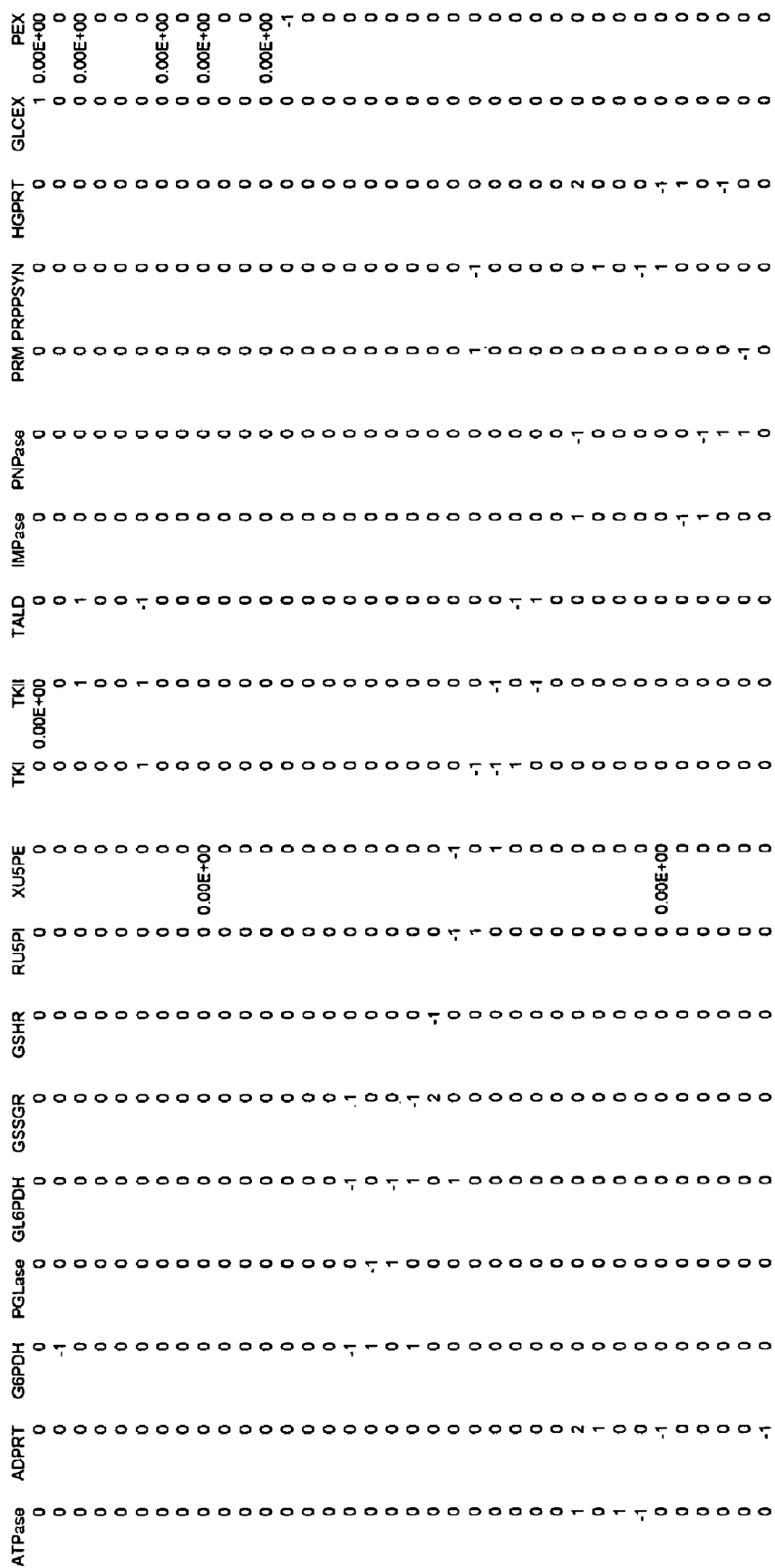

FIG. 1 shows a structural similarity between S and $G^T$, highlighted by the fact that their row reduced forms are equivalent and illustrated for a simple example involving two reactions. The corresponding stoichiometric matrix and gradient matrix (for mass action kinetics) is shown. The decomposition of the Jacobian matrix into the stoichiometric and gradient matrices is biologically meaningful and driven by the underlying chemistry, kinetics, and thermodynamics. There are different ways to factor G into F and the diagonal κ matrix. In the embodiment shown in FIG. 1, the forward rate constant is factored out of G. A duality exists between the concentrations and fluxes. The practical significance of this complementary relationship is that in the linear regime, the relationship between fluxes and concentrations can be determined independently of the specific rate law formulation, if one can approximate the gradient matrix. When certain reactions occur much faster than others, the related metabolites pool together into aggregate variables. For the example in A, when the forward and reverse rate constants of the first reaction (2A↔B; dimerization reaction) are much faster than the rate constants for the second reactions (B+X↔C+Y; cofactor exchange reaction), then the substrate and products of the first reaction form an aggregate pool. Since B is a 'dimer' of A, the pool will consist of A and B in a 1:2 ratio. Furthermore, since the first reaction occurs much more quickly than the second, the interaction between the A+2B pool and the C(X and Y are considered cofactors in this example) is determined by the rate constant(s) for the second reaction.

The characterization of the dynamic states of networks can be studied through numerical simulation or through using mathematical analysis. A simulation is context-dependent and represents a case study. Mathematical methods for the analysis of model characteristics typically rely on studying the properties of the transformation between the concentrations and fluxes. The analysis of such fundamental properties normally relies on the linearization of the governing equations at a defined condition. The linearization of the dynamic mass balance equations comes down to the linearization of the reaction rate vector to form the gradient matrix $$G=[g_{ij}]=[\partial v_i/\partial x_j] \quad (2)$$

in which $\partial \cdot/\partial x_j$ is the partial derivative operator. The Jacobian matrix at a reference state $x_{ref}$ can then be described:

$$dx'/dt = S \cdot G \cdot x' = J \cdot x' \quad (3)$$

where $x'=x-x_{ref}$ and J is the well-known Jacobian matrix. Analysis of the characteristics of Jacobian matrix is standard procedure in mathematical analysis of system dynamics (e.g. Strogatz, 1994, which is hereby incorporated by reference in its entirety). The application of these methods to biochemical networks has been carried out for decades. See Heinrich et al., 1977; Heinrich et al., 1991; Heinrich and Sonntag, 1982; Palsson et al., 1987, all of which are hereby incorporated by reference in their entireties. In recent years there has been renewed interest and recently further developments in the dynamic analysis of the properties of J have appeared. See Bruggeman et al., 2006; Famili et al., 2005; Grimbs et al., 2007; Kauffman et al., 2002; Steuer et al., 2006; Teusink et al., 2000, all of which are hereby incorporated by reference in their entireties.

The integration of genomic, bibliomic, fluxomic, and metabolomic data with thermodynamic information into dynamic models of metabolism is illustrated in FIG. 2. The process of reconstructing S is now well developed. See Palsson, 2006, which is hereby incorporated by reference in its entirety. The formulation of G can now be performed based on metabolomic data and methods to estimate thermodynamic properties. The chemical equations that make up S determine the location of the non-zero elements in G and hence its structure.

The availability of genomic and bibliomic data can be used to define S (FIG. 1), which has been described in detail (Palsson, 2006). The increasing availability of metabolomic data and approximations of thermodynamic parameters, such as the equilibrium constants for reactions, will enable the definition of G for various networks. The definition of both S and G subsequently enable the calculation of J and $J_v$. The definition of the concentration and flux Jacobian matrices provide the basis for the characterization and analysis of the dynamic properties of a network.

Table 1A compares properties of S and G, highlighting important features. For example, the formation of pools and reaction co-sets is determined by S. See Heinrich and Schuster, 1996; Jamshidi and Palsson, 2006; Papin et al., 2004, all of which are incorporated by reference in their entireties. However, time scale separation is in the realm of G. This decomposition factors the various underlying data needed for the formulation of genome-scale kinetic models. Furthermore, it illustrates the various underlying disciplinary interests that need to be considered and integrated to successfully achieve the analysis of dynamic states of genome-scale networks.

TABLE 1A

A comparison of the properties of the stoichiometric matrix and gradient matrix.

TABLE 1

A comparison of the properties of the stoichiometric matrix and gradient matrix.

| Properties | Stoichiometric Matrix | Gradient Matrix |
|---|---|---|
| biological | species differences<br>distal causation | individual differences<br>proximal causation |
| genetic | genomic characteristics<br>represents a secies | genetic characteristics<br>represents an individual |
| informatic | annotated genome<br>bibliomic<br>comparative genomics | kinetic data<br>metabolomics<br>fluxomics |
| physico-chemical | chemistry<br>conservation laws | kinetics<br>thermodynamics |
| mathematical | integer entries<br>knowable matrix | real numbers<br>entries have errors |
| numerical | sparse<br>well-conditioned<br>non-stiff | sparse<br>ill-conditioned<br>leads to stiffness |
| systemic | pool formation<br>network structure | time scale separation<br>dynamic function |

As mentioned supra, simulation is context-dependent and the respective values will depend on the domain being modeled.

For example, in the bioinformatic context, S is primarily derived from an annotated genomic sequence fortified with any direct bibliomic data on the organisms' gene products. The construction of G will rely on fluxomic and metabolmic data, in addition to direct kinetic characterization of individual reactions and assessment of thermodynamic properties.

In the physico-chemical context, S represents chemistry (i.e. stoichiometry of reactions), while G represents kinetics and thermodynamics. The chemical information is relatively easy to obtain, the thermodynamics information harder but possible (see Henry et al., 2007, which is incorporated by reference in its entirety), and the kinetic information is the hardest to acquire. The former two represent hard physico-chemical constraints, while the third represents biologically manipulable numbers; i.e., reaction rates are accelerated by enzymes.

In the biological and genetic considerations context, the matrix S is reconstructed based on the content of a genome and is a property of a species. It has thus been used productively for the analysis of distal causation (Fong and Palsson, 2004; Harrison et al., 2007; Ibarra et al., 2002; Pal et al., 2006, which are all incorporated by reference in their entireties). Distal (or ultimate) causation results from (genomic) changes that occur from generation to generation, in contrast to proximal (or proximate) causation which occurs against a fixed genetic background (i.e. an individual) (Mayr, 1961, which is incorporated by reference in its entirety). G is genetically derived and can represent the variations amongst individuals in a biopopulation. It is important in studying proximal causation and the differences in phenotypes of individuals in a biopopulation. For example, many disease states in higher order organisms result from disruptions or deficiencies in enzyme kinetics (Jamshidi et al., 2002, which is incorporated by reference in its entirety). These changes are reflected in G since this contains the information about kinetics, consequently the analysis of disease states, inter-individual differences, and transitions from a healthy to disease state in a particular individual will generally focus on G.

Generally speaking, the equations (S) will represent the pertinent physical laws and the matrices (G) will represent data. Whereas S is a 'perfect' matrix comprised of integers (i.e., digital), G is an analog matrix whose entries are real numbers, and values of G may only be known within an order of magnitude. From a numerical and mathematical standpoint, S is a well conditioned matrix comprised of integers $(-2,-1,0,1,2)$, whereas G is an ill-conditioned matrix of real numbers that can differ up to 10 orders of magnitude in their numerical values. This property leads to time scale separation. Both matrices are sparse; that is most of their elements are zero.

The elements of G, in the absence of comprehensive fluxomic, metabolomic, or thermodynamic information, may be approximated to the appropriate order of magnitude in order to enable the construction of a kinetic model for analysis.

The wide differences in the numerical values of the entries of G leads to its factorization ($G=\kappa \cdot \Gamma$) by scaling it by the length of its rows to yield a factorization of J into three matrices:

$$J = S \cdot \kappa \cdot \Gamma \quad (4)$$

where $\kappa$ is a diagonal matrix of the norms of the rows in G (FIG. 1.B.1). We emphasize that the $i_{th}$ column of S contains the stoichiometric coefficients of the $i_{th}$ reaction in the network and the $i_{th}$ row in G contains the forward and reverse rate constants of that same reaction. Thus, the reciprocal of the diagonal entries, $1/\kappa_{ii}$, correspond to characteristic time constants of the corresponding reactions. Their numerical values will differ significantly.

The factorization of the Jacobian in equation (4) shows that the study of the dynamic properties of biochemical networks can be formally decomposed into chemistry (represented by S), kinetics (represented by $\kappa$), and thermodynamic driving forces (represented by $\Gamma$). The effects of each can thus be formally determined. Chemistry and thermodynamics are physico-chemical properties, whereas the kinetic constants are biologically set through a natural selection process. The particular numerical values (chosen through the selection process) lead to the formation of biologically meaningful dynamic properties of the network. These biological features of the network can be assessed through time scale decomposition.

Figure 3A:
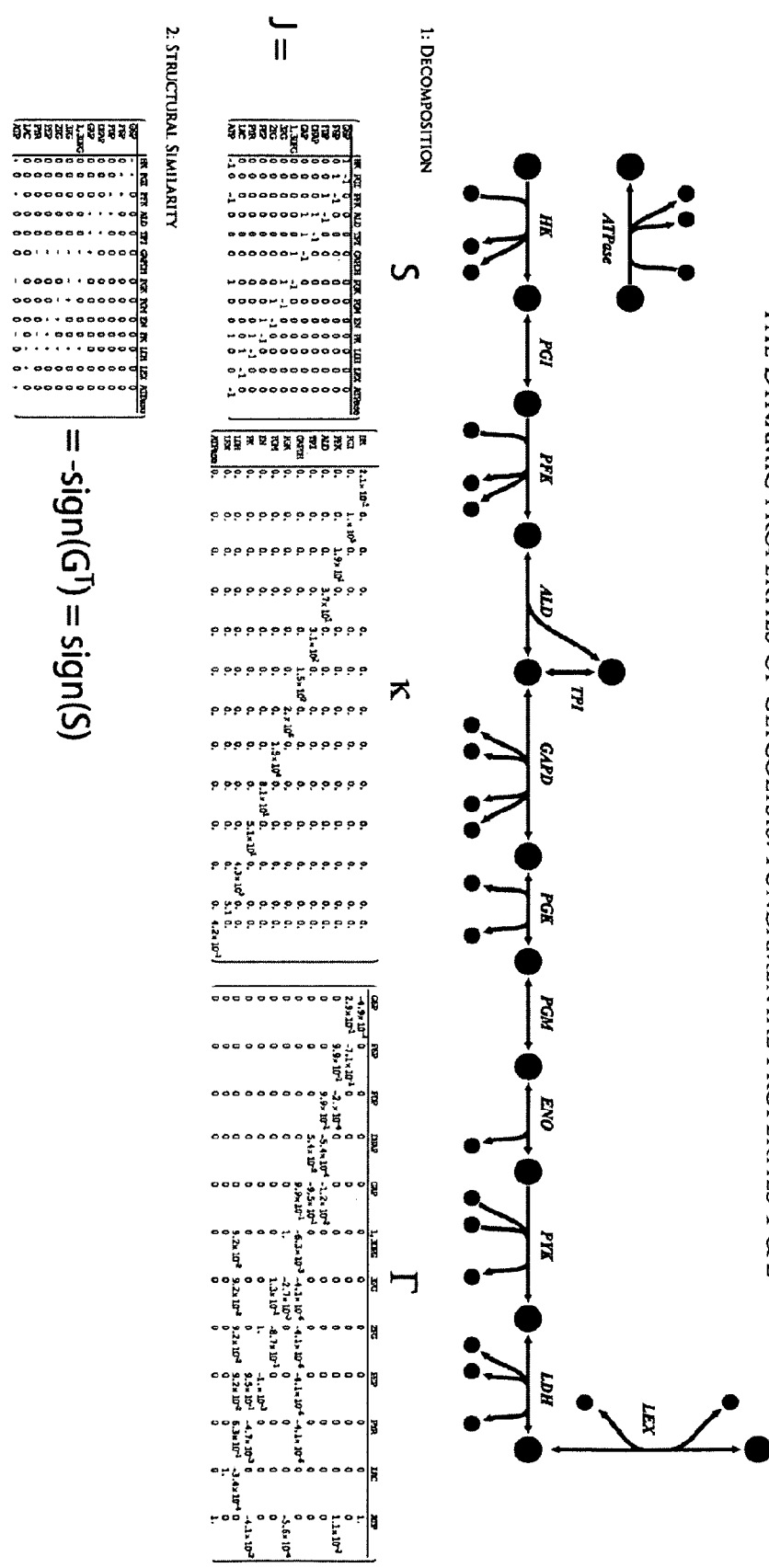
FIG. 3A shows an example of the glycolytic pathway in *Homo sapiens*. A reaction map of the glycolytic pathway is shown. The decomposition of the Jacobian ($J_x$) into the stoichiometric, κ, and Γ matrices follows below (1-norm used for the factorization of F). The negative transpose of the gradient matrix is shown directly below the stoichiometric matrix, demonstrating the structural similarity.

The glycolytic pathway (FIG. 3A) can be used to illustrate this and the properties below. A full kinetic model of red cell metabolism (Jamshidi et al., 2001) is available and the stoichiometric and gradient matrices are readily obtained for its glycolytic pathway. G can be factored into $\kappa$ and $\Gamma$ (FIG. 3A). The elements in K are spread over approximately ten (log $[\kappa_{max}/\kappa_{min}]=9.7$) orders of magnitude. The matrix S is universal and so are the elements of G for a given set of physico-chemical conditions, such as temperature It follows from Equation (2) that if $s_{ij}=0$ then $g_{ji}$ is also zero; that is if a compound does not participate in a reaction, it has no kinetic effect on it. Conversely, if $s_{ij} \neq 0$ then $g_{ji}$ is also not zero. Further inspection reveals the property that S is structurally similar to $-G^T$ as illustrated in FIG. 1.B.2. Thus, the non-zero entries in S have corresponding non-zero elements in $-G^T$, but with a different numerical value. This fundamental feature shows that the topology of the network as reflected in S has a dominant effect on its dynamic features; providing another example of the biological principle that structure has a dominant effect on function.

The duality relationship illustrates that fluxes or concentrations can be used as the independent variables: A flux deviation variable, v' can be defined such that $v'=G \cdot x'$, from which it follows that $$dv'/dt = G \cdot S \cdot T' = J_v \cdot v' \quad (5)$$

This transformation illustrates the switch from concentrations to fluxes as the independent variables. Fluxes can tie together the multiple parts of a network to form its overall functions. Furthermore, the ability to relate the fluxes and concentrations independently of a specific rate law formulation, if the elements of G can be approximated, has significant implications for the construction and analysis of kinetic networks.

The two Jacobian matrices, $G \cdot S$ and $S \cdot G$, are similar and share eigenvalues. Equation (5) is the 'dynamic' flux balance equation since the variables in it are the fluxes, v'. One can thus analyze network properties either in terms of concentrations or fluxes as illustrated within FIG. 1.B.3. The fluxes are 'network' variables, as they tie all the components together, while the concentrations are 'component' variables.

The properties of the Jacobian matrix that determine the characteristics of the network dynamics are its eigen-properties. The eigenvalues are network-based time constants (in contrast to the reaction based time constants in $\kappa$). Formally, the standard eigen-analysis is performed by the diagonalization of the Jacobian matrix as:

$$J = M \cdot \Lambda \cdot M^{-1} \quad (6)$$

where M is the matrix of eigenvectors, $\Lambda$ is a diagonal matrix of the eigenvalues, and $M^{-1}$ is the matrix of eigenrows. If the decomposition of equation (6) is introduced into equation (3) we obtain differential equations for the modes ($m = M^{-1} \cdot x'$)

$$dm/dt = \Lambda \cdot m, \text{ or } dm_i/dt = \lambda_i \cdot m_i, \text{ or } m_i(t) = m_{i,0} \exp(\lambda_i t) \quad (7)$$

or a set of completely decoupled dynamic variables; that is, each $m_i$ moves on it own time scale defined by $\lambda_i$ independent of all the other $m_j$. The eigenrows give lumped or aggregate variables that move independently on each time scale since m is a set of dynamically independent variables. The eigenvectors form a natural coordinate system to describe the dynamics motion of the modes. We note that this decomposition can be applied to J or $J_v$ (FIG. 3B.4). The eigenvalues will be the same whereas the eigenvectors and eigenrows will differ since the variable sets (concentrations vs. fluxes) will not be the same.

The distribution of the numerical values of the eigenvalues is the basis for time scale separation. Time scale separation forms the basis for decomposition of biochemical reaction networks in time and the interpretation of the biochemical events that take place on the various time constants. Time scale separation has been analyzed in the context of biological networks and shown to lend insight and enable the simplification of theses networks (Heinrich and Sonntag, 1982; Paisson et al., 1987; Reich and Selkov, 1981, which are all incorporated by reference in their entireties).

Methods described herein enable the explicit construction of kinetic models using the incorporation of different data types. The properties, completeness, and accuracy of the data can be explicitly traced to dynamic properties. This decomposition will not only tie the models directly back to the data, but also explicitly gives us the parts of the model that are under biological control and subject to change with adaptation or evolution. Measurement uncertainties are primarily in κ and are subject to evolutionary changes. These 'biological' design parameters will likely need to be dealt with through the use of methods that bracket the range of values within uncertainty limitations.

Embodiments show how data can be used for the full delineation of the chemical equations that make up a network and ideally their representation as net combinations of elementary reactions (i.e. $v_{net}=v^+ - v^-$). In this format the structure of the gradient matrix can be determined, but integration of multiple networks is also possible and the explicit analysis of the effects of regulatory molecules is also enabled. Furthermore, the underlying bilinear kinetic nature of network dynamics is explicitly recognized by embodiments disclosed herein, as all chemical reactions are combinations of bilinear interactions, including regulatory processes (Segel, 1975).

The duality between flux distributions and concentration distributions enabled by the transformations of the data matrices, G·S and S·G allows representation of network kinetics in terms of concentration variables or flux variables. The systems biology paradigm of 'components→networks→computational→models→physiological states' naturally leads to the use of fluxes as variables to characterize the functional states of a network. Fluxomic data ties components in a network together and is interpreted through network models, whereas concentration data is component data. Fluxes have been widely used for steady state analysis and can now be used to study dynamic states as well.

Time scale decomposition has been known and studied for several decades (Heinrich et al., 1977; Heinrich and Sonntag, 1982; Palsson et al., 1987; Reich and Selkov, 1981, which are all hereby incorporated by reference in their entireties). Such studies have primarily been performed for small-scale models today, but their conceptual foundation has been established. At larger scales, new issues will arise. These are likely to include, data sensitivity, course-graining and modularization of physiological functions in time. New methods to study the bases vectors in M and $M^{-1}$ that directly relate them to biochemistry and physiological functions need to be established. The promise of the elucidation of (dynamic) structure-(physiological) function relationships (Palsson et al., 1987, which is hereby incorporated by reference in its entirety) may now grow to large-scale networks.

As an example, models derived by methods disclosed herein can be used to determine the effects of changes from aerobic to anaerobic conditions, such as occurs in skeletal muscles during exercise or in tumors, or to determine the effect of various dietary changes. These modes can also be used to determine the dynamics and consequences of genetic defects, such as deficiencies in metabolic enzymes such as phosphofructokinase, phosphoglycerate kinase, phosphoglycerate mutase, lactate dehydrogenase and adenosine deaminase. As another example, the dynamics and consequences of defects in metabolic transporters, such as ABC transporters, the SLC class of transporters, as well as the cytochrome P450 class of enzymes, may be determined.

The kinetic network models can also be used to choose appropriate targets for drug design in individuals or groups of individuals. Such targets include genes, proteins or reactants, which when modulated positively or negatively in a simulation produce a desired therapeutic result. Models and methods disclosed herein can also be used to predict the effects of a therapeutic agent or dietary supplement on a cellular function of interest. Likewise, models and methods can be used to predict both desirable and undesirable side effects of the therapeutic agent on an interrelated cellular function in the target cell, as well as the desirable and undesirable effects that may occur in other cell types. Thus, models and methods disclosed herein can make the drug development process more rapid and cost effective than is currently possible.

The kinetic models can be used to develop individualized drug therapies and doses. Measuring a set of fluxes and concentrations in an individual before and after giving a dose of a therapeutic agent to the individual and constructing kinetic network models according to the measured data specific to the individual can be constructed. Analysis of the dynamic and functional properties of the individual specific network can be used to determine whether the therapeutic agent is effective in the desired outcome and the appropriate dose ranges if applicable.

As used herein, the term reaction is intended to mean a conversion that consumes a substrate or forms a product that occurs in a biological network. The term can include a conversion that occurs due to the activity of one or more enzymes that are genetically encoded by the human genome. The term can also include a conversion that occurs spontaneously in a cell, such as in human or mammal. Conversions included in the term include, for example, changes in chemical composition such as those due to nucleophilic or electrophilic addition, nucleophilic or electrophilic substitution, elimination, isomerization, deamination, phosphorylation, methylation, glycolysation, reduction, oxidation or changes in location such as those that occur due to a transport reaction that moves one or more reactants within the same compartment or from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term reaction is intended to mean a chemical that is a substrate or a product of a reaction that occurs in a biological network. The term can include substrates or products of reactions performed by one or more enzymes encoded by human gene(s), reactions occurring in cells that are performed by one or more non-genetically encoded macromolecule, protein or enzyme, or reactions that occur spontaneously in a cell. Metabolites are understood to be reactants within the meaning of the term. It will be understood that when used in reference to an in silico model or data structure, a reactant is intended to be a representation of a chemical that is a substrate or a product of a reaction that occurs in a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to reactions or reactants is intended to mean at least 2 reactions or reactants. The term can include any number of reactions or reactants in the range from 2 to the number of naturally occurring reactants or reactions for a particular cell. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell such as at least 20%, 30%, 50%, 60%, 75%, 90%, 95% or 98% of the total number of naturally occurring reactions that occur in the particular cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, a stoichiometric coefficient, a rate constant, a gradient matrix coefficient, a gamma matrix coefficient, or a Jacobian matrix coefficient.

As used herein, the term "constraint", reaction constraint, or flux constraint is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer and non-integer. Alternatively, a boundary can be a variable boundary value as set forth below.

As used herein, the term "concentration constraint" is intended to mean an upper and lower boundary for the concentration of a metabolite or chemical species in a biological network. The boundary can specify the amount of mass or number of moles, or number of molecules per unit volume. This may be within a tissue, a sample of biological fluid, a cell, a subcompartment of a cell, or another confined quantity. The boundary is a non-negative real number including zero, integers, and non-integers. Alternatively, a boundary for a concentration constraint can be a variable boundary as set forth below, with the stipulation that negative values are not permitted.

As used herein, the term "kinetic constraint" is intended to mean an upper and lower boundary for the kinetic constant for a reaction in a biological network. The boundary can specify the time constant characteristic of a particular reaction or set of reactions. The physical units are [concentration]$^{-n+1}$ where n is the kinetic order of the corresponding reaction. For example, a zero order, first order, and second order kinetic constant has units [concentration]*time$^{-1}$, time$^{-1}$, and concentration$^{-1}$*time$^{-1}$ respectively. The boundary is a non-negative real number including zero, integers, and non-integers. Alternatively, a boundary for a concentration constraint can be a variable boundary as set forth below, with the stipulation that negative values are not permitted.

As used herein, the term "equilibrium constant constraint" is intended to mean an upper and lower boundary for the equilibrium constant for a reaction in a biological network. The boundary can specify the equilibrium constant of a particular reaction or set of reactions. The boundary is a non-negative real number including zero, integers, and non-integers. Alternatively, a boundary for a concentration constraint can be a variable boundary as set forth below, with the stipulation that negative values are not permitted.

As defined herein, the term "uniquely defined constraint" is intended to mean a constraint whose lower bound is equal in value to the upper bound.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "constraint set" refers to the collection of flux, concentration, and equilibrium constraints for a biological network. Constraint sets for kinetic constants may be found by solving a steady state mass conservation relationship comprising a stoichiometric matrix and flux vector.

As used herein, the term "allosteric regulation" refers to the regulation of a protein or enzyme by a molecule that binds to a site other than the primary active site, thereby altering the activity of the enzyme and the corresponding reaction that it regulates.

As used herein, the term "activate" or activation refers to an effect a compound has on another compound, serving to alter the constraints in a positive manner, such as increasing the activity of a reaction. This includes but is not limited to allosteric and non-allosteric regulation of enzymes.

As used herein, the term "inhibit" or inhibition refers to an effect a compound has on another compound, serving to alter the constraints in a negative manner, such as decreasing the activity of a reaction. This includes but is not limited to allosteric and non-allosteric regulation of enzymes.

As used herein, the term "growth" refers to the production of a weighted sum of metabolites identified as biomass components.

As used herein, the term "energy production" refers to the production of metabolites that store energy in their chemical bonds, particularly high energy phosphate bonds such as ATP and GTP.

As used herein, the term "redox equivalent" refers to a metabolite that can alter the oxidation state of other metabolites, generally through the transfer of electrons and or protons.

As used herein, the term "biomass" refers to a set of metabolites that are required for cellular functions including replication, maintenance, and/or survival. As such, the term "biomass precursor" refers to a metabolite that can be converted to or is a member of the class of biomass metabolites.

As used herein, the term "bioactive small molecule" refers to a metabolite that can inhibit or activate another biological compound, including metabolites, proteins, and nucleic acid polymers.

As used herein, the term "cofactor" refers to a metabolite or chemical compound that is required for a catalytic activity of an enzyme to be carried out.

As used herein, the term "optimization problem" refers to a problem whose solution is obtained through the calculation of a minimum (or maximum) value of the objective function.

As used herein, the term "objective function" refers to a physiological function that can be described in terms of the data structure of a network, generally in terms of one or more weighted sum or product of reactions.

Methods and models disclosed herein can be applied to any *H. sapiens* cell type at any stage of differentiation, including, for example, embryonic stem cells, hematopoietic stem cells, differentiated hematopoietic cells, skeletal muscle cells, cardiac muscle cells, smooth muscle cells, skin cells, nerve cells, kidney cells, pulmonary cells, liver cells, adipocytes and endocrine cells (e.g., beta islet cells of the pancreas, mammary gland cells, adrenal cells, and other specialized hormone secreting cells).

Methods and models disclosed herein can be applied to normal cells or pathological cells. Normal cells that exhibit a variety of physiological activities of interest, including homeostasis, proliferation, differentiation, apoptosis, contraction and motility, can be modeled. Pathological cells can also be modeled, including cells that reflect genetic or developmental abnormalities, nutritional deficiencies, environmental assaults, infection (such as by bacteria, viral, protozoan or fungal agents), neoplasia, aging, altered immune or endocrine function, tissue damage, or any combination of these factors. The pathological cells can be representative of any type of mammalian, primate or non-primate pathology, including, for example, various metabolic disorders of carbohydrate, lipid or protein metabolism, obesity, diabetes, cardiovascular disease, fibrosis, various cancers, kidney failure, immune pathologies, neurodegenerative diseases, and various monogenetic diseases described found in humans and documented in the Online Mendelian Inheritance in Man database (Center for Medical Genetics, Johns Hopkins University (Baltimore, Md.) and National Center for Biotechnology Information, National Library of Medicine (Bethesda, Md.).

Methods and models disclosed herein can also be applied to cells undergoing therapeutic perturbations, such as cells treated with drugs that target participants in a reaction network, cells treated with gene-based therapeutics that increase or decrease expression of an encoded protein, and cells treated with radiation. As used herein, the term "drug" refers to a compound of any molecular nature with a known or proposed therapeutic function, including, for example, small molecule compounds, peptides and other macromolecules, peptidomimetics and antibodies, any of which can optionally be tagged with cytostatic, targeting or detectable moieties. The term "gene-based therapeutic" refers to nucleic acid therapeutics, including, for example, expressible genes with normal or altered protein activity, antisense compounds, ribozymes, DNAzymes, RNA interference compounds (RNAi) and the like. The therapeutics can target any reaction network participant, in any cellular location, including participants in extracellular, cell surface, cytoplasmic, mitochondrial and nuclear locations. Experimental data that are gathered on the response of cells to therapeutic treatment, such as alterations in gene or protein expression profiles, can be used to tailor a network for a pathological state of a particular cell type.

Methods and models disclosed herein can be applied to *H. sapiens* cells as they exist in any form, such as in primary cell isolates or in established cell lines, or in the whole body, in intact organs or in tissue explants. Accordingly, the methods and models can take into account intercellular communications and/or inter-organ communications, the effect of adhesion to a substrate or neighboring cells (such as a stem cell interacting with mesenchymal cells or a cancer cell interacting with its tissue microenvironment, or beta-islet cells without normal stroma), and other interactions relevant to multicellular systems.

The reactants to be used in a reaction network data structure of the invention can be obtained from or stored in a compound database. As used herein, the term "compound database" is intended to mean a computer readable medium containing a plurality of molecules that includes substrates and products of biological reactions. The plurality of molecules can include molecules found in multiple organisms, thereby constituting a universal compound database. Alternatively, the plurality of molecules can be limited to those that occur in a particular organism, thereby constituting an organism-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space; the interior space of an organelle such as a mitochondrium, endoplasmic reticulum, Golgi apparatus, vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of biological reactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus, a reaction that simply transports a metabolite from the extracellular environment to the cytosol, without changing its chemical composition is solely classified as a translocation, while a reaction such as the phosphotransferase system (PTS) which takes extracellular glucose and converts it into cytosolic glucose-6-phosphate is a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on a cell. While they may be chemically balanced in certain cases, they are typically not balanced and can often have only a single substrate or product. As a matter of convention the exchange reactions are further classified into demand exchange and input/output exchange reactions.

Input/output exchange reactions are used to allow extracellular reactants to enter or exit the reaction network represented by a model of the invention. For each of the extracellular metabolites a corresponding input/output exchange reaction can be created. These reactions can either be irreversible or reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reaction can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Depending upon the particular environmental conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in a particular cell or that are desired to simulate the activity of the full set of reactions occurring in the particular human cell.

A reaction network data structure or index of reactions used in the data structure such as that available in a metabolic reaction database, as described herein, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction or Gene Ontology (GO) number of the particular metabolic reaction, a subset of reactions to which the reaction belongs, citations to references from which information was obtained, or a level of confidence with which a reaction is believed to occur in a particular human cell. A computer readable medium of the invention can include a gene database containing annotated reactions. Such information can be obtained during the course of building a metabolic reaction database or model of the invention as described below.

Thus, a method is provided for making or expanding a data structure relating a plurality of H. sapiens reactants to a plurality of H. sapiens reactions in a computer readable medium. The method includes the steps of: (a) identifying a plurality of H. sapiens reactions and a plurality of H. sapiens reactants that are substrates and products of the H. sapiens reactions; (b) relating the plurality of H. sapiens reactants to the plurality of H. sapiens reactions in a data structure, wherein each of the H. sapiens reactions includes one or more reactants identified as a substrate of the reaction, one or more reactants identified as a product of the reaction and a stoichiometric coefficient relating the substrate and the product; (c) making a constraint set for the plurality of H. sapiens reactions; (d) providing an objective function; (e) determining at least one flux distribution that minimizes or maximizes the objective function when the constraint set is applied to the data structure, (f) if at least one flux distribution is not predictive of human physiology, then adding a reaction to or deleting a reaction from the data structure and repeating step (e), and (g) if at least one flux distribution is predictive of human physiology, then storing the data structure in a computer readable medium.

The majority of the reactions occurring in human reaction networks are catalyzed by enzymes/proteins, which are created through the transcription and translation of the genes found on the chromosome(s) in the cell. The remaining reactions occur through non-enzymatic processes. Furthermore, a reaction network data structure can contain reactions that add or delete steps to or from a particular reaction pathway. For example, reactions can be added to optimize or improve performance of a H. sapiens model in view of empirically observed activity. Alternatively, reactions can be deleted to remove intermediate steps in a pathway when the intermediate steps are not necessary to model flux through the pathway. For example, if a pathway contains three nonbranched steps, the reactions can be combined or added together to give a net reaction, thereby reducing memory required to store the reaction network data structure and the computational resources required for manipulation of the data structure.

A reaction network data structure as described herein can be used to determine the activity of one or more reactions in a plurality of H. sapiens reactions independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that are not protein-enabled reactions. Furthermore, the occurrence of a particular reaction in a cell for which no associated proteins or genetics have been currently identified can be indicated during the course of model building by the iterative model building methods as disclosed herein.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., J. Theor. Biol. 203:249-283 (2000), which is hereby incorporated by reference in its entirety. The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem, which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

Flux constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Of particular importance in the regulation of human cell types is the implementation of paracrine and endocrine signaling pathways to control cellular activities. In these cases a cell secretes signaling molecules that may be carried far afield to act on distant targets (endocrine signaling), or act as local mediators (paracrine signaling). Examples of endocrine signaling molecules include hormones such as insulin, while examples of paracrine signaling molecules include neurotransmitters such as acetylcholine. These molecules induce cellular responses through signaling cascades that affect the activity of biochemical reactions in the cell. Regulation can be represented in an in silico *H. sapiens* model by providing a variable constraint.

The methods described herein can be implemented on any conventional host computer system, such as those based on Intel® or AMD® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN or COBOL and compiled using any well-known compatible compiler. The software of the invention normally runs from instructions stored in a memory on a host computer system. A memory or computer readable medium can be a hard disk, floppy disc, compact disc, DVD, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

The data matrices constructed by the methods described in this invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, *Learning XML* O'Reilly and Associates, Sebastopol, Calif. (2001).

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to human physiology. Also, the user interface can display a graphical representation of a reaction network or the results of a simulation using a model of the invention.

Once an initial reaction network data structure and set of constraints has been created, a model disclosed herein can be tested by preliminary simulation. During preliminary simulation, gaps in the network or "dead-ends" in which a metabolite can be produced but not consumed or where a metabolite can be consumed but not produced can be identified. Based on the results of preliminary simulations areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage an existing model may be subjected to a series of functional tests to determine if it can perform basic requirements such as the ability to produce the required biomass constituents and generate predictions concerning the basic physiological characteristics of the particular organism strain being modeled. The more preliminary testing that is conducted, typically, the higher the quality of the model that will be generated. Typically the majority of the simulations used in this stage of development will be single optimizations. A single optimization can be used to calculate a single flux distribution demonstrating how metabolic resources are routed determined from the solution to one optimization problem. An optimization problem can be solved using linear programming as demonstrated in the Examples below. The result can be viewed as a display of a flux distribution on a reaction map. Temporary reactions can be added to the network to determine if they should be included into the model based on modeling/simulation requirements.

Once a model is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a as a modal matrix.

Figure 6:
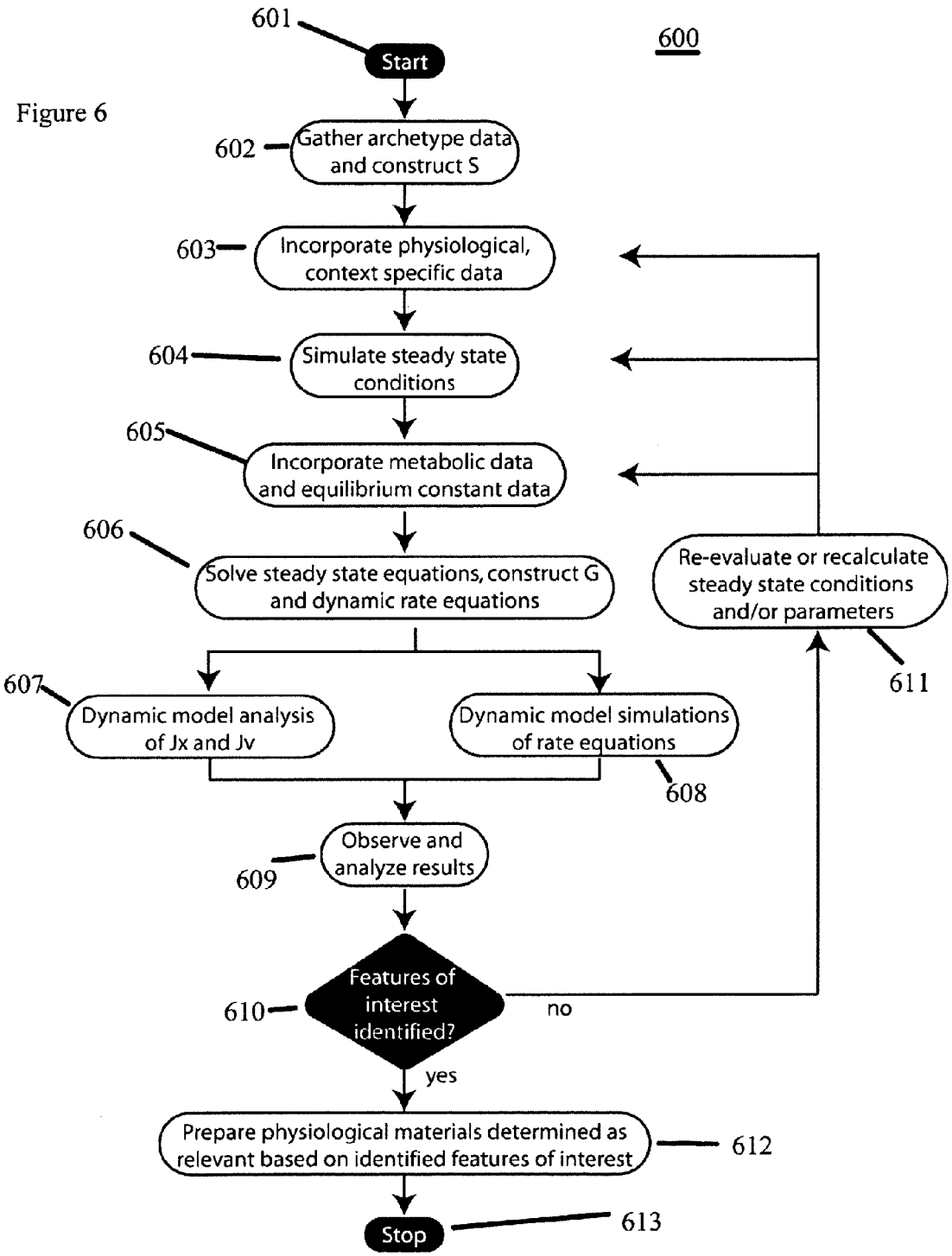
FIG. 6 is a block diagram of the general diagnostic and therapeutic methodologies implementing one embodiment of the invention.
Figure 7:
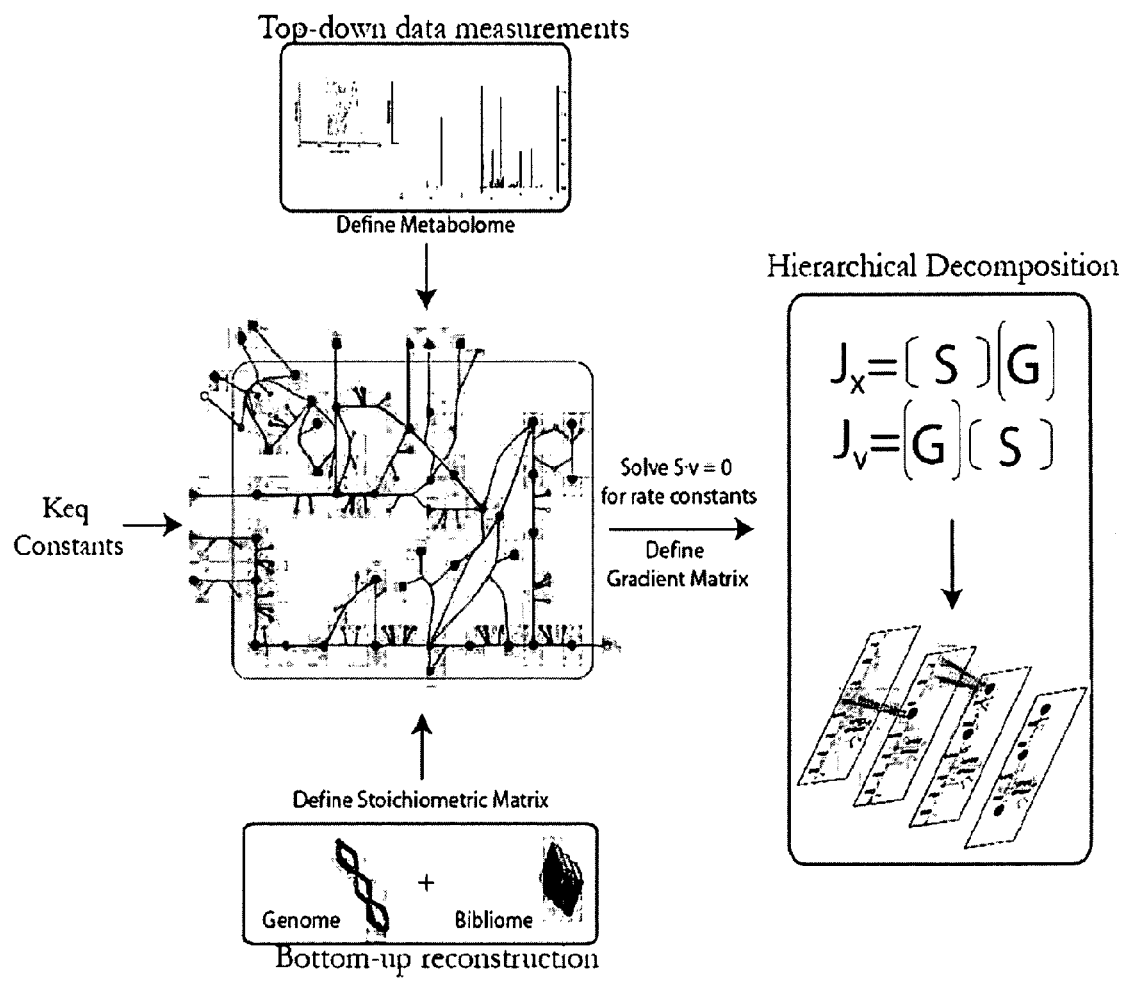
FIG. 7 is a generalized flow diagram of one embodiment of the invention.

FIG. 6 is a block diagram of some contemplated therapeutic and diagnostic embodiments of the invention employing the model. Diagnostic or therapeutic analysis 600 begins 601 by first gathering the archetype data 602 for the domain under investigation and constructing S using this data. One skilled in the art will readily recognize numerous data sets that are available for a given domain. For example, in the domain of drug therapy identification, archetypical data may comprise statistical and theoretical information regarding the reactions under investigation. Physical and context specific data is then incorporated 603. Physical and context specific data may comprise the metabolomic characteristics common to a patient demographic under investigation. The model is then used to simulate steady state conditions 604. Once the steady state is achieved, metabolic data and equilibrium constant data are incorporated 605. The steady state equations are again solved for, and the matrix G and the dynamic rate equations are derived 606. At this point, the dynamic model provides an analysis of Jx and Jv 607 or simulations of the rate equations 608. The modeled dynamics are observed 609 and features of interest identified 610. One skilled in the art will recognize that features of interest will depend on the domain under investigation and metabolic pathway being studied. For example, for diagnostic purposes, particular fluxes or concentrations whose variation produces novel and unexpected behavior in the metabolic pathway may be considered features of interest.

If no features are observed, or further analysis is required, parameters or steady state conditions are modified in the model 611 so as to simulate a different dynamic, and the simulation 604 observed again until features of interest may be identified.

Alternatively, where features of interest have been identified, physiological materials relevant to them may be prepared 612 and the process completes 613. In the domain of drug therapy, for example, the preparation of physiological materials may comprise the identification and synthesis of compounds which will generate the desired metabolic behavior responsible for generating the features of interest previously modeled. One skilled in the art, however, will readily recognize that the model will lend itself to a wide variety of domains requiring a comprehensive understanding of large and complex metabolic pathways. Accordingly, the information derived from the model may be used in numerous physical applications, from confirming disease diagnosis, to identifying environmental factors impacting individual health.

Thus, methods provided herein can predict physiological function. In one embodiment, a method is provided, the method including providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product; providing a constraint set for the plurality of *H. sapiens* reactions; providing an objective function, and determining at least one flux distribution that minimizes or maximizes the objective function when the constraint set is applied to the data structure, thereby predicting a *H. sapiens* physiological function.

As used herein, the term "physiological function," when used in reference to *H. sapiens*, is intended to mean an activity of a human cell as a whole. An activity included in the term can be the magnitude or rate of a change from an initial state of a human cell to a final state of the human cell. An activity can be measured qualitatively or quantitatively. An activity included in the term can be, for example, growth, energy production, redox equivalent production, biomass production, development, or consumption of carbon, nitrogen, sulfur, phosphate, hydrogen or oxygen. An activity can also be an output of a particular reaction that is determined or predicted in the context of substantially all of the reactions that affect the particular reaction in a human cell or substantially all of the reactions that occur in a human cell. Examples of a particular reaction included in the term are production of biomass precursors, production of a protein, production of an amino acid, production of a purine, production of a pyrimidine, production of a lipid, production of a fatty acid, production of a cofactor, production of a hormone, production of a bioactive small molecule, or transport of a metabolite. A physiological function can include an emergent property which emerges from the whole but not from the sum of parts where the parts are observed in isolation (see for example, Palsson *Nat. Biotech* 18:1147-1150 (2000)).

A physiological function of *H. sapiens* reactions can be determined using dynamic phase plane analysis.

A physiological function of *H. sapiens* reactions can also be determined using a reaction map to display a flux distribution. A reaction map can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

Methods disclosed herein can be used to determine the activity of a plurality of *H. sapiens* reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite and metabolism of an alternative carbon source.

Methods disclosed herein can be used to determine a phenotype of a *H. sapiens* mutant. The activity of one or more *H. sapiens* reactions can be determined using the methods described above, wherein the reaction network data structure lacks one or more gene-associated reactions that occur in *H. sapiens*. Alternatively, methods can be used to determine the activity of one or more *H. sapiens* reactions when a reaction that does not naturally occur in *H. sapiens* is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from *H. sapiens*. The methods can be particularly useful for determining the effects of adding or deleting a gene that encodes for a gene product that performs a reaction in a peripheral metabolic pathway. In one contemplated embodiment, adenovirus vectors are used for in vivo transfer of genes determined in silico to be required for a desired functioning of the metabolic pathway.

A drug target or target for any other agent that affects human cellular function can be predicted using the methods of the invention. Such predictions can be made by removing a reaction to simulate total inhibition or prevention by a drug or agent. Alternatively, partial inhibition or reduction in the activity a particular reaction can be predicted by performing the methods with altered constraints. The methods can be particularly useful for identifying a target in a peripheral metabolic pathway.

Once a reaction has been identified for which activation or inhibition produces a desired effect on *H. sapiens* function, an enzyme or macromolecule that performs the reaction in *H. sapiens* or a gene that expresses the enzyme or macromolecule can be identified as a target for a drug or other agent. A candidate compound for a target identified by the methods of the invention can be isolated or synthesized using known methods. Such methods for isolating or synthesizing compounds can include, for example, rational design based on known properties of the target (see, for example, Decamp et al., *Protein Engineering Principles and Practice*, Ed. Cleland and Craik, Wiley-Liss, New York, pp. 467-506 (1996), which is hereby incorporated by reference in its entirety), screening the target against combinatorial libraries of compounds (see for example, Houghten et al., Nature, 354, 84-'86 (1991); Dooley et al., *Science*, 266, 2019-2022 (1994), which describe an iterative approach, or R. Houghten et al. PCT/US91/08694 and U.S. Pat. No. 5,556,762 which describe the positional scanning approach, all four of which are hereby incorporated by reference in their entireties), or a combination of both to obtain focused libraries. Those skilled in the art will know or will be able to routinely determine assay conditions to be used in a screen based on properties of the target or activity assays known in the art.

A candidate drug or agent, whether identified by methods described above or by other methods known in the art, can be validated using an in silico human metabolic model or method disclosed herein. The effect of a candidate drug or agent on human physiological function can be predicted based on the activity for a target in the presence of the candidate drug or agent measured in vitro or in vivo. This activity can be represented in an in silico human metabolic model by adding a reaction to the model, removing a reaction from the model or adjusting a constraint for a reaction in the model to reflect the measured effect of the candidate drug or agent on the activity of the reaction. By running a simulation under these conditions the holistic effect of the candidate drug or agent on human physiological function can be predicted.

Once a candidate has been identified, medical practitioners may readily conceive a plurality of delivery methods that will induce the desired simulated metabolic change. Suitable pharmaceutically acceptable carriers and their formulation are described in standard formulation treatises, e.g. *Remington's Pharmaceuticals Sciences* by E. W. martin. See also Wang, Y. J. and Hanson, M. A. "Parental formulations of Proteins and Peptides; Stability and Stabilizers," *Journals of Parental Sciences and Technology*, Technical Report No. 10, Supp. 42:2 S (1988).

The methods of the invention can be used to determine the effects of one or more environmental components or conditions on an activity of a *H. sapiens* cell. As set forth above, an exchange reaction can be added to a reaction network data structure corresponding to uptake of an environmental component, release of a component to the environment, or other environmental demand. The effect of the environmental component or condition can be further investigated by running simulations with adjusted values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a *H. sapiens* cell can be taken up and metabolized. The environmental component can also be a combination of components present for example in a minimal medium composition. Thus, methods disclosed herein can be used to determine an optimal or minimal medium composition that is capable of supporting a particular activity of *H. sapiens*.

In some embodiments, a method for determining a set of environmental components to achieve a desired activity for *H. sapiens* is provided. The method includes the steps of providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product; providing a constraint set for the plurality of *H. sapiens* reactions; applying the constraint set to the data representation, thereby determining the activity of one or more *H. sapiens* reactions; determining the activity of one or more *Homo sapiens* reactions according to steps (a) through (c), wherein the constraint set includes an upper or lower bound on the amount of an environmental component, and repeating steps (a) through (c) with a changed constraint set, wherein the activity determined.

Further contemplated embodiments comprise down-regulating portions of metabolic networks by introducing inhibiting compounds regulating flows found in the model. These compounds may inhibit deleterious feedback systems, such as by suppressing antigen processing or antigen presentation. Other embodiments may up-regulate portions of metabolic networks to account for deletions or omissions in preceding stages of a "normally" functioning network. Such pathways need not be confined to *H. sapiens* but can be used in foreign entities as well. For example, metabolic pathways in viruses and bacteria can be modeled to determine an exogenous chemical dependency which will permit the virus' live introduction into a host, and subsequent controlled attenuation via reduction of the chemical dependency. Such live introduction facilitates better immune response. Embodiments of the present invention, by modeling the metabolic pathway, permit more controlled attenuation of these vectors, with less risk to the host.

One skilled in the art will readily recognize that these are but a few possible implementations of the invention and that many more exist.

The following examples are intended to illustrate but not limit the invention.

Example 1

A Stoichiometric Model of Glycolysis in *Homo sapiens*

The stoichiometric matrix as described in this invention was constructed for the glycolytic pathway in *Homo sapiens*.

TABLE 1B

The stoichiometric matrix for the glycolytic pathway, the columns corresopnd to metabolites and columns corresopnd to fluxes.

TABLE 1

The stoichiometric matrix for the glycolytic pathway, the columns correspond to metabolites and columns correspond to fluxes.

|  | HK | PGI | PFK | ALD | TPI | GAPDH | PGK | PGM | EN | PK | LDH | LEX | ATPase |
|---|---|---|---|---|---|---|---|---|---|---|---|---|---|
| G6P | 1 | −1 | 0 | 0 | 0 | 0 | 0 | 0 | 0 | 0 | 0 | 0 | 0 |
| F6P | 0 | 1 | −1 | 0 | 0 | 0 | 0 | 0 | 0 | 0 | 0 | 0 | 0 |
| FDP | 0 | 0 | 1 | −1 | 0 | 0 | 0 | 0 | 0 | 0 | 0 | 0 | 0 |
| DHAP | 0 | 0 | 0 | 1 | −1 | 0 | 0 | 0 | 0 | 0 | 0 | 0 | 0 |
| GAP | 0 | 0 | 0 | 1 | 1 | −1 | 0 | 0 | 0 | 0 | 0 | 0 | 0 |
| DPG13 | 0 | 0 | 0 | 0 | 0 | 1 | −1 | 0 | 0 | 0 | 0 | 0 | 0 |
| PG3 | 0 | 0 | 0 | 0 | 0 | 0 | 1 | −1 | 0 | 0 | 0 | 0 | 0 |
| PG2 | 0 | 0 | 0 | 0 | 0 | 0 | 0 | 1 | −1 | 0 | 0 | 0 | 0 |
| PEP | 0 | 0 | 0 | 0 | 0 | 0 | 0 | 0 | 1 | −1 | 0 | 0 | 0 |
| PYR | 0 | 0 | 0 | 0 | 0 | 0 | 0 | 0 | 0 | 1 | −1 | 0 | 0 |

TABLE 1-continued

The stoichiometric matrix for the glycolytic pathway, the columns correspond to metabolites and columns correspond to fluxes.

|     | HK | PGI | PFK | ALD | TPI | GAPDH | PGK | PGM | EN | PK | LDH | LEX | ATPase |
|-----|----|-----|-----|-----|-----|-------|-----|-----|----|----|-----|-----|--------|
| LAC | 0  | 0   | 0   | 0   | 0   | 0     | 0   | 0   | 0  | 0  | 1   | −1  | 0      |
| ATP | −1 | 0   | −1  | 0   | 0   | 0     | 1   | 0   | 0  | 1  | 0   | 0   | −1     |

Example 2

The Gradient Matrix of Glycolysis in *Homo sapiens*

A model of glycolysis was constructed by the methods described in this invention. Fluxes and concentrations for a normal human red blood cell are listed in Table 2. Table 2 also includes equilibrium constants for the reactions in the network. Reactions with equilibrium constants much greater than 1 or much less than one are effectively irreversible. The gradient matrix can be factored into the kappa and gamma matrices as described in this invention and illustrated for the glycolytic pathway in *Homo sapiens*.

TABLE 2

The steady state concentrations of metabolites (mM: millimolar).

|       | Concentrations (mM) |
|-------|---------------------|
| G6P   | 0.066440083         |
| F6P   | 0.027233463         |
| FDP   | 0.013861036         |
| DHAP  | 0.147408623         |
| GAP   | 0.006698582         |
| DPG13 | 0.000228927         |
| PG3   | 0.083927674         |
| PG2   | 0.012267539         |
| PEP   | 0.020874113         |
| PYR   | 0.06                |
| LAC   | 1.397092049         |
| ATP   | 2.401613356         |

TABLE 3

The steady state fluxes and the equilibrium constants for the reactions in the glycolytic network (mM: millimolar, hr: hour, Keq: equilibrium constant).

|        | Flux (mM/hr)  | Keq       |
|--------|---------------|-----------|
| HK     | 0.498225636   | 1000      |
| PGI    | 0.498225611   | 0.41      |
| PFK    | 0.498225803   | 1000      |
| ALD    | 0.498225611   | 12.34568  |
| TPI    | 0.498225611   | 0.057143  |
| GAPDH  | 0.996253719   | 55.86592  |
| PGK    | −0.714792222  | 1800      |
| PGM    | 0.996451222   | 0.147059  |
| EN     | 0.996451222   | 1000      |
| PK     | 0.99270572    | 1000      |
| LDH    | 13.71530938   | 4464.286  |
| LEX    | 0.996451222   | 1         |
| ATPase | 0.996451975   | 1000      |

By solving the steady state mass balance equations using the stoichiometric matrix in Example 1 and the mass-action rate law formulation and substituting in steady state metabolite concentrations (Table 2), steady state flux concentrations (Table 3), and equilibrium constants (Table 3), the forward rate constants were calculated.

The mass-action rate laws were then written in terms of the equilibrium constants and rate constants, as function of the metabolite concentrations. The gradient matrix was calculated from this.

TABLE 4

The gradient matrix for the glycolytic pathway. Each element in the row is the partial derivative of the corresponding reaction with respect to the metabolite in the corresponding column.

|        | G6P       | F6P       | FDP       | DHAP      | GAP       | DPG13    |
|--------|-----------|-----------|-----------|-----------|-----------|----------|
| HK     | −0.000101 | 0         | 0         | 0         | 0         | 0        |
| PGI    | 29304.9   | −71475.36 | 0         | 0         | 0         | 0        |
| PFK    | 0         | 18.29651  | −0.003721 | 0         | 0         | 0        |
| ALD    | 0         | 0         | 36.15294  | −0.019616 | −0.43167  | 0        |
| TPI    | 0         | 0         | 0         | 16.50659  | −288.8654 | 0        |
| GAPDH  | 0         | 0         | 0         | 0         | 148.7583  | −0.94482 |
| PGK    | 0         | 0         | 0         | 0         | 0         | 2009588  |
| PGM    | 0         | 0         | 0         | 0         | 0         | 0        |
| EN     | 0         | 0         | 0         | 0         | 0         | 0        |
| PK     | 0         | 0         | 0         | 0         | 0         | 0        |
| LDH    | 0         | 0         | 0         | 0         | 0         | 39.25606 |
| LEX    | 0         | 0         | 0         | 0         | 0         | 0        |
| ATPase | 0         | 0         | 0         | 0         | 0         | 0        |

|        | PG3       | PG2       | PEP      | PYR      | LAC | ATP       |
|--------|-----------|-----------|----------|----------|-----|-----------|
| HK     | 0         | 0         | 0        | 0        | 0   | 0.207471  |
| PGI    | 0         | 0         | 0        | 0        | 0   | 0         |
| PFK    | 0         | 0         | 0        | 0        | 0   | 0.207582  |
| ALD    | 0         | 0         | 0        | 0        | 0   | 0         |
| TPI    | 0         | 0         | 0        | 0        | 0   | 0         |
| GAPDH  | −0.00061  | −0.00061  | −0.00061 | −0.00061 | 0   | 0         |
| PGK    | −5490.018 | 0         | 0        | 0        | 0   | −1133.834 |
| PGM    | 1959.931  | −13327.53 | 0        | 0        | 0   | 0         |

TABLE 4-continued

The gradient matrix for the glycolytic pathway. Each element in the row is the partial derivative of the corresponding reaction with respect to the metabolite in the corresponding column.

| | | | | | | |
|---|---|---|---|---|---|---|
| EN | 0 | 81.36511 | −0.081365 | 0 | 0 | 0 |
| PK | 0 | 0 | 48.23862 | −0.237211 | 0 | −2.067691 |
| LDH | 39.25606 | 39.25606 | 39.25606 | 271.2571 | −0.146556 | 0 |
| LEX | 0 | 0 | 0 | 0 | 5.055766 | 0 |
| ATPase | 0 | 0 | 0 | 0 | 0 | 0.415409 |

The structural similarity between the stoichiometric matrix and negative of the transpose of the gradient matrix for glycolysis is immediately apparent by comparing Table 1 and Table 4.

As discussed above, the gradient matrix can be factored into the kappa and gamma matrices as illustrated in Table 5 and Table 6.

TABLE 5

The kappa matrix which was constructed by factoring out the norms in the gradient matrix in Table 4. The 1-norm was used for this glycolytic kappa matrix.

| | | | | | | | |
|---|---|---|---|---|---|---|---|
| HK | 0.207572 | 0 | 0 | 0 | 0 | 0 | 0 |
| PGI | 0 | 100780.3 | 0 | 0 | 0 | 0 | 0 |
| PFK | 0 | 0 | 18.50781 | 0 | 0 | 0 | 0 |
| ALD | 0 | 0 | 0 | 36.60422 | 0 | 0 | 0 |
| TPI | 0 | 0 | 0 | 0 | 305.372 | 0 | 0 |
| GAPDH | 0 | 0 | 0 | 0 | 0 | 149.7056 | 0 |
| PGK | 0 | 0 | 0 | 0 | 0 | 0 | 2016211 |
| PGM | 0 | 0 | 0 | 0 | 0 | 0 | 0 |
| EN | 0 | 0 | 0 | 0 | 0 | 0 | 0 |
| PK | 0 | 0 | 0 | 0 | 0 | 0 | 0 |
| LDH | 0 | 0 | 0 | 0 | 0 | 0 | 0 |
| LEX | 0 | 0 | 0 | 0 | 0 | 0 | 0 |
| ATPase | 0 | 0 | 0 | 0 | 0 | 0 | 0 |

| | | | | | | |
|---|---|---|---|---|---|---|
| HK | 0 | 0 | 0 | 0 | 0 | 0 |
| PGI | 0 | 0 | 0 | 0 | 0 | 0 |
| PFK | 0 | 0 | 0 | 0 | 0 | 0 |
| ALD | 0 | 0 | 0 | 0 | 0 | 0 |
| TPI | 0 | 0 | 0 | 0 | 0 | 0 |
| GAPDH | 0 | 0 | 0 | 0 | 0 | 0 |
| PGK | 0 | 0 | 0 | 0 | 0 | 0 |
| PGM | 15287.46 | 0 | 0 | 0 | 0 | 0 |
| EN | 0 | 81.44648 | 0 | 0 | 0 | 0 |
| PK | 0 | 0 | 50.54352 | 0 | 0 | 0 |
| LDH | 0 | 0 | 0 | 428.4279 | 0 | 0 |
| LEX | 0 | 0 | 0 | 0 | 5.055766 | 0 |
| ATPase | 0 | 0 | 0 | 0 | 0 | 0.415409 |

TABLE 6

The gamma matrix corresponding to the kappa matrix in Table 5 and the gradient matrix in Table 4.

| G6P | F6P | FDP | DHAP | GAP | DPG13 | PG3 |
|---|---|---|---|---|---|---|
| −0.000488 | 0 | 0 | 0 | 0 | 0 | 0 |
| 0.29078 | −0.70922 | 0 | 0 | 0 | 0 | 0 |
| 0 | 0.988583 | −0.000201 | 0 | 0 | 0 | 0 |
| 0 | 0 | 0.987671 | −0.000536 | −0.011793 | 0 | 0 |
| 0 | 0 | 0 | 0.054054 | −0.945946 | 0 | 0 |
| 0 | 0 | 0 | 0 | 0.993673 | −0.006311 | −4.07E−06 |
| 0 | 0 | 0 | 0 | 0 | 0.996715 | −0.002723 |
| 0 | 0 | 0 | 0 | 0 | 0 | 0.128205 |
| 0 | 0 | 0 | 0 | 0 | 0 | 0 |
| 0 | 0 | 0 | 0 | 0 | 0.091628 | 0.091628 |
| 0 | 0 | 0 | 0 | 0 | 0 | 0 |
| 0 | 0 | 0 | 0 | 0 | 0 | 0 |

| PG2 | PEP | PYR | LAC | ATP |
|---|---|---|---|---|
| 0 | 0 | 0 | 0 | 0.999512 |
| 0 | 0 | 0 | 0 | 0 |

TABLE 6-continued

The gamma matrix corresponding to the kappa matrix
in Table 5 and the gradient matrix in Table 4.

| | | | | |
|---|---|---|---|---|
| 0 | 0 | 0 | 0 | 0.011216 |
| 0 | 0 | 0 | 0 | 0 |
| 0 | 0 | 0 | 0 | 0 |
| −4.07E−06 | −4.07E−06 | −4.07E−06 | 0 | 0 |
| 0 | 0 | 0 | 0 | −0.000562 |
| −0.871795 | 0 | 0 | 0 | 0 |
| 0.999001 | −0.000999 | 0 | 0 | 0 |
| 0 | 0.954398 | −0.004693 | 0 | −0.040909 |
| 0.091628 | 0.091628 | 0.633145 | −0.000342 | 0 |
| 0 | 0 | 0 | 1 | 0 |
| 0 | 0 | 0 | 0 | 1 |

The elements in the kappa matrix are spread over approximately ten (log $[\kappa_{max}/\kappa_{min}]=9.7$) orders of magnitude, which conveys the biologically important time scale hierarchy and also conveys the ill-conditioned properties of the gradient matrix.

Example 3

The Dynamic Glycolytic Pathway in *Homo sapiens*

Using the stoichiometric matrix in Example 1 and the gradient matrix in Example 2, a dynamic model of the glycolytic pathway was constructed by calculating the concentration Jacobian matrix by post-multiplication of the stoichiometric matrix by the gradient matrix (Table 7) and the flux Jacobian matrix by pre-multiplication of the stoichiometric matrix by the gradient matrix (Table 8), as per the methods described above.

TABLE 7

The concentration Jacobian matrix for the glycolytic pathway in
*Homo sapiens*. Row and column headings are labeled for clarity.

| | G6P | F6P | FDP | DHAP | GAP | DPG13 |
|---|---|---|---|---|---|---|
| G6P | −29304.9 | 71475.36 | 0 | 0 | 0 | 0 |
| F6P | 29304.9 | −71493.65 | 0.003721 | 0 | 0 | 0 |
| FDP | 0 | 18.29651 | −36.15666 | 0.019616 | 0.43167 | 0 |
| DHAP | 0 | 0 | 36.15294 | −16.52621 | 288.4337 | 0 |
| GAP | 0 | 0 | 36.15294 | 16.48698 | −438.0554 | 0.94482 |
| DPG13 | 0 | 0 | 0 | 0 | 148.7583 | −2009588 |
| PG3 | 0 | 0 | 0 | 0 | 0 | 2009588 |
| PG2 | 0 | 0 | 0 | 0 | 0 | 0 |
| PEP | 0 | 0 | 0 | 0 | 0 | 0 |
| PYR | 0 | 0 | 0 | 0 | 0 | −39.25606 |
| LAC | 0 | 0 | 0 | 0 | 0 | 39.25606 |
| ATP | 0.000101 | −18.29651 | 0.003721 | 0 | 0 | 2009588 |

| | PG3 | PG2 | PEP | PYR | LAC | ATP |
|---|---|---|---|---|---|---|
| G6P | 0 | 0 | 0 | 0 | 0 | 0.207471 |
| F6P | 0 | 0 | 0 | 0 | 0 | −0.207582 |
| FDP | 0 | 0 | 0 | 0 | 0 | 0.207582 |
| DHAP | 0 | 0 | 0 | 0 | 0 | 0 |
| GAP | 0.00061 | 0.00061 | 0.00061 | 0.00061 | 0 | 0 |
| DPG13 | 5490.017 | −0.00061 | −0.00061 | −0.00061 | 0 | 1133.834 |
| PG3 | −7449.948 | 13327.53 | 0 | 0 | 0 | −1133.834 |
| PG2 | 1959.931 | −13408.89 | 0.081365 | 0 | 0 | 0 |
| PEP | 0 | 81.36511 | −48.31998 | 0.237211 | 0 | 2.067691 |
| PYR | −39.25606 | −39.25606 | 8.982558 | −271.4943 | 0.146556 | −2.067691 |
| LAC | 39.25606 | 39.25606 | 39.25606 | 271.2571 | −5.202322 | 0 |
| ATP | −5490.018 | 0 | 48.23862 | −0.237211 | 0 | −1136.733 |

TABLE 8

The concentration Jacobian matrix for the glycolytic pathway in
*Homo sapiens*. Row and column headings are labeled for clarity.

|  | HK | PGI | PFK | ALD | TPI | GAPDH | PGK |
|---|---|---|---|---|---|---|---|
| HK | −0.207572 | 0.000101 | −0.207471 | 0 | 0 | 0 | 0.207471 |
| PGI | 29304.9 | −100780.3 | 71475.36 | 0 | 0 | 0 | 0 |
| PFK | −0.207582 | 18.29651 | −18.50781 | 0.003721 | 0 | 0 | 0.207582 |
| ALD | 0 | 0 | 36.15294 | −36.60422 | −0.412054 | 0.43167 | 0 |
| TPI | 0 | 0 | 0 | −272.3588 | −305.372 | 288.8654 | 0 |
| GAPDH | 0 | 0 | 0 | 148.7583 | 148.7583 | −149.7031 | 0.94421 |
| PGK | 1133.834 | 0 | 1133.834 | 0 | 0 | 2009588 | −2016211 |
| PGM | 0 | 0 | 0 | 0 | 0 | 0 | 1959.931 |
| EN | 0 | 0 | 0 | 0 | 0 | 0 | 0 |
| PK | 2.067691 | 0 | 2.067691 | 0 | 0 | 0 | −2.067691 |
| LDH | 0 | 0 | 0 | 0 | 0 | 39.25606 | 0 |
| LEX | 0 | 0 | 0 | 0 | 0 | 0 | 0 |
| ATPase | −0.415409 | 0 | −0.415409 | 0 | 0 | 0 | 0.415409 |

|  | PGM | EN | PK | LDH | LEX | ATPase |
|---|---|---|---|---|---|---|
| HK | 0 | 0 | 0.207471 | 0 | 0 | −0.207471 |
| PGI | 0 | 0 | 0 | 0 | 0 | 0 |
| PFK | 0 | 0 | 0.207582 | 0 | 0 | −0.207582 |
| ALD | 0 | 0 | 0 | 0 | 0 | 0 |
| TPI | 0 | 0 | 0 | 0 | 0 | 0 |
| GAPDH | 0 | 0 | 0 | 0.00061 | 0 | 0 |
| PGK | 5490.018 | 0 | −1133.834 | 0 | 0 | 1133.834 |
| PGM | −15287.46 | 13327.53 | 0 | 0 | 0 | 0 |
| EN | 81.36511 | −81.44648 | 0.081365 | 0 | 0 | 0 |
| PK | 0 | 48.23862 | −50.54352 | 0.237211 | 0 | 2.067691 |
| LDH | 0 | 0 | 232.001 | −271.4036 | 0.146556 | 0 |
| LEX | 0 | 0 | 0 | 5.055766 | −5.055766 | 0 |
| ATPase | 0 | 0 | 0.415409 | 0 | 0 | −0.415409 |

The ability to describe the Jacobian matrix in terms of concentration variables or flux variables, and consequently being able to describe the dynamics in terms of fluxes or concentrations, is a result of the duality property described herein.

Example 4

Dynamic Properties of the Glycolytic Pathway in *Homo sapiens*

The construction of the key dynamic data matrices constructed for the glycolytic pathway in *Homo sapiens* in Example 1, 2, and 3, now enable analysis of the dynamic properties of the pathway on different time scales.

TABLE 9

The metabolite modal matrix:

| Time Scales (hours) | G6P | F6P | FDP | DHAP | GAP | DPG13 |
|---|---|---|---|---|---|---|
| 4.95978E−07 | −1.35273E−10 | 9.17E−09 | −2.29E−09 | −1.04E−09 | 0.000127 | −1.726916 |
| 9.9213E−06 | −0.411156665 | 1.003003 | −3.7E−08 | 7.48E−13 | −4.53E−09 | 3.06E−06 |
| 6.51335E−05 | −4.34345E−08 | −2.07E−08 | 4.25E−06 | 1.94E−06 | −0.001802 | 0.180719 |
| 0.002226776 | −0.001273406 | −0.001254 | 0.105707 | 0.047837 | −1.255173 | −3.98E−05 |
| 0.003681135 | −0.00075682 | −0.00075 | 0.026351 | 0.011856 | −0.183504 | −0.228332 |
| 0.019825246 | −0.032068777 | −0.032014 | 0.194885 | 0.072614 | −0.149602 | −0.531172 |
| 0.027633412 | 0.381882846 | 0.381411 | −2.204163 | 0.003881 | −0.002006 | −0.00655 |
| 0.104851825 | −15.34226414 | −15.33727 | 11.89888 | 6.163961 | 2.598787 | −4.499937 |
| 0.141641663 | 70.63598759 | 70.61897 | −22.40379 | −11.47598 | −6.562374 | 3.303189 |
| 0.188045512 | −267.7752441 | −267.7267 | −0.090144 | −0.029436 | −0.019904 | −0.000565 |
| 0.197903124 | 215.6225745 | 215.5854 | 10.28596 | 5.212281 | 3.614971 | 0.386219 |
| 2668.439074 | 2.427898913 | 2.427899 | 3.236902 | 1.618453 | 1.618416 | 1.61834 |

| Time Scales (hours) | PG3 | PG2 | PEP | PYR | LAC | ATP |
|---|---|---|---|---|---|---|
| 4.95978E−07 | 0.004722 | −3.14E−05 | −2.38E−08 | −4.08E−10 | 1.77E−16 | 0.000974 |
| 9.9213E−06 | −8.54E−09 | 1.3E−09 | −1.39E−09 | 6.89E−12 | −9.69E−18 | 2.91E−06 |

TABLE 9-continued

The metabolite modal matrix:

| | | | | | | |
|---|---|---|---|---|---|---|
| 6.51335E−05 | 0.17944 | −1.23007 | 6.87E−06 | 5.67E−09 | −5.41E−14 | −0.000102 |
| 0.002226776 | 8.46E−06 | 8.67E−06 | 7.55E−06 | 4.24E−06 | −1.4E−09 | −4.77E−05 |
| 0.003681135 | −0.21689 | −0.215398 | 0.059766 | −1.426032 | 0.000784 | −0.011439 |
| 0.019825246 | −0.454169 | −0.442405 | 1.759867 | 0.001964 | −6.36E−06 | −0.07699 |
| 0.027633412 | −0.01758 | −0.017255 | 0.043766 | 3.28E−05 | −1.55E−07 | 0.01103 |
| 0.104851825 | −4.235859 | −4.215199 | −0.337184 | −4.8E−05 | 1.62E−06 | −0.26406 |
| 0.141641663 | 2.598417 | 2.589042 | 0.828941 | 8.2E−05 | −6.47E−06 | 0.704765 |
| 0.188045512 | −0.000398 | −0.000397 | −0.000188 | −2.76E−08 | 3.5E−08 | −0.000167 |
| 0.197903124 | 0.908935 | 0.906966 | 0.537199 | 1.018456 | 0.999441 | −0.522718 |
| 2668.439074 | 0.809188 | 0.809188 | 0.809159 | 5.87E−09 | 1.65E−10 | 0.809152 |

TABLE 10

The flux modal matrix:

| Time Scales (hours) | HK | PGI | PFK | ALD | TPI | GAPDH | PGK |
|---|---|---|---|---|---|---|---|
| 4.95978E−07 | −0.000974 | 9.31E−09 | −0.000974 | 0.000127 | 0.000127 | −1.727043 | 1.732612 |
| 9.9213E−06 | −0.41116 | 1.41416 | −1.003006 | 3.25E−08 | −4.53E−09 | 3.06E−06 | −1.53E−07 |
| 6.51335E−05 | 0.000102 | 2.28E−08 | 0.000106 | −0.001805 | −0.001804 | 0.182521 | −0.001381 |
| 0.002226776 | −0.001226 | 1.95E−05 | 0.107008 | −1.313044 | −1.30301 | 1.255134 | 5.99E−07 |
| 0.003681135 | 0.010682 | 7.02E−06 | 0.03854 | −0.197999 | −0.195361 | −0.044828 | 2.97E−06 |
| 0.019825246 | 0.044921 | 5.52E−05 | 0.303888 | −0.271873 | −0.222216 | −0.38157 | 1.32E−05 |
| 0.027633412 | 0.370853 | −0.000472 | −2.596604 | 2.206038 | −0.005888 | −0.004544 | 1.16E−07 |
| 0.104851825 | −15.0782 | 0.004993 | 27.50022 | −3.136136 | −3.565174 | −7.098724 | 1.8E−05 |
| 0.141641663 | 69.93122 | −0.017017 | −93.72753 | 4.365443 | 4.913601 | 9.865563 | −6.96E−06 |
| 0.188045512 | −267.7751 | 0.048591 | 267.6367 | 0.040804 | 0.009532 | 0.019339 | 1.06E−08 |
| 0.197903124 | 216.1453 | −0.037179 | −204.7767 | −1.45871 | −1.59731 | −3.228752 | −2.12E−06 |
| 2668.439074 | 1.618747 | −2.55E−08 | −0.000149 | −3.36E−05 | −3.68E−05 | −7.56E−05 | −3.37E−10 |

| Time Scales (hours) | PGM | EN | PK | LDH | LEX | ATPase |
|---|---|---|---|---|---|---|
| 4.95978E−07 | −0.004754 | 3.14E−05 | 0.000974 | 4.08E−10 | −1.77E−16 | −0.000974 |
| 9.9213E−06 | 9.84E−09 | −2.7E−09 | 2.91E−06 | −6.89E−12 | 9.69E−18 | −2.91E−06 |
| 6.51335E−05 | −1.40951 | 1.230077 | −0.000109 | −5.67E−09 | 5.41E−14 | 0.000102 |
| 0.002226776 | 2.15E−07 | −1.12E−06 | −5.1E−05 | −4.24E−06 | 1.4E−09 | 4.77E−05 |
| 0.003681135 | 0.001492 | 0.275164 | −1.497237 | 1.426816 | −0.000784 | 0.011439 |
| 0.019825246 | 0.011765 | 2.202271 | −1.834892 | −0.001971 | 6.36E−06 | 0.07699 |
| 0.027633412 | 0.000326 | 0.061021 | −0.032703 | −3.3E−05 | 1.55E−07 | −0.01103 |
| 0.104851825 | 0.020659 | 3.878015 | 0.073076 | 4.96E−05 | −1.62E−06 | 0.26406 |
| 0.141641663 | −0.009375 | −1.760101 | −0.124094 | −8.85E−05 | 6.47E−06 | −0.704765 |
| 0.188045512 | 1.11E−06 | 0.000209 | 2.13E−05 | 6.26E−08 | −3.5E−08 | 0.000167 |
| 0.197903124 | −0.001969 | −0.369766 | −0.041461 | −0.019015 | −0.999441 | 0.522718 |
| 2668.439074 | −1.56E−07 | −2.92E−05 | −6.33E−06 | −5.71E−09 | −1.65E−10 | −0.809152 |

Figure 4:
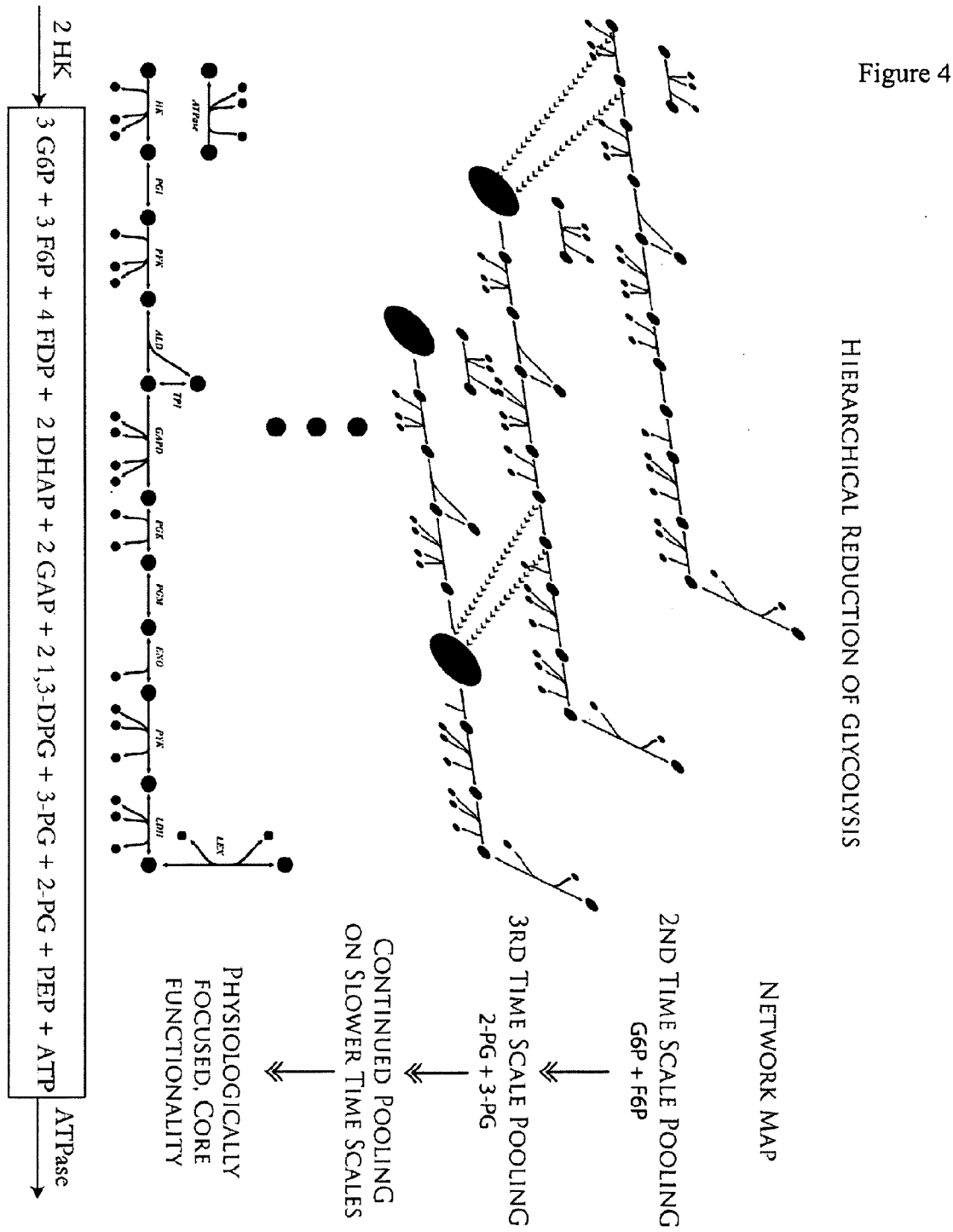
As illustrated in FIG. 4, sometimes it is convenient to think about the hierarchical structure in terms of metabolites and sometimes it is more intuitive to think in terms of the fluxes. The network was constructed using equilibrium constants and concentrations from a kinetic red cell model, which has been validated in the literature. Network dynamics were then described using mass action kinetics for a particular steady state. Abbreviations: TS: time scale in hours, HK: hexokinase, PGI: phosphoglucoisomerase, PFK: phosphofructokinase, ALD: fructose-bisphosphate aldolase, TPI: triose-phosphate isomerase, GAPD: glyceraldehyde phosphate dehydrogenase, PGK: phosphoglucokinase, PGM: phosphoglucomutase, ENO: enolase, PYK: pyruvate kinase, LDH: lactate dehydrogenase, LEX: lactate transporter, ATPase: ATP hydrolysis (demand/utilization).
Figures 1, 15:
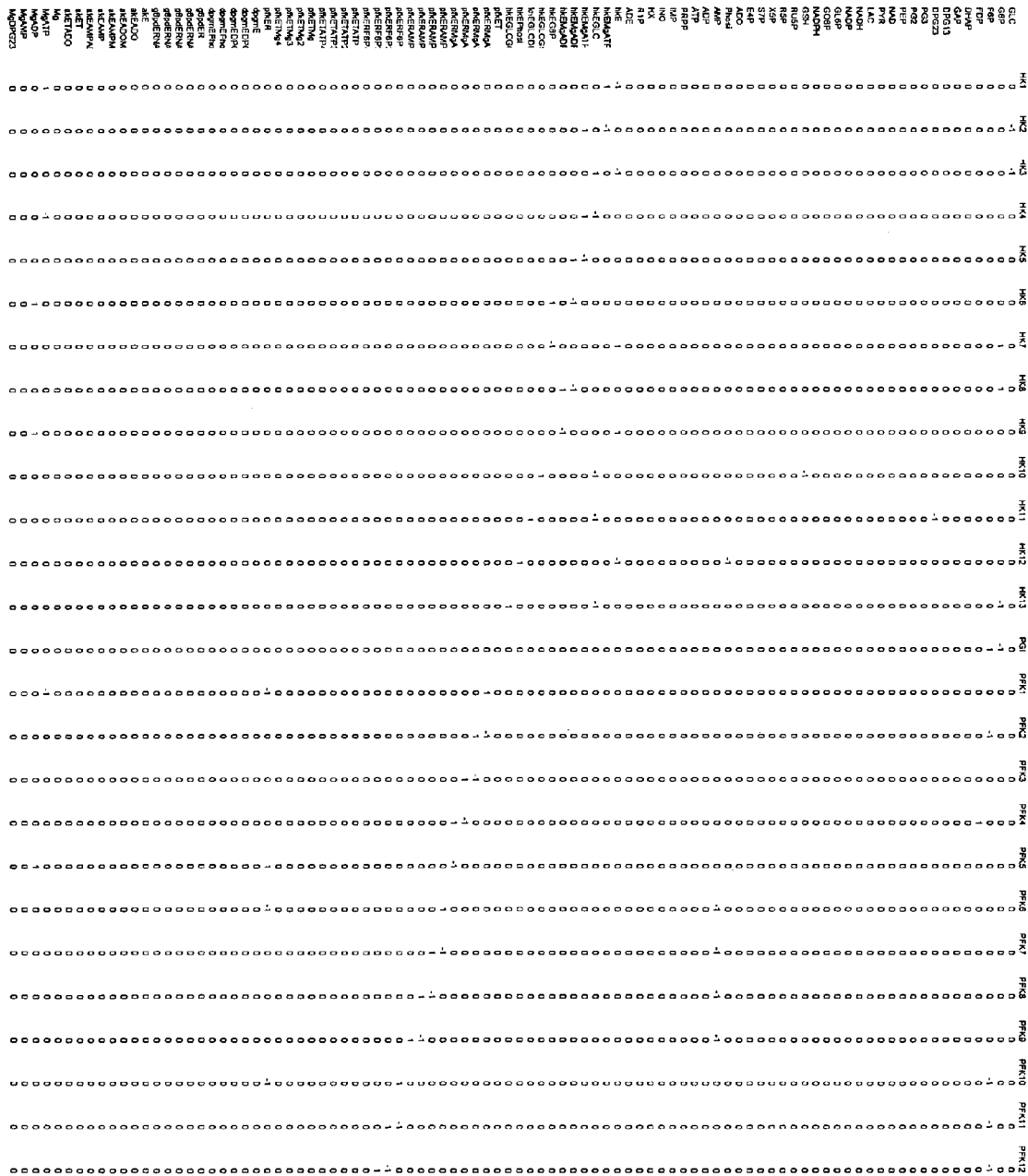
FIG. 15 is a table of the stoichiometric matrix S for the regulated study of the red blood cell, which for ease of viewing is represented in FIGS. 15-1, 15-2, 15-3, 15-4.
Figures 2, 15:
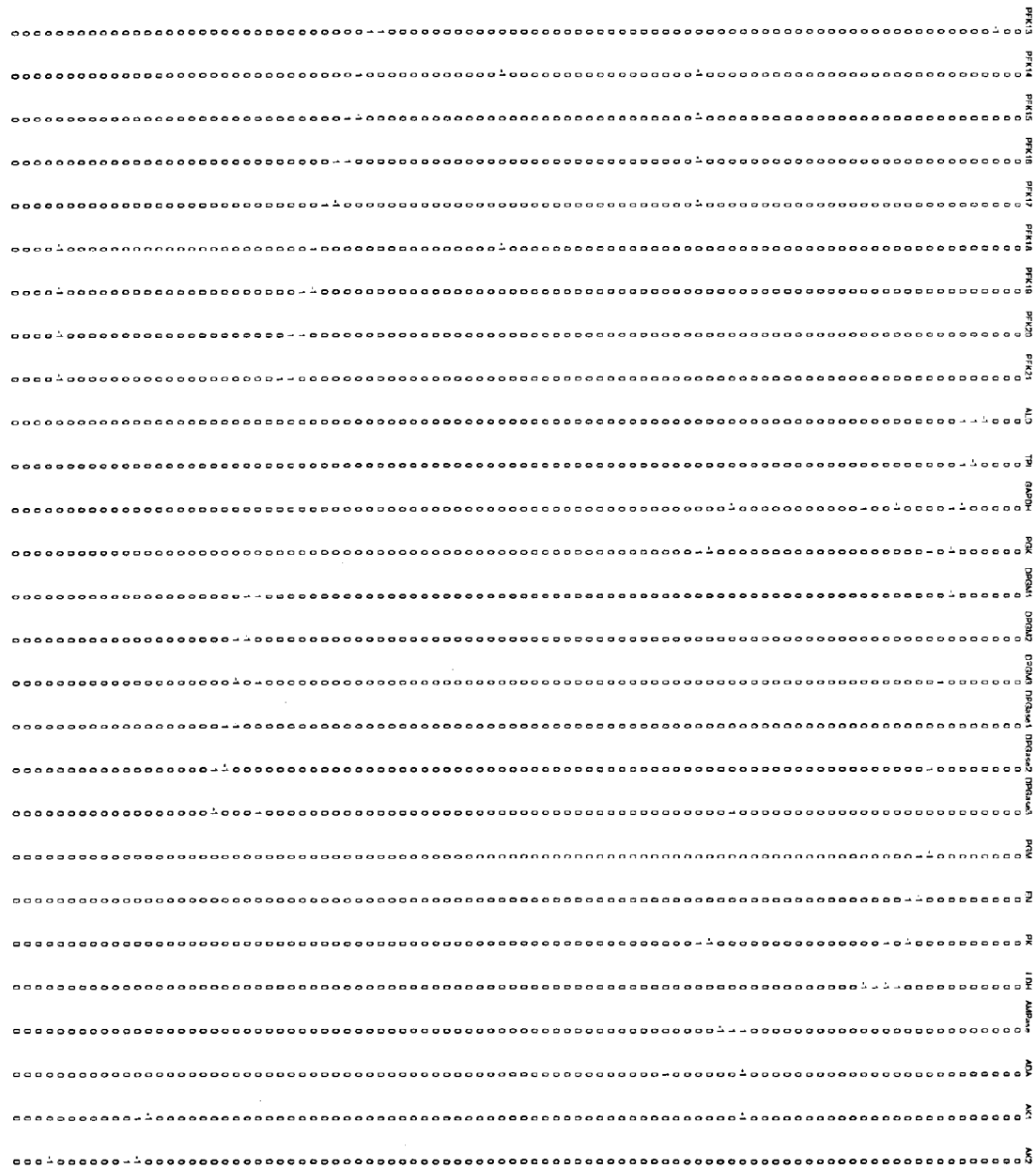
Figures 3, 15:
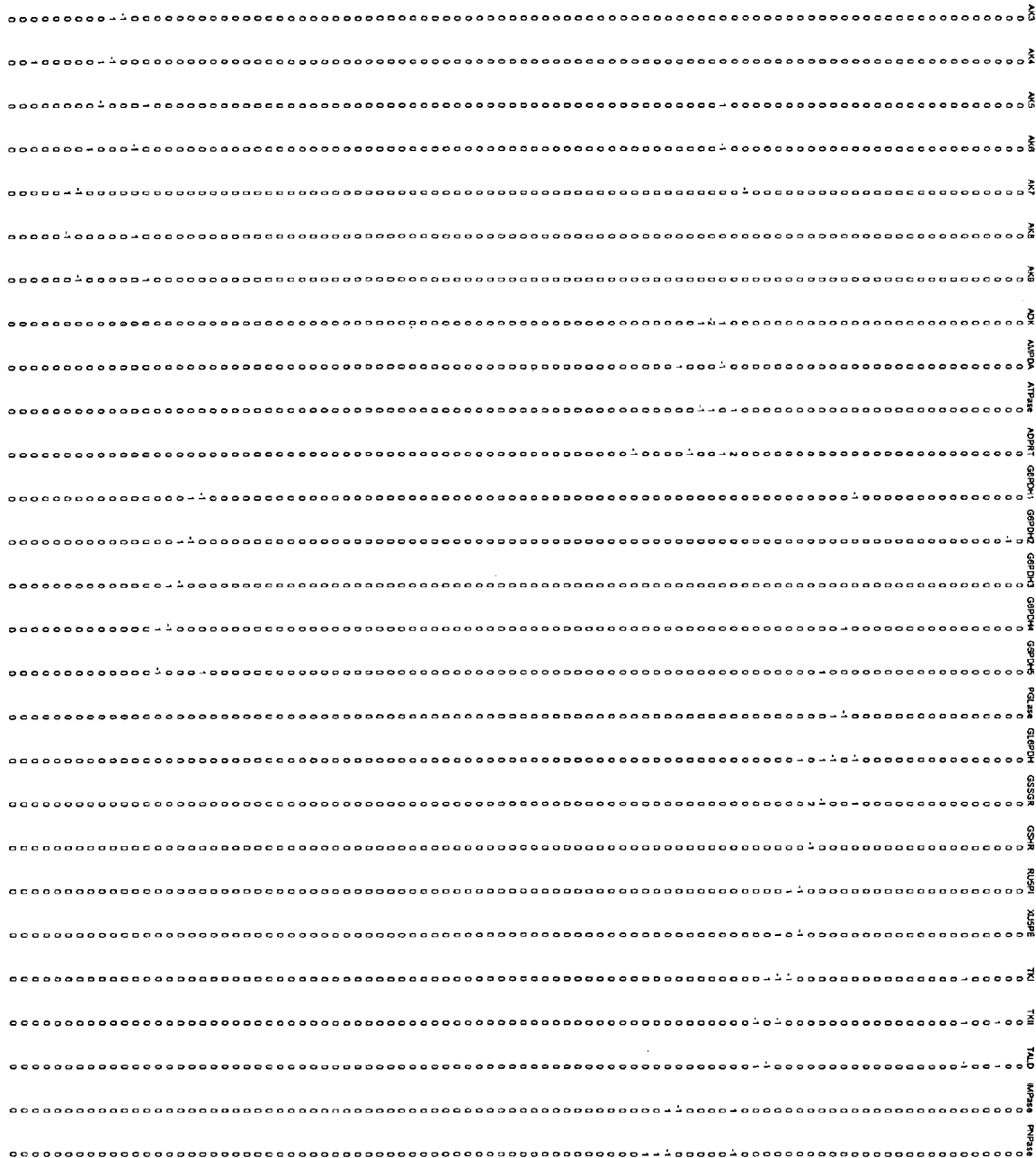
Figures 4, 15:
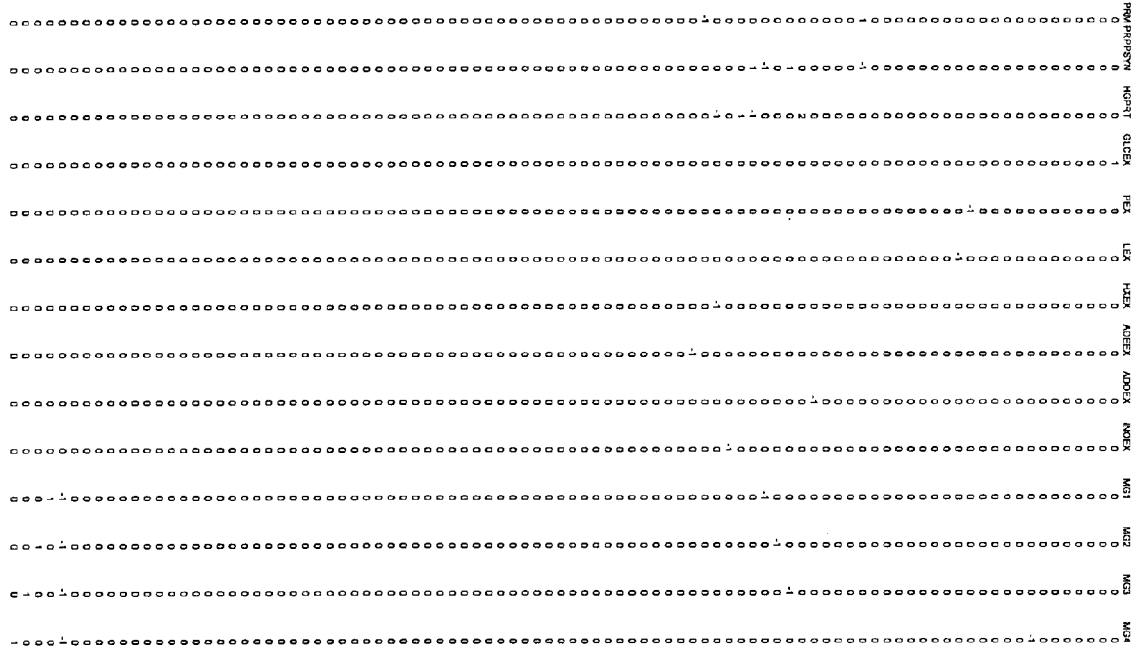
Figures 1, 16:
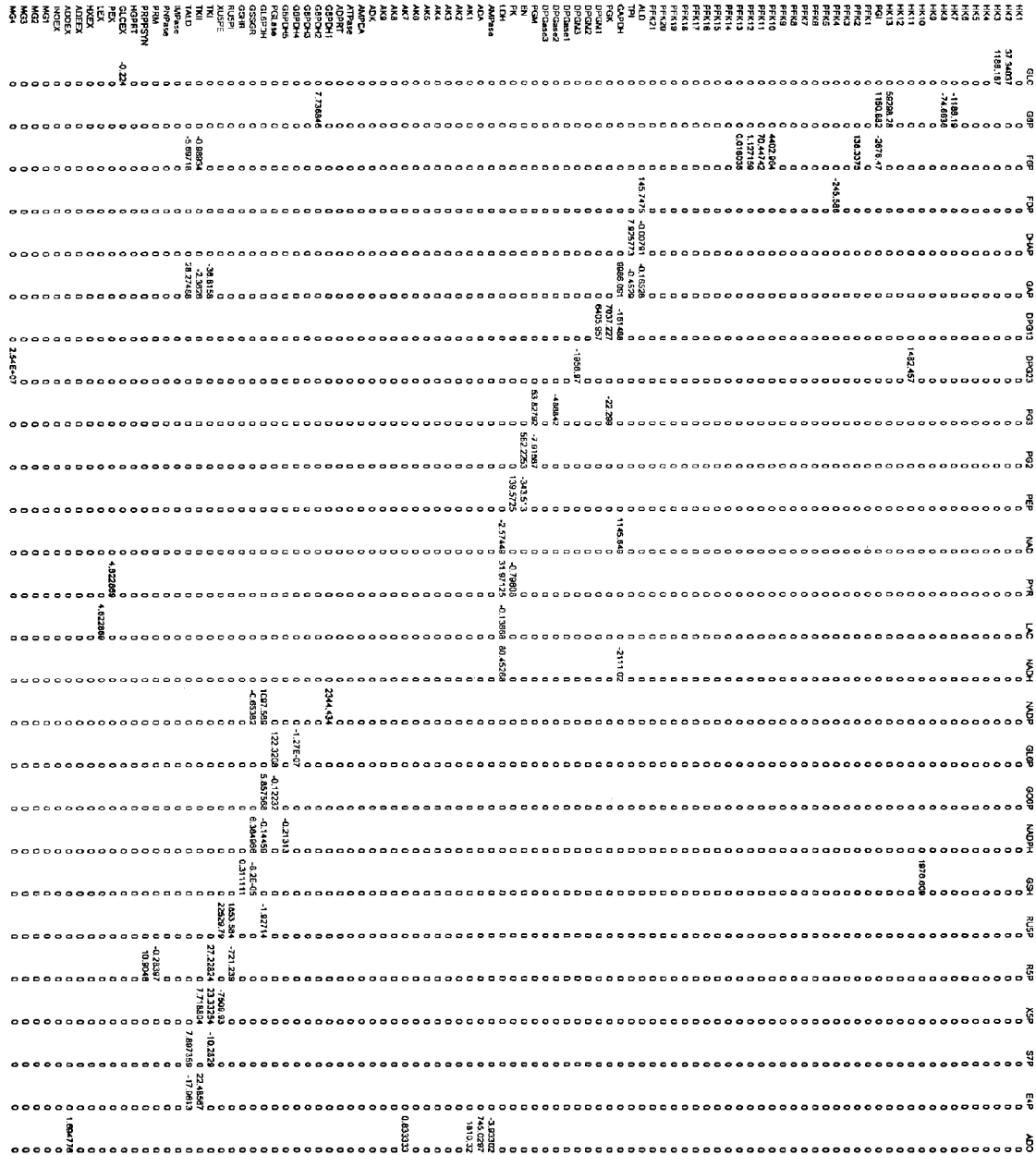
FIG. 16 is a table of the gradient matrix G for the regulated study of the red blood cell, which for ease of viewing is represented in FIGS. 16-1, 16-2, 16-3, 16-4.
Figures 2, 16:
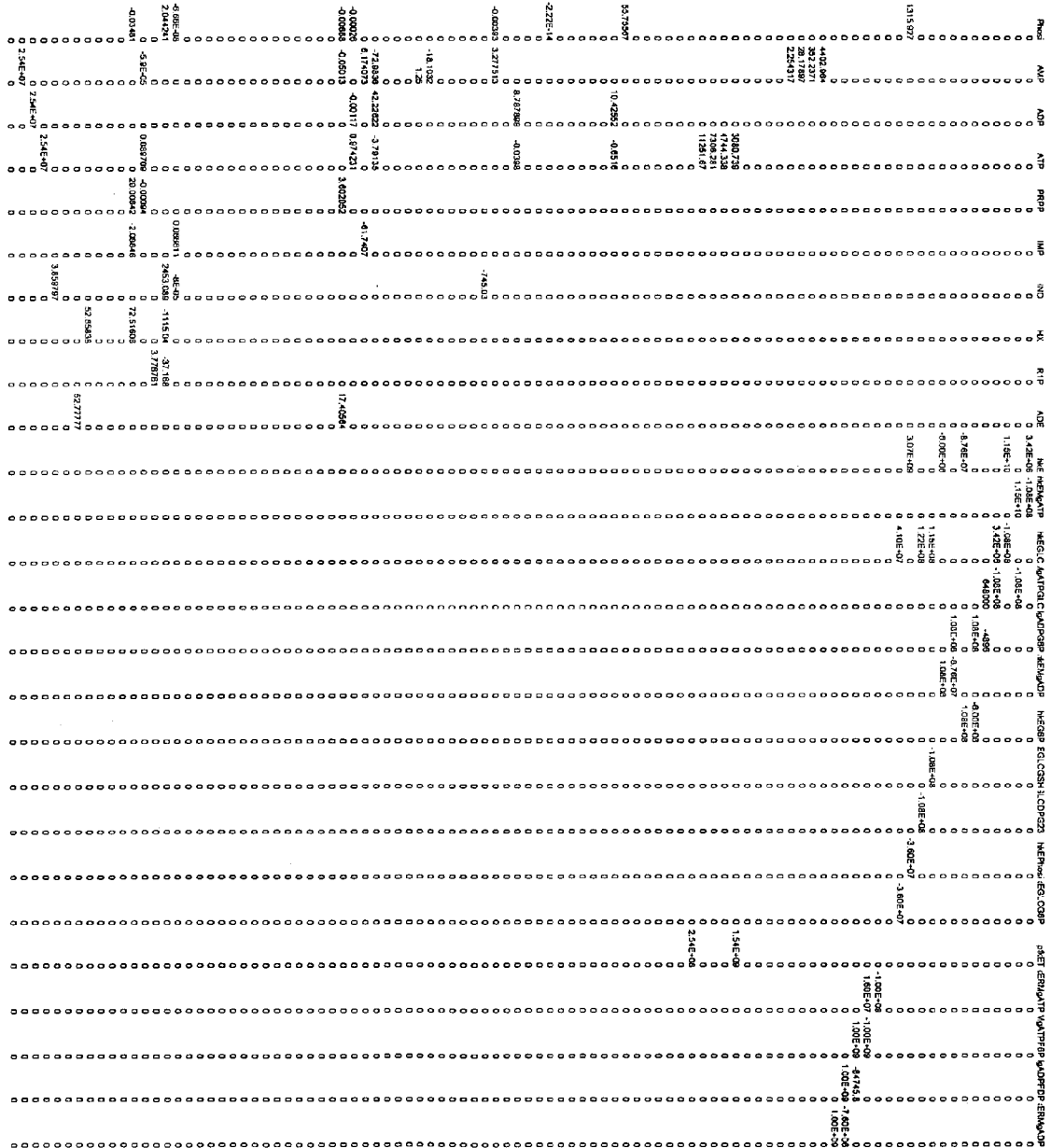
Figures 3, 16:
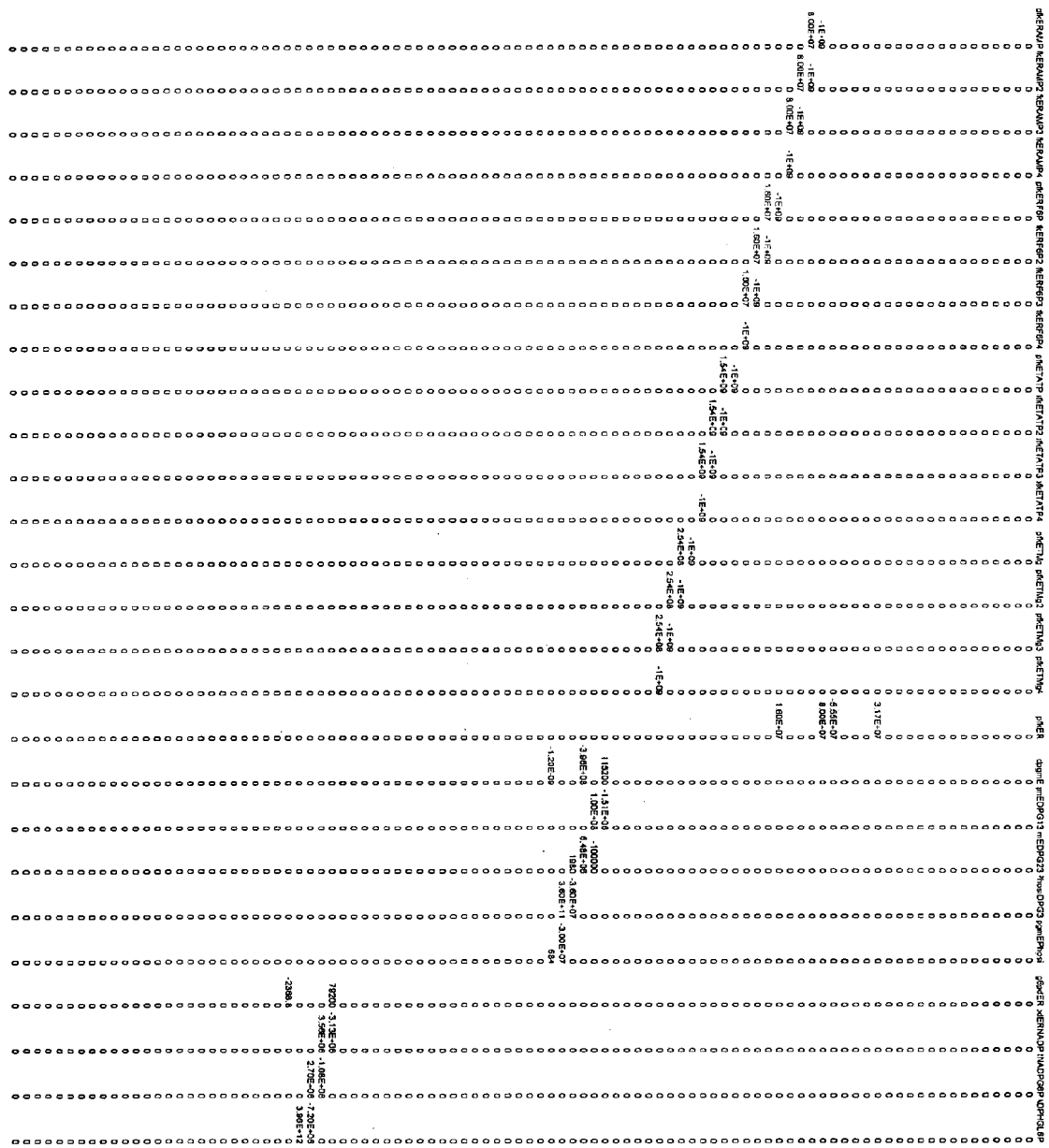
Figures 4, 16:
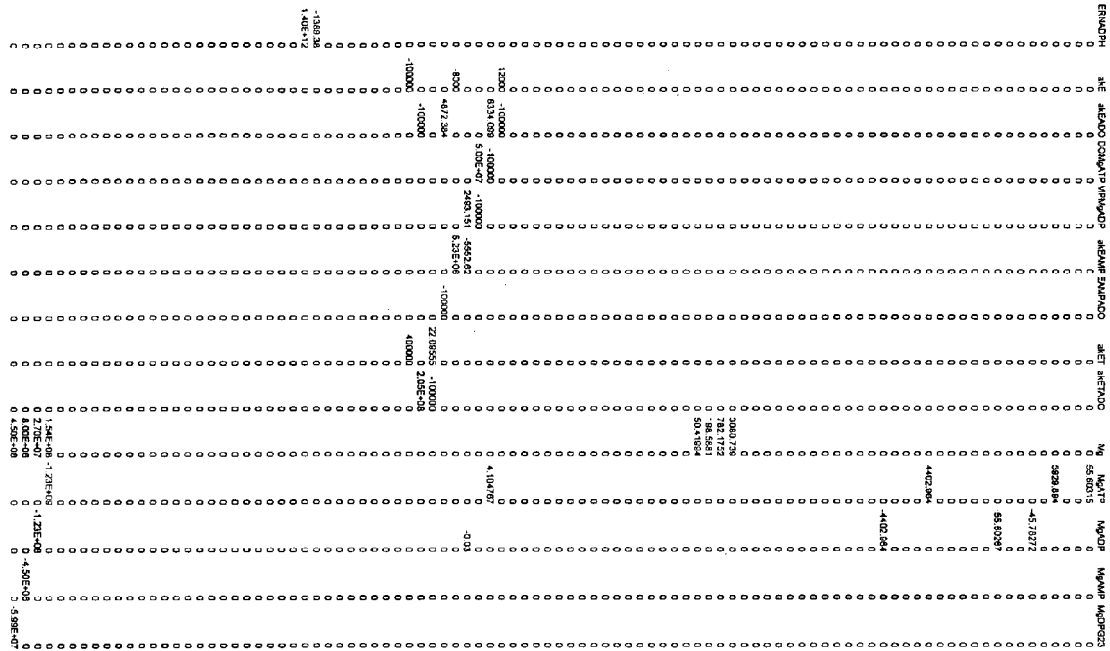

Pooling of variables (metabolites or fluxes) refers to the formation of aggregate groups of variables, in which the group of variables move together in a concerted manner. Pools that form on very fast time scales reflect the formation of chemical equilibrium pools, whereas pooling that occurs on the slower time scales reflect physiologically relevant interactions. Moving from the very fast time scales to the slower ones (FIG. 4), one observes the well-known examples of pool formation between hexose phosphates (HP) and phosphoglycerates (PG). With successive removal of modes on the slower time scales, more and more of the metabolites begin to form aggregate variables and move together in a concerted fashion at fixed ratios. For glycolysis alone the successive aggregation of chemical moieties (i.e. HP, PG) culminates in, on the slowest time scale, the formation of a physiologically meaningful pool that represents the sum of high-energy phosphate bonds found in the glycolytic intermediates (i.e. their ATP equivalents) (FIGS. 3.4 and 4). The last row of $M^{-2}$ for $J_v$ shows that this pool is moved by hexokinase as the input and ATPase as the output (FIG. 3B.4).

Example 5

Red Blood Cell Metabolism in *Homo sapiens*

The construction of the key dynamic data matrices constructed for a full model of metabolites in *Homo sapiens*.

Currently, the human red cell is the only cell-scale kinetic model available, whose formulation followed a 30 year history of iterative model building (summarized in (Joshi and Palsson, 1989; Joshi and Palsson, 1990), which are both hereby incorporated by reference in their entireties). Analysis of the dynamic structure of this model resulted in the simplification of network dynamics and the description of the cellular functions in terms of physiologically meaningful pools of metabolites. Analysis of the hierarchical dynamics of the human red cell model resulted in a richer and more complex physiological pool formation (Kauffman et al., 2002, which is hereby incorporated by reference) that detailed above for glycolysis alone. An overview of the hierarchical reduction of the network into a functional diagram is schematized in FIG.

Figure 5:
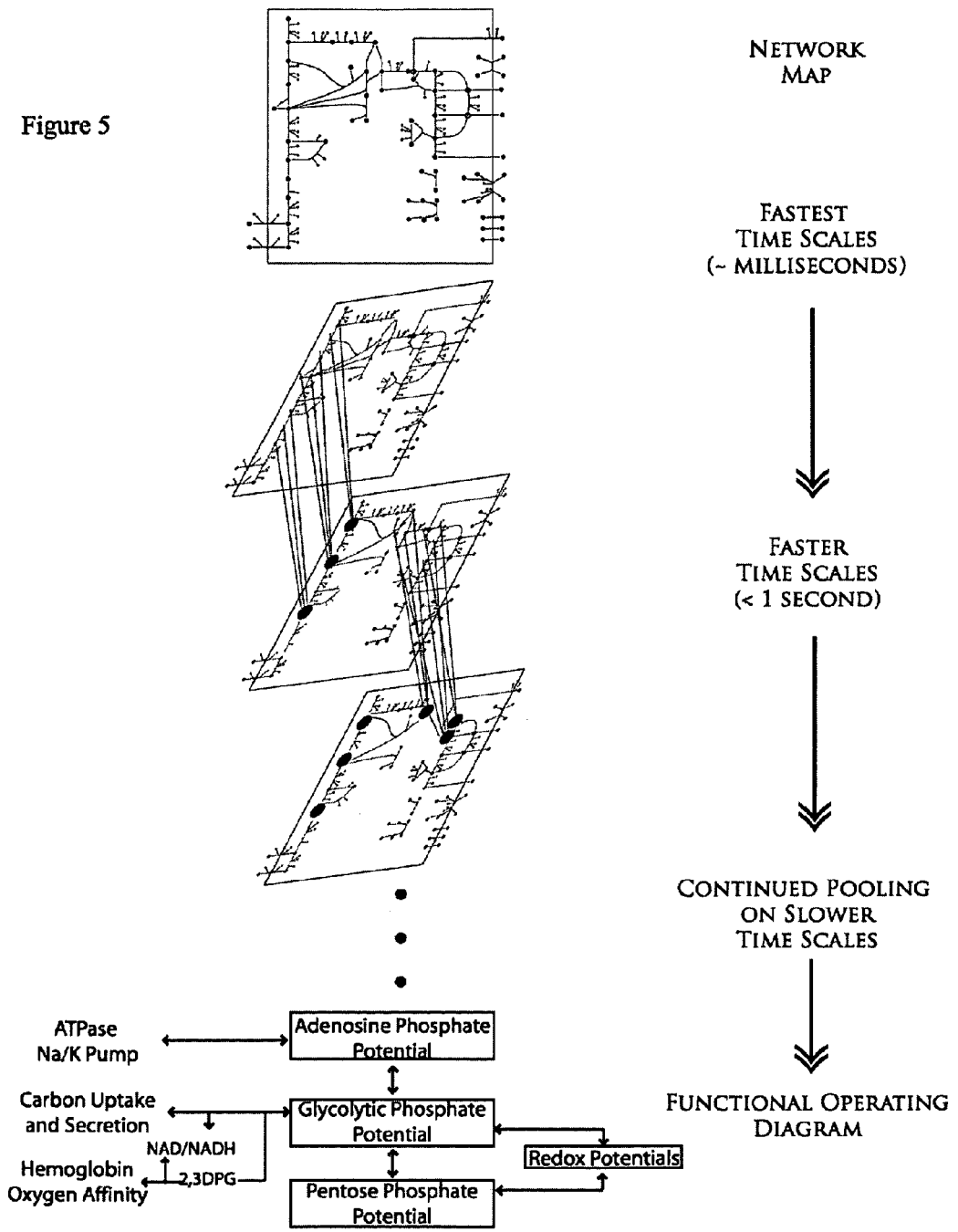
FIG. 5 shows the hierarchical analysis and simplification of red cell metabolism.

4. For example, the Adenosine Phosphate Potential is defined analogously to Atkinson's Energy Charge (Atkinson, 1968, which is hereby incorporated by reference). As originally elaborated by Reich and Selkov (Reich and Selkov, 1981, which is hereby incorporated by reference), this "potential" is the ratio of the number of energy rich phosphate bonds and the ability or capacity to carry such bonds. The different pools of metabolites in the red cell contribute to phosphate potentials and/or oxidation/reduction potentials. The result of the pool formation is an 'operating diagram' (bottom of FIG. 5) that describes the function of the metabolic network in the red cell slower time scales (minutes to hours).

This procedure characterized the dynamics of a network about a particular steady state. The first step involves specifying a particular steady state flux distribution. Next, the concentrations (generally there will need to be some approximations of these) of the metabolites at this steady state need to be identified. Third, the equilibrium constant approximations need to be determined and the steady state fluxes and concentrations will be incorporated into mass action rate laws. Finally, the forward rate constants can be solved by solving n linear equations for forward rate constants.

For situations in which all of the concentrations are not known or if one wants to trace the effects of particular metabolites in multiple rate constants, rather than n linear equations, one can solve the m equations by solving the steady state mass conservation relationship (S.v~0). This will result in multiple alternative solutions.

As described previously (5), the dynamics of this model are consistent with the observations from previous studies in which the well-known examples of pool formation between hexose phosphates (HP) and phosphoglycerates (PG). With successive removal of time scales (modes), more and more of the metabolites begin to form aggregate variables and move together in a concerted fashion at fixed ratios. For glycolysis alone, the successive aggregation of chemical moieties (i.e. HP, PG) culminates in, on the slowest time scale, the formation of a physiologically meaningful pool that represents the sum of high-energy phosphate bonds found in the glycolytic intermediates (i.e. their ATP equivalents). The last row of the modal matrix for the flux Jacobian (Supplemental Material) shows that this pool is moved by hexokinase as the input and ATPase as the output, reflecting the catabolism of glucose to generate ATP. The dimensions of the matrices and their corresponding subspaces are shown in Table 11. This is a single pathway model, hence the single dimension if the right null space is expected.

TABLE 11

The dimensions of the stoichiometric and gradient matrices, along with their ranks and sizes of their null spaces for the mass action glycolytic model.

|  | Rows | Columns | Rank | Left Null | Right Null |
|---|---|---|---|---|---|
| Stoichiometric Matrix | 12 | 13 | 12 | 0 | 1 |
| Gradient Matrix | 13 | 12 | 12 | 0 | 0 |

Scaleability of the Approach

Figure 8:
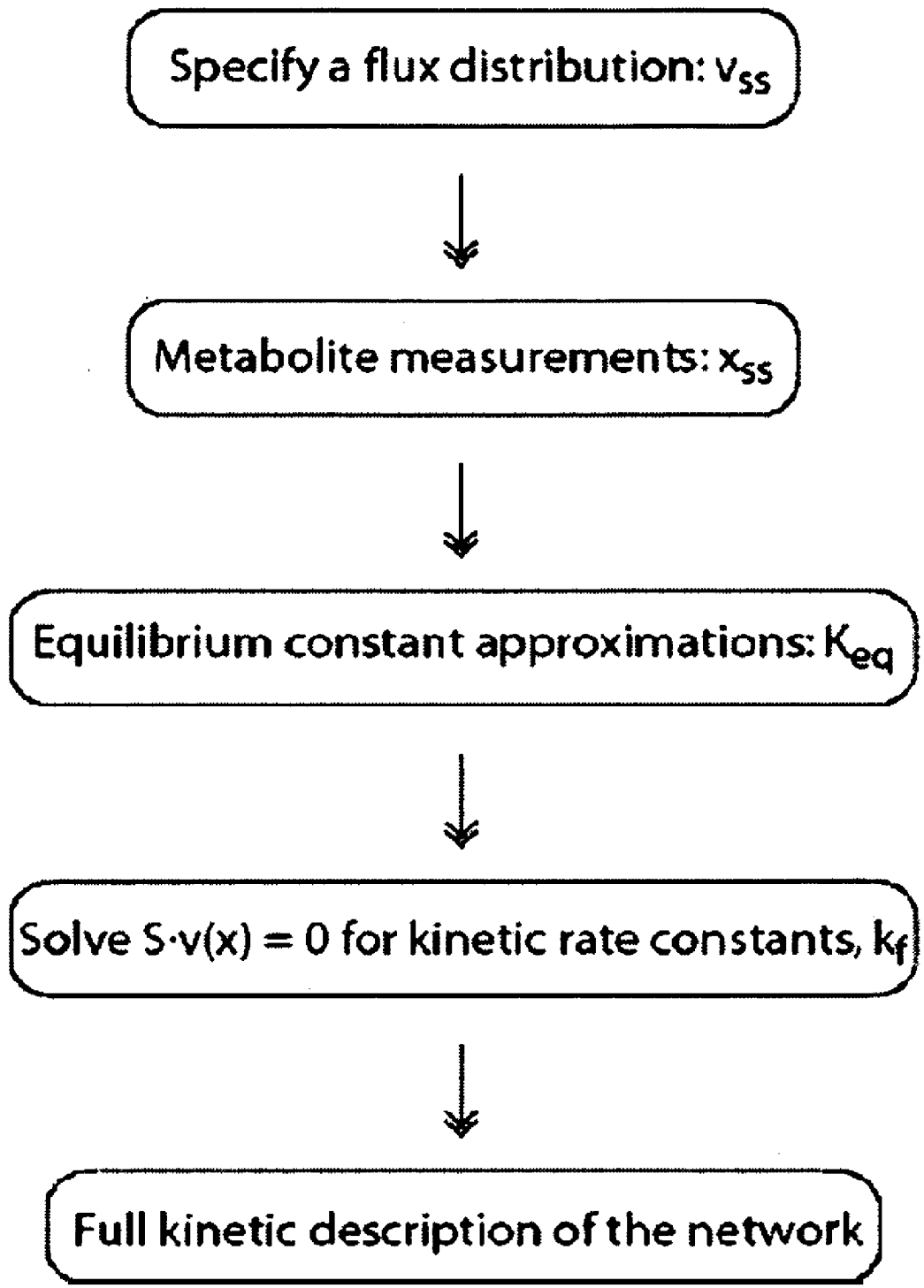
FIG. 8 is a block diagram of one embodiment for preparing the model described herein.

Since the approach outlined in FIG. 8 was successful for a small pathway model we moved to apply this to expand the scope of the pathways. Building from the glycolytic pathway, the approach was applied to a full model of human red blood cell metabolism. Steady state concentrations fluxes and concentrations (16) reported in the literature were used in conjunction with equilibrium constants reported in the literature (17, 18). The procedure outlined in FIG. 8 was again applied.

Figure 10:
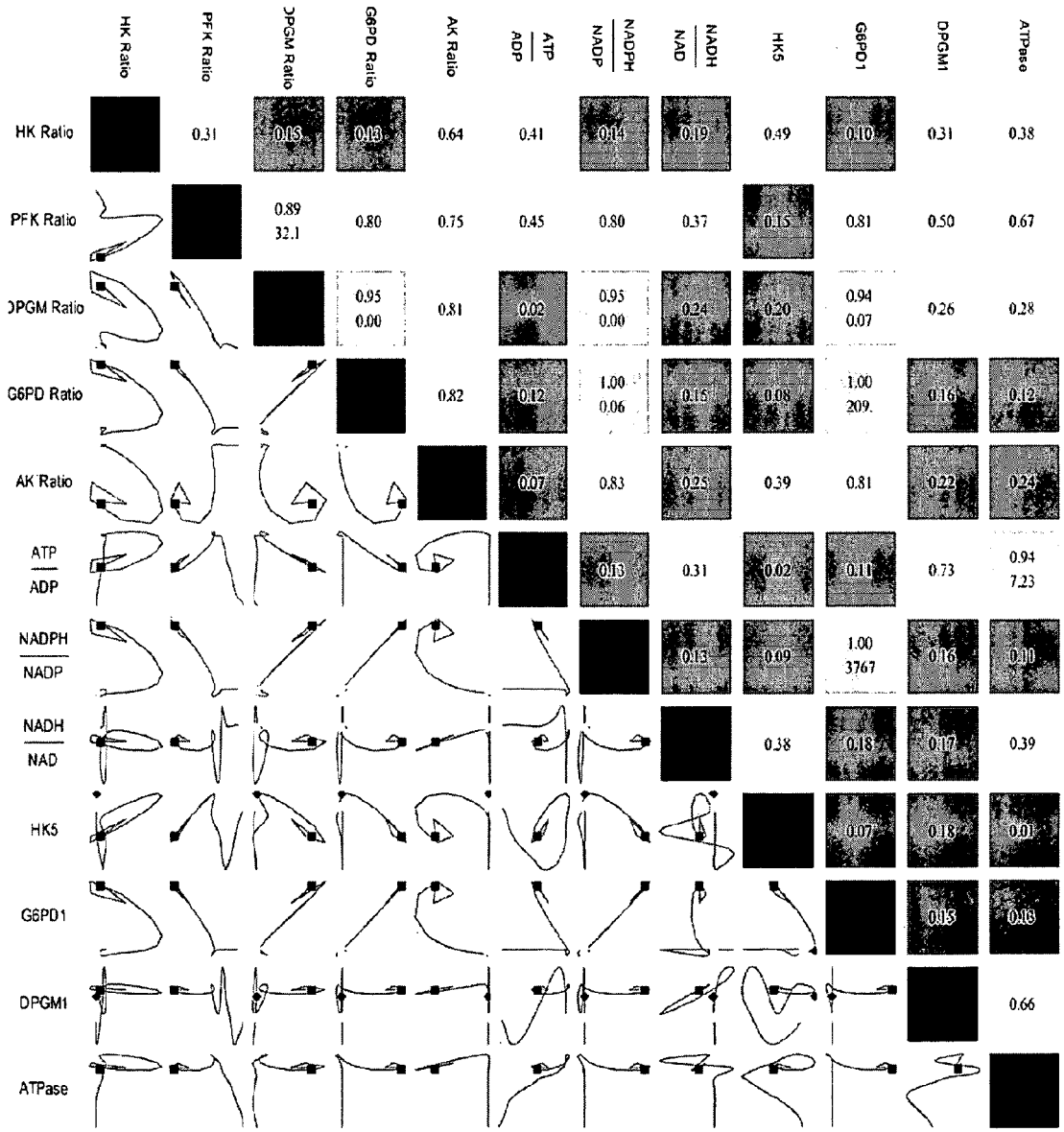
FIG. 10 is a tiled phase plane diagram for selected grouped variables and reaction fluxes for the cell in response to a transient, instantaneous decrease in ATP by 60%. HK Ratio, PFK Ratio, DPGM Ratio, G6PD Ratio, and AK Ratio are the ratios of the free to bound forms of the corresponding enzymes. The lower left triangle depicts the trajectories of the corresponding variables. The upper right triangle shows the correlation coefficient (when the correlation coefficient is greater than 0.85, the slope of the line appears below it). The G6PD ratio, NADPHINADP ratio, and G6PD I flux are all highly correlated, as are the ATPase flux and the ATP/ADP ratio.

A map of the network is shown in FIG. 10 and the dimensions of the network along with the size of the subspaces are shown in Table 12.

TABLE 12

The dimensions of the stoichiometric and gradient matrices, along with their ranks and sizes of their null spaces for the mass action model of the red cell network.

|  | Rows | Columns | Rank | Left Null | Right Null |
|---|---|---|---|---|---|
| Stoichiometric Matrix | 36 | 42 | 33 | 3 | 9 |
| Gradient Matrix | 42 | 36 | 36 | 6 | 0 |

As expected from the size of the left null space, there are three conserved pools of metabolites, the stoichiometric sum of all of the phosphate containing compounds, the NAD moiety, and the NADP moiety. The amount of glutathione in the network is also conserved, however since the dimeric form is not included as a dynamic variable in the network, it does not appear in the left null space. The size of the right null space increased significantly, by 8 dimensions, reflecting the various alternate pathways that can occur from the Rappoport-Leubering Shunt, the pentose-phosphate pathway, and the connections between the non-oxidative branches of the pentose phosphate pathway and the nucleotide salvage pathways.

The gradient and Jacobian matrices have the characteristics leading towards the expected behavior for the metabolic network, such as hierarchical structure with fast reactions corresponding to isomerization reactions and slower ones reflecting the more physiological behaviors of the network, such as phosphate group transfers. There is good time scale separation (about 20 milliseconds to 5 hours), although the slowest and fastest modes of the traditional red cell model is slightly larger (16, 19). These slower time scales in the kinetic model resulted from the potassium leak channels (20, 21), which were not included in this model. The compositions of the very fast motions are similar to those seen for the red cell (e.g. isomerization between glycolytic intermediates, hexose sugars, pentose sugars, etc). With this implementation, although the diphosphoglycerates move on the slower modes in the network, they are still faster than expected (on the order of 5 minutes as opposed to 10 hours).

Construction of Mechanistic Regulated Model of the Human Erythrocyte

Fundamentally, all interactions between metabolites and enzymes are bilinear, including regulatory reactions (22). The mass action model for the red blood cell was expanded in order in order to include an increased level of detail for the biochemical reactions, accounting for mechanistic regulation in the key regulatory enzymes of the red cell. Many of the association and dissociation constants for the steps involved in enzymatic catalysis for the enzymes in the red cell have been characterized. The five key regulatory enzymes in the red blood cell were described in terms of their mechanisms, these include hexokinase (HK), phosphofructokinase (PFK), diphosphoglyceromutase and diphosphoglycerate phosphatase (DPGM and DPGase carried out by the same enzyme), glucose-6-phosphate dehydrogenase (G6PDH), and adenosine kinase (AK). The mass action model discussed in the previous section was used as a basis for this model. The incorporation of the bilinear interactions reflecting small metabolite regulation of the enzymes resulted in a dramatic increase in the size of the network. Given the complexity and increase in size, the addition of each regulated enzyme was carried out in a systematic, 'modular' manner. Thus the parameters for each enzyme were calculated individually.

After each individual enzymatic step was completed and test, they were integrated into the whole network model. Since a particular flux state was under consideration, there were no problems with alternative flux distributions in the network.

Figure 9:
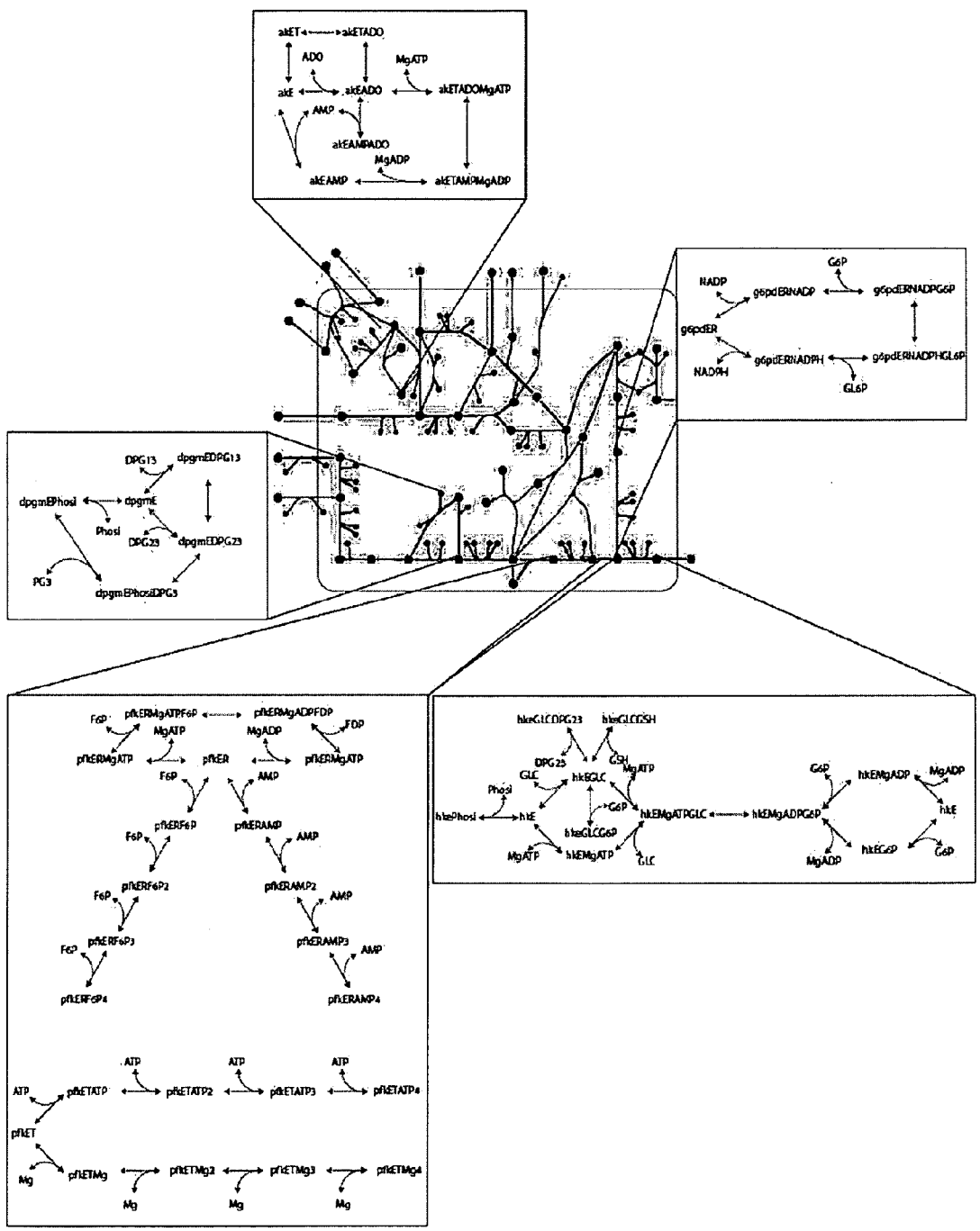
FIG. 9 shows the hierarchical reduction of the pathway discussed in Example 5 below. The reaction scheme for hexokinase as described by (23) hkE represents the unbound, free form of the enzyme. The individual steps and interactions accounting for the catalytic steps in PFK in addition to the allosteric interactions. Reaction scheme for the Rapoport-Leubering shunt which is carried out by the same enzyme (31). The reaction schemes for Glucose-6-Phosphate Dehydrogenase as described by (23) g6pdER represents the active enzyme. The reaction schemes for Adenosine Kinase as described by (25) akE represents the enzyme in the catalytic state and akET represents the tense or inactive form of the enzyme. Other abbreviations: G6P: Glucose-6-phosphate, F6P: Fructose-6-phosphate, FDP: Fructose-1,6-bisphosphate, DHAP: Dihydroxyacetone phosphate, GAP: Glyceraldehyde-3-phosphate, DPG 13: 1,3-bisphosphoglycerate, DPG23: 2,3-bisphosphoglycerate, PG3: 3-phosphoglycerate, PG2: 2-phosphoglycerate, PEP: Phosphoenolpyruvate, PYR: Pyruvate, LAC: Lactate, NADH: Nicotinamide adenine dinucleotide (reduced), GL6P: 6-Phospho-D-glucono-1,5-lactone, G06P: 6-Phospho-D-gluconate, NADPH: Nicotinamide adenine dinucleotide phosphate (reduced), GSH: glutathione (reduced), RU5P: Ribulose-5-phosphate, R5P: Ribose-5-phosphate, X5P: Xylulose-5-phosphate, S7P: Sedoheptulose-7-phosphate, E4P: Erythrose-4-phosphate, ADO: Adenosine, AMP: Adenosine monophosphate, ADP: Adenosine diphosphate, ATP: Adenosine triphohsphate, PRPP: 5-Phospho-D-ribose I-diphosphate, IMP: Inosine monophosphate, INa: Inosine, HX: Hypoxanthine, RIP: Ribose-1-phosphate, ADE: Adenine, Phosi: Monophosphate.

The mechanism for unordered mechanism for hexokinase along with the association and dissociation constants were used as described in (23). FIG. 9 illustrates the individual steps. The total amount of enzyme is conserved (appears in the left null space) and was fixed at 24 nM as described by (23). The net flux for the reaction was fixed according to the steady state flux for the mass action model. The regulatory interactions by 2,3DPG and G6P do not carry net fluxes, so their equilibrium concentrations were calculated. The remaining sets of intermediate concentrations were then calculated.

PFK is a tetramer and as is apparent from the reaction diagram in FIG. 9, it has four binding allosteric regulators. Although such interactions have been described using the well known Hill equation, they can more appropriately be directly described as a set of sequential bilinear interactions. Association and dissociation constants for the regulated steps for PFK in the red blood cell were not available, hence an approximation of 100,000 was made for most of the steps, for the exception of the catalytic transition, which was assumed to be much slower. The total concentration of enzyme was 0.033 11M according to (24).

The diphosphoglyceromutase and diphosphoglycerol phosphatase reactions are both carried out by the same enzyme and the enzymatic steps were described according to (23). As with HK, the majority of the association and dissociations steps were measured (23). A similar procedure was carried out in order to calculate the concentrations of the enzyme-metabolite intermediates.

The reactions for G6PDH were implemented as described by (23) and solved in an analogous manner as HK. The reaction scheme for AK is outlined in FIG. 9, as described by (25). The magnesium equilibrium reactions with 2,3DPG and the adenosine phosphates were implemented as described in (17).

A summary of the dimensions and sizes of the subspaces for the regulated model appear in Table 13.

TABLE 13

The dimensions of the stoichiometric and gradient matrices, along with their ranks and sizes of their null spaces for the regulated mass action model of red cell metabolism.

| | Rows | Columns | Rank | Left Null | Right Null |
|---|---|---|---|---|---|
| Stoichiometric Matrix | 92 | 94 | 82 | 10 | 12 |
| Gradient Matrix | 94 | 92 | 87 | 5 | 3 |

Note that this network is more than twice as large as the previous version. Enzyme catalyzed mechanisms were introduced in this model for 5 enzymes and the size of the left null space increased from 3 to 10. The size of the left null space grew by 7 dimensions due to the addition enzymes as reactants; 5 enzymes (note that PFK has an inactive and active form) plus the conservation of total magnesium. The right null space increased by 3 as a result of the nonsequential mechanism of some of the regulated enzymes, such as HK.

Modal matrices for larger networks are much more difficult to interpret and were dependent on involved algorithmic approaches to elucidate the structure (2). As alluded to earlier, this is because as the size of networks increase and the non-integer entries in G which tends to be an illconditioned matrix, interactions become more tightly tied together. However, observing the structure of the modal matrix for the regulated network (see Supplemental Material) a few points can be observed, The time scale separation has improved from the non-regulated model, with motions ranging from less than microseconds to ten hours.

The slow modes are dominated by the metabolite bound enzymes.

In particular, the reactions that have a larger number of intermediate complexes playa more dominant role, especially at the slower time scales.

The movement of 2,3DPG (enzyme bound forms) have moved to the slowest time scales.

In short, the structure of the modal matrix more closely approximates the features in the full red cell kinetic model. This has encouraging and interesting implications, since the starting point was a basic model of glycolysis, expanded it to a model of red cell metabolism, and then incorporated regulatory interactions in a mechanistic manner. The results from the regulated model of red cell metabolism suggest that one manner in which regulatory enzymes exert their influence over the rest of the network is their ability to bind more than one substrate and to exist in multiple states (active and inactive).

Simulations

Figure 11:
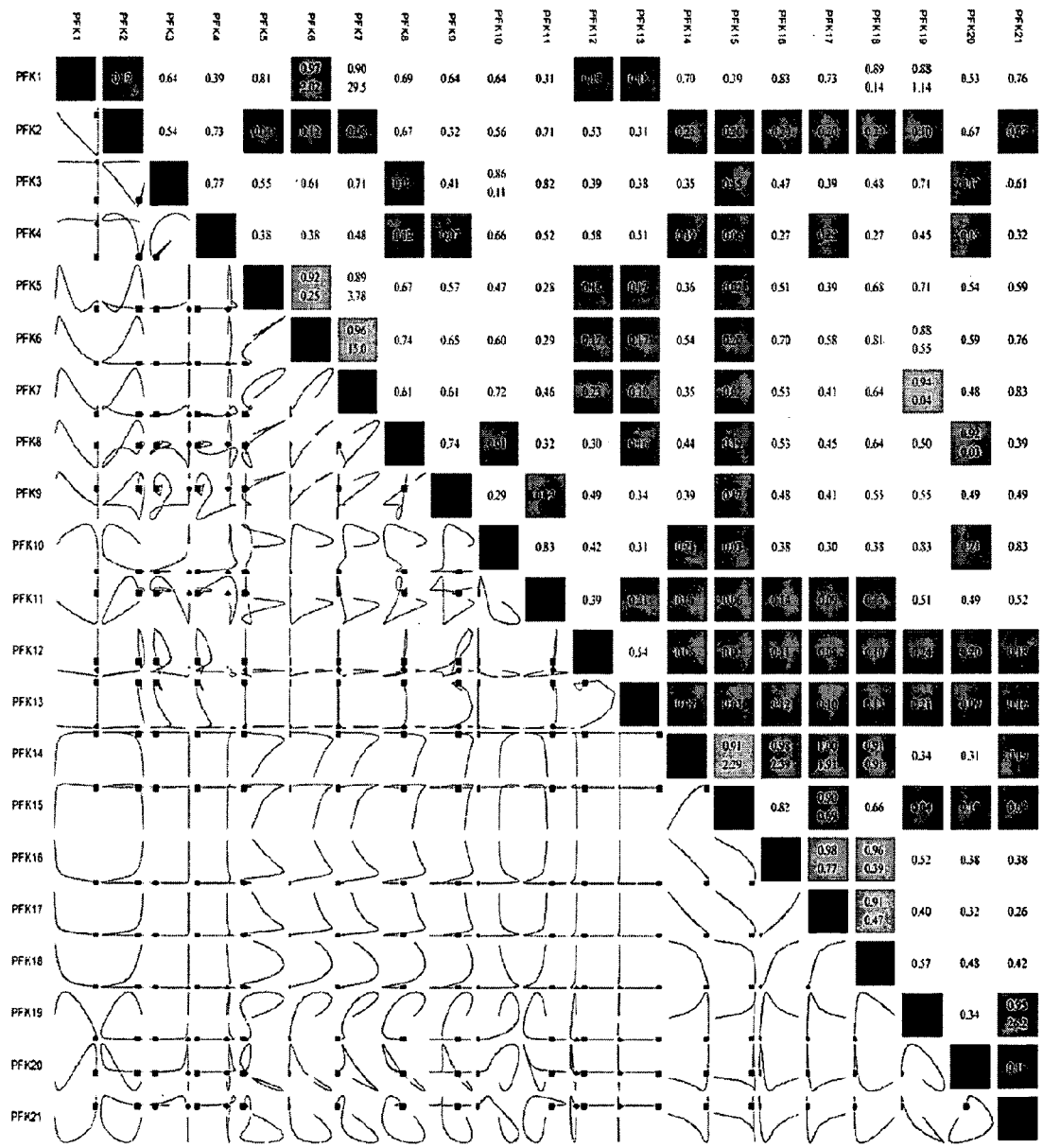
FIG. 11 is a tiled phase plane diagram for all of the fluxes involving the enzyme PFK for the cell in response to a transient, instantaneous decrease in ATP by 60%. Note that not all of the steps are correlated with one another. Indeed, the net flux through the enzyme is actually a sub-network in and of itself. The catalytic step is PFK3. PFK14 through PFK17 reflect ATP binding to the tense form of the enzyme and PFK18 through PFK21 represent Mg binding to the tense form of the enzyme. Correlations among some of the fluxes are observed, for example, the sequential binding of multiple ATP molecules to the enzyme. Other fluxes move dynamically independently from the other PFK fluxes, for example PFK15 and PFKI8.
Figure 12:
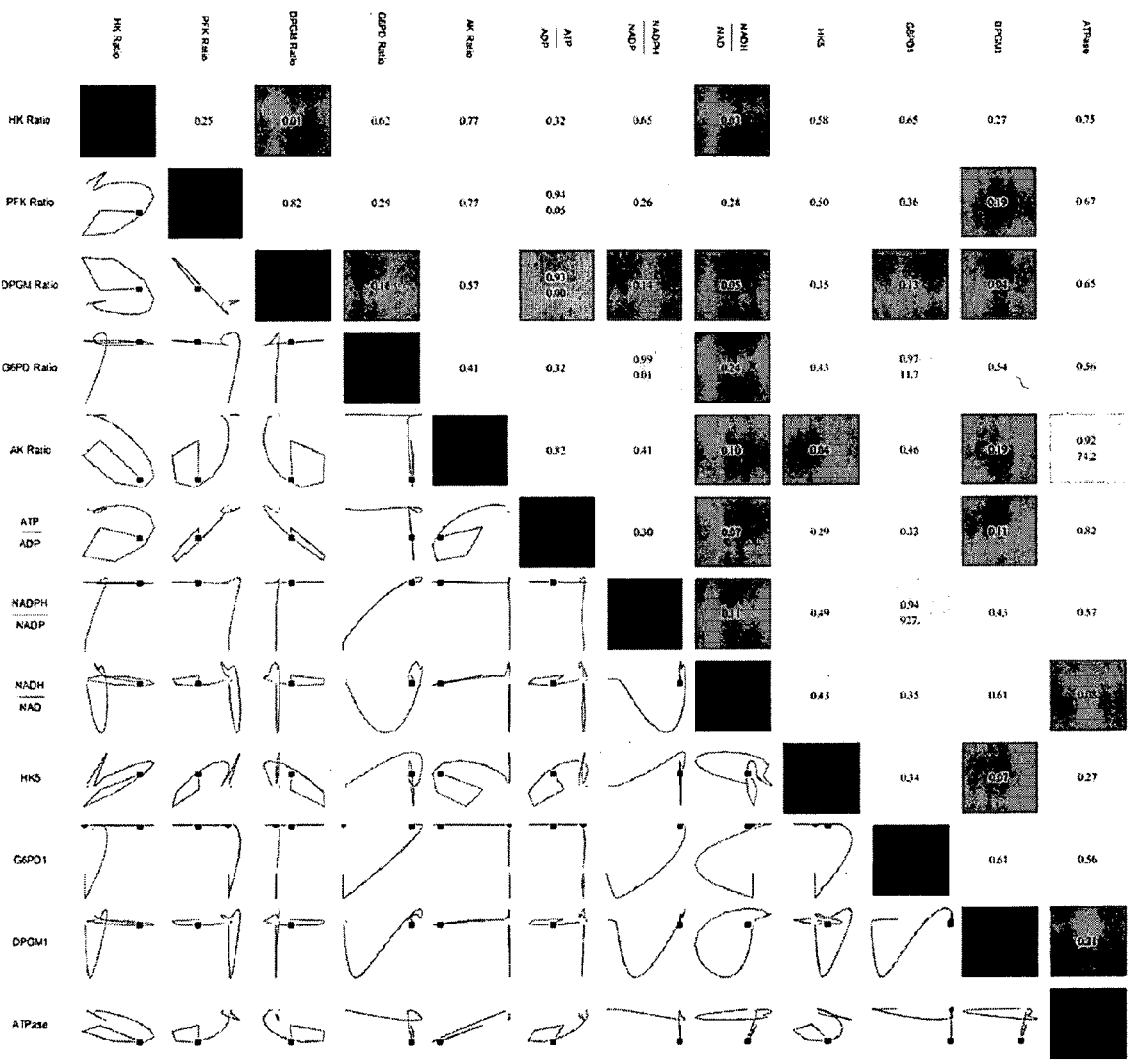
FIG. 12 is a tiled phase plane diagram for selected grouped variables and reaction fluxes for the cell in response to a transient, instantaneous decrease in NADPH by 80%. Similar to the simulation with ATP reduction, the G6PD1 flux, G6PD Ratio, and NADPHINADP ratio are all highly correlated during the time course.

Simulations were carried out with the regulated cell scale model in response to instantaneous ATP depletion (FIGS. 10 and 9) or NADPH depletion. The large number of fluxes and concentrations in the network preclude the ability to plot all of them in a single figure, so key fluxes and concentration variables in different pathways are plotted. Just as ratios of metabolites (e.g. Atkinson's Energy Charge) provide more insight than individual metabolite concentrations, we consider the ratios of the enzymes in different states. In the simulations considered in these studies, the ratio of free to unbound form of the regulated enzymes. Under both simulation conditions, oscillatory motions between the Rapport Leubering shunt, HK and PFK in glycolysis, and nucleotide metabolism are observed. Based upon the large number of reactions involved for the regulated steps as shown in FIG. 9 suggests that there are a large number of possible interactions that can occur for each individual enzyme. This point is made explicitly clear in FIG. 11, which depicts the phase plane diagrams for all 21 of the reactions involving phosphofructokinase. Some of the fluxes are highly correlated, while others exhibit independent motions along different time scales. Thus, regulated reactions are actually subnetworks within metabolic networks.

The NADHP/NADP ratio, G6PD enzyme ratio, and flux through the G6PD reaction are all highly correlated under both conditions (energy and redox stresses), suggesting that either of these measurements can be used to infer the states of the others. Correlations among many of the other variables appear to vary under different conditions.

Conclusions

Stoichiometric genome-scale models have made significant advancements in recent years (26). The incorporation of dynamic information and the ability to describe the kinetics of these networks is an important, physiologically relevant aspect that needs to be accounted for. The kcone formalism took the initial steps towards developing kinetic models in a data driven fashion through sampling the kinetic parameter space (4). Herein we described an approach which uses stoichiometric models as a scaffold for constructing kinetic models based upon bilinear kinetics, through the incorporation of metabolomic data. This stepwise procedure is scaleable and feasible for networks of increasing size.

In order to further expand the mechanistic detail of stoichiometric models, we demonstrated how complex regulatory schemes, which are described with more fidelity as a scheme of bilinear interactions, can fit within this framework of kinetic model construction. Subsequent analysis of the network suggested that the regulatory influence of enzymes is determined by the number of metabolites that can bind to the enzyme. We have previously shown that stoichiometry is a key aspect of kinetic networks (5); here we further highlight that it is also a key factor in regulatory control as well.

Accounting for regulation allows one to observe the subnetworks of regulation within regulated metabolic networks. These subnetworks can exert influences across the whole network, and this appears at least in part in their ability to bind multiple compounds. As with small metabolites, the ratios of enzymes in different forms (e.g. bound versus unbound) reflect different functional states. For some enzymes these are highly correlated with the flux and/or related small metabolite ratios, as with glucose-6-phosphate dehydrogenase. However for other enzymes, particularly those with a larger number of different binding states, such ratios will not always be correlated with fluxes.

Increasing availability of metabolomic data in conjunction with the availability of Keq approximations and related methods for extrapolation and approximation of these constants (27-29) will enable the application of this approach to more metabolic networks. During the preparation of this work, Tran et al (10) describe an approach with similarities to the scheme described herein in which the solution space is sampled for a glycolysis/pentose phosphate pathway model in *E. coli*. The addition of sampling would enable to the exploration of alternative solutions and highlights an area worth further exploration in the future. Taken together, the approach described within this work is scale-able and systematic, thus representing a feasible, realistic path towards genome-scale kinetic descriptions of metabolic networks.

Methods

In general for any reaction, k, +

$$2A \underset{k_1-}{\overset{k_1+}{\rightleftarrows}} B$$

the resulting net rate law is given by, $$vj = k_1^+ A_2 - k_1^- B \quad (1),$$

with the equilibrium constant, $$Keq = k_1^+ / k_1^- \quad (2)$$

For the regulated reactions in the network, the enzymes are explicit species and combined with each metabolite, as outlined in the figures.

Steps for Model Construction—Modular Model Construction

Substituting flux rate expressions (1) and equilibrium constants (2), into the steady state mass balances, $$S \cdot v = 0 \quad (3)$$

for which S is the m×n stoichiometric matrix and v is the flux vector of length n, allows one to solve for the n forward rate constants k. With the rate constants and equilibrium constants in hand in addition to steady state concentrations, the gradient matrix can be defined. The gradient matrix G is given by dv/dx. Decomposition into the dual Jacobian matrices (5) is given by $$J_x = S \cdot G = M \Lambda M'; \quad (4)$$

$$m_x = M_x^{-1} x' \quad (5)$$

for the concentration Jacobian, $J_x$, and $$J_v = G \cdot S = M \Lambda M;' \quad (6)$$

$$m_v = M_v^{-1} v' \quad (7)$$

for the flux Jacobian, Jv. These calculations were carried out for each of the sub-models that were developed in the studies described in the manuscript. The regulated cell model also included magnesium complexing with ATP, ADP, AMP, and 2,3DPG. The matrices S and G are represented for various studies in FIGS. 13-16.

Models were constructed and tested in Mathematica (Wolfram Research). Simulations were also all carried out in Mathematica. However, model construction and simulation can be carried out in any number of other commercial software packages, such as Matlab, free software packages such as Scilab and R, or written in programming and scripting languages such as Java, C++, python, perl, etc. Since the protein concentrations were much smaller than the concentrations of the metabolites, simulations were carried out using normalized enzyme concentrations, in order to reduce the stiffness of the system of differential equations.

When carrying out simulations, the enzyme and bound enzyme variables were normalized, by redefining the enzyme rate constant. This allowed the stiffness of the ordinary differential equations to be significantly reduced. The system was then integrated out to >1000 hours to define the steady state.

This example shows how physiologically meaningful dynamic structures form as a result of the particular numerical values in G and how they overlay on the network structure given by S. Not all sets of numerical values give this dynamic structure. It has been shown that genetic variation, as represented by sequence polymorphism in particular enzymes (pyruvate kinase and glucose-6-phosphate dehydrogenase), can disrupt this dynamic structure and lead to pathological states (Jamshidi et al., 2002).

Example 6

Simulating Genetic Deficiencies in *Homo sapiens* Through Altered Metabolite Measurements Considering the dynamic model constructed in the above examples for metabolism in the human erythrocyte, one can simulate genetic deficiencies through measurements of metabolites. For example a model for a cell with a deficiency in Phosphofructokinase can be constructed and simulated based on metabolite measurements. Following the algorithm for model construction, a new set of forward rate constants will be calculated, resulting in a different set of reaction rate expressions and gradient matrix. Subsequent simulations will reflect the resulting altered biochemical phenotype due to the genetic mutation(s) resulting in Phosphofructokinase Deficiency.

Example 7

Simulating Genetic Deficiencies in *Homo sapiens* Through Altered Rate Constants Considering the dynamic model constructed in the above examples for metabolism in the human erythrocyte, one can simulate genetic deficiencies through measurements of kinetic parameters, such as rate constants. For example, a model for a cell with a deficiency in Phosphofructokinase can be constructed and simulated based on measurements of altered kinetic parameters for the individual regulated steps. The mechanistic representation of the regulation of PFK by other metabolites enables the representation of genetic mutations in a direct, detailed manner. Following the algorithm for model construction, the altered rate constants are adjusted and an altered set of concentrations are recalculated through solving the steady state equations and simulating the time course of the dynamics. This will result in a new set of reaction rate expressions and gradient matrix. Subsequent simulations will reflect the resulting altered biochemical phenotype due to the genetic mutation(s) resulting in Phosphofructokinase Deficiency.

Example 8

Simulating Genetic Deficiencies in *Homo sapiens* Through Altered Lumped Parameter Measurements Considering the dynamic model constructed in the above examples for metabolism in the human erythrocyte, one can simulate genetic deficiencies through measurements of kinetic parameters, such as rate constants. For example, a model for a cell with a deficiency in Phosphofructokinase can be constructed and simulated based on measurements of kinetic parameters such as $V_{max}$. Following the algorithm for model construction, the steady state equations and dynamic simulations are re-implemented. This will result in a new set of reaction rate expressions and gradient matrix. Subsequent simulations will reflect the resulting altered biochemical phenotype due to the genetic mutation(s) resulting in Phosphofructokinase Deficiency.

Example 9

Simulating the Effects of Drugs with Known Targets in *Homo sapiens*

Considering the dynamic model constructed in the above examples for metabolism in the human erythrocyte, one can simulate the effects of known drugs on metabolism. For example, the effect of a redox depleting drug which is known to act on a particular enzyme within the network, such as glucose-6-phosphate dehydrogenase, can be simulated by reducing or abrogating the rate constant for glucose-6-phosphate dehydrogenase by 10%, 20%, 40%, 60%, 80%, or 100%. Following the algorithm for model construction, the altered rate constants are adjusted and an altered set of concentrations are recalculated through solving the steady state equations and simulating the time course of the dynamics. This will result in a new set of reaction rate expressions and gradient matrix. The resulting model will reflect a metabolic network treated with the drug at the specified dose.

Example 10

Simulating the Effects of Drugs with Unknown Targets in *Homo sapiens*

Considering the dynamic model constructed in the above examples for metabolism in the human erythrocyte, one can simulate the effects of known drugs on metabolism and identify potential candidates for the identity of the drug target. For example, metabolite concentration measurements can be made experimentally following the administration of a drug with unknown identity or unknown target. Following the algorithm for model construction, a new set of forward rate constants will be calculated, resulting in a different set of reaction rate expressions and gradient matrix. The resulting model will reflect a metabolic network treated with the drug at the specified dose. Analysis of the Jacobian matrices and dynamic simulations can yield insights into the mechanism of action of the drug and its potential candidate targets.

REFERENCES

The following references are incorporated herein in their entirety:
1. Scriver, C. 2000. The Metabolic and Molecular Bases of Inherited Disease. McGraw-Hill Professional.
2. Jamshidi, N., and B. O. Palsson. 2008. Top-down analysis of temporal hierarchy in biochemical reaction networks. PLoS Comput Biol 4:e1000177.
3. Bruggeman, F. J., J. de Haan, H. Hardin, J. Bouwman, S. Rossell, K. van Eunen, B. M. Bakker, and H. V. Westerhoff. 2006. Time-dependent hierarchical regulation analysis: deciphering cellular adaptation. Systems biology 153:318-322.
4. Famili, I., R. Mahadevan, and B. O. Palsson. 2005. k-Cone analysis: determining all candidate values for kinetic parameters on a network scale. Biophys J 88:1616-1625.
5. Jamshidi, N., and B. O. Palsson. 2008. Formulating genome-scale kinetic models in the post-genome era. Molecular systems biology 4: 171.
6. Maurya, M. R., and S. Subramaniam. 2007. A kinetic model for calcium dynamics in RAW 264.7 cells: I. Mechanisms, parameters, and subpopulational variability. Biophys J 93:709-728.
7. Saucerman, J. J., L. L. Brunton, A. P. Michailova, and A. D. McCulloch. 2003. Modeling beta-adrenergic control of cardiac myocyte contractility in silico. The Journal of biological chemistry 278:47997-48003.
8. Smallbone, K., E. Simeonidis, D. S. Broomhead, and D. B. Kell. 2007. Something from nothing: bridging the gap between constraint-based and kinetic modelling. FEBS J 274:5576-5585.
9. Steuer, R., T. Gross, J. Selbig, and B. Blasius. 2006. Structural kinetic modeling of metabolic networks. Proc Nat! Acad Sci USA 103: 11868-11873.
10. Tran, L. M., M. L. Rizk, and J. C. Liao. 2008. Ensemble modeling of metabolic networks. Biophys J 95:5606-5617.
11. Wishart, D. S., D. Tzur, C. Knox, R. Eisner, A. C. Guo, N. Young, D. Cheng, K. Jewell, D. Arndt, S. Sawhney, C. Fung, L. Nikolai, M. Lewis, M. A. Coutouly, I. Forsythe, P. Tang, S. Shrivastava, K. Jeroncic, P. Stothard, G. Amegbey, D. Block, D. D. Hau, J. Wagner, J. Miniaci, M. Clements, M. Gebremedhin, N. Guo, Y. Zhang, G. E. Duggan, G. D. Macinnis, A. M. Weljie, R. Dowlatabadi, F. Bamforth, D. Clive, R. Greiner, L. Li, T. Marrie, B. D. Sykes, H. J. Vogel, and L. Querengesser. 2007. HMDB: the Human Metabolome Database. Nucleic acids research 35:D521-526.
12. Bennett, B. D., J. Yuan, E. H. Kimball, and J. D. Rabinowitz. 2008. Absolute quantitation of intracellular metabolite concentrations by an isotope ratio-based approach. Nat Protoc 3:1299-1311.
13. Claus, S. P., T. M. Tsang, Y. Wang, O. Cloarec, E. Skordi, F. P. Martin, S. Rezzi, A. Ross, S. Kochhar, E. Holmes, and J. K. Nicholson. 2008. Systemic multicompartmental effects of the gut microbiome on mouse metabolic phenotypes. Molecular systems biology 4:219.
14. Ishii, N., K. Nakahigashi, T. Baba, M. Robert, T. Soga, A. Kanai, T. Hirasawa, M. Naba, K. Hirai, A. Hogue, P. Y. Ho, Y. Kakazu, K. Sugawara, S. Igarashi, S. Harada, T. Masuda, N. Sugiyama, T. Togashi, M. Hasegawa, Y. Takai, K. Yugi, K. Arakawa, N. Iwata, Y. Toya, Y. Nakayama, T. Nishioka, K. Shimizu, H. Mori, and M. Tomita. 2007. Multiple high-throughput analyses monitor the response of *E. coli* to perturbations. Science (New York, N.Y. 316:593-597.
15. Smith, C. A., G. O'Maille, E. J. Want, C. Qin, S. A. Trauger, T. R. Brandon, D. E. Custodio, R. Abagyan, and G. Siuzdak. 2005. METLIN: a metabolite mass spectral database. Ther Drug Moni t 27: 747-751.

16. Joshi, A., and B. O. Palsson. 1990. Metabolic dynamics in the human red cell. Part IV-Data prediction and some model computations. J Theor Bioi 142:69-85.

17. Joshi, A., and B. O. Palsson. 1990. Metabolic dynamics in the human red cell. Part III—Metabolic reaction rates. J Theor Bioi 142:41-68.

18. Reich, J., and E. Selkov. 1981. Energy metabolism of the cell: a theoretical treatise. Academic Press.

19. Jamshidi, N., J. S. Edwards, T. Fahland, G. M. Church, and B. O. Palsson. 2001. Dynamic simulation of the human red blood cell metabolic network. Bioinformatics 17:286-287.

20. Jamshidi, N., and B. O. Palsson. 2006. Systems biology of the human red blood cell. Blood cells, molecules & diseases 36:239-247.

21. Kauffman, K. J., J. D. Pajerowski, N. Jamshidi, B. O. Palsson, and J. S. Edwards. 2002. Description and analysis of metabolic connectivity and dynamics in the human red blood cell. Biophys J 83:646-662.

22. Segel, I. 1975. Enzyme Kinetics. John Wiley & Sons.

23. Mulquiney, P. J., and P. W. Kuchel. 1999. Model of 2,3-bisphosphoglycerate metabolism in the human erythrocyte based on detailed enzyme kinetic equations: equations and parameter refinement. Biochem J 342 Pt 3:581-596.

24. Albe, K. R., M. H. Butler, and B. E. Wright. 1990. Cellular concentrations of enzymes and their substrates. J Theor Bioi 143:163-195.

25. Hawkins, C. F., and A. S. Bagnara. 1987. Adenosine kinase from human erytluocytes: kinetic studies and characterization of adenosine binding sites. Biochemistry 26: 1982-1987.

26. Feist, A. M., M. J. Herrgard, 1. Thiele, J. L. Reed, and B. O. Palsson. 2009. Reconstruction of biochemical networks in microorganisms. Nat Rev Microbiol 7: 129-143.

27. Alberty, R. A. 2003. Thermodynamics of biochemical reactions. Wiley-Interscience, Hoboken, N.J.

28. Jankowski, M. D., C. S. Henry, L. J. Broadbelt, and V. Hatzimanikatis. 2008. Group contribution method for thermodynamic analysis of complex metabolic networks. Biophys J 95:1487-1499.

29. Mavrovouniotis, M. L. 1991. Estimation of standard Gibbs energy changes of biotransformations. The Journal of biological chemistry 266:14440-14445.

30. Mahadevan, R., and C. H. Schilling. 2003. The effects of alternate optimal solutions in constraint-based genome-scale metabolic models. Metabolic engineering 5:264-276.

31. Mulquiney, P. J., W. A. Bubb, and P. W. Kuchel. 1999. Model of 2,3-bisphosphoglycerate metabolism in the human erythrocyte based on detailed enzyme kinetic equations: in vivo kinetic characterization of 2,3-bisphosphoglycerate synthase/phosphatase using 13C and 31P NMR. Biochem J 342 Pt 3:567-580.

What is claimed is:

1. A computer-implemented method for developing data-driven dynamic models of biological networks comprising:
providing, at a computer system, a data structure relating a plurality of biological network reactants to a plurality of biological network reactions, the plurality of biological network reactions comprising one or more flux distributions, wherein each of the biological network reactions comprises one or more biological network reactants identified as a substrate of the reaction, one or more biological network reactants identified as a product of the biological network reaction and a stoichiometric coefficient relating the substrate and the product;
providing, at a computer system, a constraint set for the plurality of biological network reactions;
providing, at a computer system, a constraint set for a plurality of concentrations associated with the plurality of biological network reactions;
providing, at a computer system, a constraint set for a plurality of kinetic constants associated with the plurality of biological network reactions;
providing, at a computer system, a constraint set for a plurality of equilibrium constants associated with the plurality of biological network reactions;
integrating, at a computer system, the sets of constraints, thereby forming stoichiometric, gradient, and Jacobian matrices;
providing, at a computer system, an objective function; and
predicting, at a computer system, a physiological function related to at least one of the biological networks by determining using the computer system at least one flux distribution, from the one or more flux distributions, that minimizes or maximizes the objective function when at least one constraint set from the sets of constraints is applied to the data structure.

2. The method of claim 1, wherein the constraints for the plurality of reactions, the constraints for the plurality of concentrations, the constraints for the plurality of kinetic constants, and the constraints for the plurality of equilibrium constants are separately defined.

3. The method of claim 1, wherein providing a constraint set for a plurality of concentrations comprises measuring metabolite levels at steady state.

4. The method of claim 1, wherein providing a constraint set for a plurality of kinetic constants comprises solving a steady state mass conservation relationship comprising a stoichiometric matrix and flux vector.

5. The method of claim 1, further comprising defining a unique set of matrices using the objective function,
wherein the constraints within at least one of the sets selected from the reactions constraint set, the concentration constraint set, the kinetic constant constraint set, and the equilibrium constraint set are not unique across the set.

6. The method of claim 1, further comprising defining a unique set of gradient and Jacobian matrices using order of magnitude approximations,
wherein the constraints within at least one of the sets selected from the reactions constraint set, the concentration constraint set, the kinetic constant constraint set, and the equilibrium constraint set are not unique across the set.

7. The method of claim 1, further comprising determining a set of gradient and Jacobian matrices corresponding to the plurality of constraint conditions,
wherein the constraints within at least one of the sets selected from the reactions constraint set, the concentration constraint set, the kinetic constant constraint set, and the equilibrium constraint set are not unique across the set.

8. The method of claim 1, wherein constraints within at least one of the concentration constraint set and the kinetic constant constraint set are not unique across the set and are estimated by order of magnitude approximations.

9. The method of claim 1, wherein the stoichiometric, gradient, and Jacobian matrices refer to a biological network process.

10. The method of claim 9, wherein the biological network process comprises at least one of metabolism, signal transduction or signaling, transcription, and translation.

11. The method of claim 1, wherein the sets of constraints correspond to an individual.

12. The method of claim 1, wherein the sets of constraints correspond to a group or plurality of individuals.

13. The method of claim 1, wherein the model is used to determine the effects of changes from aerobic to anaerobic conditions.

14. The method of claim 1, wherein the biological network reactions are obtained from a metabolic reaction database that includes the substrates, products, and stoichiometry of a plurality of biological reactions.

15. A computer-implemented method for the analysis of disease states due to genetic and/or environmental influences comprising:
providing, at a computer system, a data structure relating a plurality of reactants to a plurality of reactions, the plurality of reactions comprising one or more flux distributions, wherein each of the reactions comprises one or more reactants identified as a substrate of the reaction, one or more reactants identified as a product of the reaction and a stoichiometric coefficient relating the substrate and the product;
providing, at a computer system, a constraint set for the plurality of reactions;
providing, at a computer system, a constraint set for a plurality of concentrations associated with the plurality of reactions;
providing, at a computer system, a constraint set for a plurality of kinetic constants associated with the plurality of reactions;
providing, at a computer system, a constraint set for a plurality of equilibrium constants associated with the plurality of reactions;
integrating, at a computer system, the sets of constraints, thereby forming stoichiometric, gradient, and Jacobian matrices;
providing, at a computer system, an objective function;
modifying, at a system, at least one of the reaction constraint set, the concentration constraint set, the kinetic constant set and the equilibrium constant set based at least partly on genetic variations;
modifying, at a computer system, at least one of the reaction constraint set, the concentration constraint set, the constraint set for a plurality of kinetic constants and the set for a plurality of equilibrium constants based at least partly on altered environmental conditions; and
predicting, using a computer system, a physiological function related to one of the disease states by determining at least one flux distribution, from the one or more flux distributions, that minimizes or maximizes the objective function when at least one constraint set from the sets of constraints is applied to the data structure.

16. The method of claim 15, wherein the method is used to determine the dynamics and consequences of genetic defects selected from the group consisting of deficiencies in metabolic enzymes and metabolic transporters.

17. The method of claim 16, wherein the genetic defects comprise the functioning of a compound selected from the group consisting of phosphofructokinase, phosphoglycerate kinase, phosphoglycerate mutase, lactate dehydrogenase adenosine deaminase, ABC transporters, the SLC class of transporters, and the cytochrome P450 class of enzymes.

18. The method of claim 15, wherein providing a constraint set for a plurality of concentrations comprises measuring metabolite levels at steady state.

19. The method of claim 15, wherein providing a constraint set for a plurality of kinetic constants comprises solving a steady state mass conservation relationship comprising a stoichiometric matrix and flux vector.

20. The method of claim 15, wherein the modified sets of constraints correspond to an individual.

21. The method of claim 15, wherein the modified sets of constraints correspond to a group or plurality of individuals.

22. The method of claim 15, wherein a therapeutic regime is applied to regulate a physiological function based on at least one of the modified sets based at least partly on genetic variations.

23. The method of claim 15, wherein a therapeutic regime is applied to regulate a physiological function based on at least one of the modified sets based at least partly on altered environmental conditions.

24. A computer-implemented method for the analysis of therapies for drug treatments, the method comprising:
providing, at a computer system, a data structure relating a plurality of reactants to a plurality of reactions, the plurality of reactions comprising one or more flux distributions, wherein each of the reactions comprises one or more reactants identified as a substrate of the reaction, one or more reactants identified as a product of the reaction and a stoichiometric coefficient relating the substrate and the product;
providing, at a computer system, a constraint set for the plurality of reactions;
providing, at a computer system, a constraint set for a plurality of concentrations associated with the plurality of reactions;
providing, at a computer system, a constraint set for a plurality of kinetic constants associated with the plurality of reactions;
providing, at a computer system, a constraint set for a plurality of equilibrium constants associated with the plurality of reactions;
integrating, at a computer system, the sets of constraints, thereby forming stoichiometric, gradient, and Jacobian matrices;
providing, at a computer system, an objective function;
providing, at a computer system, an experimental constraint set for the plurality of reactions, concentrations, or kinetic constants for an altered set of constraints due to a treatment with a drug or chemical agent; and
predicting, at a computer system, a physiological function related to the drug treatment by determining at least one flux distribution, from the one or more flux distributions, that minimizes or maximizes the objective function when a constraint set is applied to the data structure.

25. The method of claim 24, wherein a set of fluxes and concentrations are measured in an individual before and after giving a dose of a therapeutic agent to the individual and constructing kinetic network models according to the measured data specific to the individual.

26. The method of claim 24, wherein providing a constraint set for a plurality of concentrations comprises measuring metabolite levels at steady state.

27. The method of claim 24, wherein providing a constraint set for a plurality of kinetic constants comprises solving a steady state mass conservation relationship comprising a stoichiometric matrix and flux vector.

28. The method of claim 24, wherein a physiological function related to a drug treatment is instead predicted by determining at least one concentration that maximizes or minimizes the objective function when the experimental constraint set is applied to the data structure.

29. The method of claim 24, wherein a drug or chemical agent is applied to regulate a physiological function based on the at least one experimental constraint set for an altered state of constraints due to the treatment with a drug or chemical agent.

30. The method of claim 24, wherein a drug or chemical agent is applied to regulate a physiological function based on the at least one experimental constraint set which maximizes or minimizes the objective function when the experimental constraint set is applied to the data structure.

31. The method of claim 24, wherein the sets of constraints correspond to an individual.

32. The method of claim 24, wherein the sets of constraints correspond to a group or plurality of individuals.

33. A computer-implemented method for accounting for small metabolite regulation comprising:
provide, at a computer system, a data structure relating a plurality of reactants to a plurality of reactions, the plurality of reactions comprising one or more flux distributions, wherein each of the reactions comprises one or more reactants identified as a substrate of the reaction, one or more reactants identified as a product of the reaction and a stoichiometric coefficient relating the substrate and the product, in which the reactions may reflect regulatory processes;
providing, at a computer system, a constraint set for the plurality of reactions;
providing, at a computer system, a constraint set for a plurality of concentrations associated with the plurality of reactions;
providing, at a computer system, a constraint set for a plurality of kinetic constants associated with the plurality of reactions;
providing, at a computer system, a constraint set for a plurality of equilibrium constants associated with the plurality of reactions;
integrating, at a computer system, the sets of constraints, thereby forming stoichiometric, gradient, and Jacobian matrices;
providing, at a computer system, an objective function; and
predicting, at a computer system, a physiological function related to the small metabolite regulation by determining using the computer system at least one flux distribution, from the one or more flux distributions, that minimizes or maximizes the objective function when at least one constraint set from the sets of constraints is applied to the data structure.

34. The method of claim 33, wherein providing a constraint set for a plurality of concentrations comprises measuring metabolite levels at steady state.

35. The method of claim 33, wherein a physiological function related to the small metabolite regulation is instead predicted by determining at least one concentration that minimizes or maximizes the objective function when the constraint set is applied to the data structure.

36. The method of claim 33, wherein reactants and products include proteins that interact with a plurality of other components.

37. The method of claim 33, wherein reactants or products activate a particular enzyme or plurality of enzymes.

38. The method of claim 33, wherein reactants or products inhibit a particular enzyme or plurality of enzymes.

39. A computer-implemented method for determining one or more parameters to characterize different functional states comprising:
analyzing, at a computer system, a network function;
determining, at a computer system, time scales of interest; and
identifying, at a computer system, parameters that describe the network function based on at least one of a stoichiometric, gradient, or Jacobian matrix, the stoichiometric, gradient, or Jacobian matrix formed, at least in part, based on an integration of a set of constraints, wherein the constraint set comprises a plurality of mass action relationships which also incorporate metabolomic data and thermodynamic data.

40. The method of claim 39, wherein the parameters comprise at least one of a reaction, a concentration and a rate constant.

41. The method of claim 39, further comprising characterizing the dynamic behavior of the network using the time scale determination; and
identifying reactions or concentrations that determine the network function.

42. A non-transitory computer readable medium containing software embedded in the computer readable medium, the software configured such that, when executed, it causes one or more computer systems to perform the acts of:
receiving a data structure relating a plurality of reactants to a plurality of reactions, the plurality of reactions comprising one or more flux distributions, wherein each of the reactions comprises one or more reactants identified as a substrate of the reaction, one or more reactants identified as a product of the reaction and a stoichiometric coefficient relating the substrate and the product;
receiving a constraint set for the plurality of reactions;
receiving a constraint set for a plurality of concentrations associated with the plurality of reactions;
receiving a constraint set for a plurality of kinetic constants associated with the plurality of reactions;
receiving a constraint set for a plurality of equilibrium constants associated with the plurality of reactions;
integrating the sets of constraints, thereby forming stoichiometric, gradient, and Jacobian matrices;
receiving an objective function; and
predicting a physiological function by determining at least one flux distribution, from the one or more flux distributions, that minimizes or maximizes the objective function when the constraint set from the sets of constraints is applied to the data structure.

43. A computer implemented system comprising:
a computing environment;
a storage in data communication with the computing environment and configured to store data structure relating a plurality of reactants to a plurality of reactions; and
a software program operating on the computing environment and configured to:
provide the data structure relating the plurality of reactants to the plurality of reactions, the plurality of reactions comprising one or more flux distributions, wherein each of the reactions comprises one or more reactants identified as a substrate of the reaction, one or more reactants identified as a product of the reaction and a stoichiometric coefficient relating the substrate and the product;
provide a constraint set for the plurality of reactions;
provide a constraint set for a plurality of concentrations associated with the plurality of reactions;
provide a constraint set for a plurality of kinetic constants associated with the plurality of reactions;
provide a constraint set for a plurality of equilibrium constants associated with the plurality of reactions;

integrate the sets of constraints, thereby forming a stoichiometric, gradient, and Jacobian matrices;

provide an objective function; and predict a physiological function by determining at least one flux distribution, from the one or more flux distributions, that minimizes or maximizes the objective function when the constraint set from the sets of constraints is applied to the data structure.

44. A system comprising:

means for providing a data structure relating a plurality of reactants to a plurality of reactions, the pluralality of biological network reactions comprising one or more flux distributions, wherein each of the reactions comprises one or more reactants identified as a substrate of the reaction, one or more reactants identified as a product of the reaction and a stoichiometric coefficient relating the substrate and the product;

means for providing a constraint set for the plurality of reactions;

means for providing a constraint set for a plurality of concentrations associated with the plurality of reactions;

means for providing a constraint set for a plurality of kinetic constants associated with the plurality of reactions;

means for providing a constraint set for a plurality of equilibrium constants associated with the plurality of reactions;

means for integrating the sets of constraints, thereby forming stoichiometric, gradient, and Jacobian matrices;

means for providing an objective function; and means for predicting a physiological function based on the objective function and at least one of the constraint sets.

45. A computer-implemented method for predicting a physiological function comprising:

providing, at a computer system, a data structure relating a plurality of *H. sapiens* reactants to a plurality of *H. sapiens* reactions, wherein said *H. sapiens* reactions comprise one or more reactants identified as a substrate of the reaction, one or more reactants identified as a product of the reaction and a stoichiometric coefficient relating the substrate and the product;

providing, at a computer system, a constraint set for the plurality of *H. sapiens* reactions, wherein the constraint set comprises a plurality of mass action relationships which also incorporate metabolomic data and thermodynamic data;

providing, at a computer system, an objective function;

determining, at a computer system, at least one flux distribution that minimizes or maximizes the objective function when the constraint set is applied to the data structure, thereby predicting a *H. sapiens* physiological function; and integrating, at a computer system, the set of constraints to form at least a stoichiometric, gradient, or Jacobian matrix.

46. The method of claim 45, wherein the physiological function comprises at least one of cellular growth, energy production, redox equivalent production, biomass production, development, or consumption of carbon, nitrogen, sulfur, phosphate, hydrogen or oxygen.

47. The method of claim 45, wherein the physiological function comprises a *H. sapiens* reaction comprising one of biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite and metabolism of an alternative carbon source.

48. The method of claim 45, wherein the physiological function is an emergent property.

49. The method of claim 45, wherein the physiological function is used to determine a phenotype.

50. The method of claim 45, wherein the physiological function is correlated with the effects of adding or deleting a gene that encodes for a gene product that performs a reaction in a metabolic pathway.

51. The method of claim 45, wherein a candidate compound is synthesized so as to affect the physiological function; the compound selected by at least one of adding a reaction to the model, removing a reaction from the model and adjusting a constraint for a reaction in the model to reflect the measured effect of the candidate drug or agent on the activity of the reaction.

\* \* \* \* \*